[12] United States Patent
Yeh et al.

(10) Patent No.: US 9,499,866 B2
(45) Date of Patent: Nov. 22, 2016

(54) COMPOSITIONS AND METHODS FOR DETECTING SINGLE NUCLEOTIDE POLYMORPHISMS

(71) Applicant: Los Alamos National Security, LLC, Los Alamos, NM (US)

(72) Inventors: Hsin-Chih Yeh, Austin, TX (US); James Werner, Los Alamos, NM (US); Jennifer S. Martinez, Dixon, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 14/284,776

(22) Filed: May 22, 2014

(65) Prior Publication Data

US 2014/0349289 A1    Nov. 27, 2014

Related U.S. Application Data

(60) Provisional application No. 61/826,225, filed on May 22, 2013.

(51) Int. Cl.

| | |
|---|---|
| *G01N 33/00* | (2006.01) |
| *G01N 33/20* | (2006.01) |
| *G01N 33/53* | (2006.01) |
| *C07H 21/04* | (2006.01) |
| *C12Q 1/68* | (2006.01) |

(52) U.S. Cl.
CPC ............ *C12Q 1/6881* (2013.01); *C12Q 1/6827* (2013.01); *C12Q 1/6883* (2013.01); *C12Q 2600/156* (2013.01)

(58) Field of Classification Search
None
See application file for complete search history.

(56) References Cited

U.S. PATENT DOCUMENTS

2011/0212540 A1*  9/2011  Yeh ..................... C12Q 1/6816
                                                                436/501

OTHER PUBLICATIONS

"Viruses" (Wikipedia.com, accessed Nov. 24, 2012).*
"How many species of bacteria are there" (wisegeek.com; accessed Jan. 21, 2014).*
"Mammal," (Wikipedia.com; accessed Sep. 22, 2011).*
"Murinae," (Wikipedia.com, accessed Mar. 18, 2013).*
"Fish," (Wikipedia.com, accessed Nov. 2, 2014).*
"Human Hybrids," by Michael F. Hammer, Scientific American, May 2013, pp. 66-71.*
Antoku. "Fluorescent polycytosine-encapsulated silver nanoclusters." (2007). Ph.D. Dissertation, Georgia Institute of Technology, 2007.
Arakawa, et al. "Silver (I) complexes with DNA and RNA studied by Fourier transform infrared spectroscopy and capillary electrophoresis." *Biophysical journal* 81.3 (2001): 1580-1587.
Bates, et al. "Short-range spectroscopic ruler based on a single-molecule optical switch." *Physical review letters* 94.10 (2005): 108101.
Boon, et al. "Mutation detection by electrocatalysis at DNA-modified electrodes." *Nature biotechnology* 18.10 (2000): 1096-1100.
Buck, et al. "DNA nanoswitch as a biosensor." *Analytical chemistry* 79.12 (2007): 4724-4728.
De Kok, et al. "Rapid genotyping of single nucleotide polymorphisms using novel minor groove binding DNA oligonucleotides (MGB probes)." *Human mutation* 19.5 (2002): 554-559.
Díez. e al. "Fluorescent silver nanoclusters." *Nanoscale* 3.5 (2011): 1963-1970.
Giljohann, et al. "Drivers of biodiagnostic development." *Nature* 462.7272 (2009): 461-464.
Guo, et al. "Highly sequence-dependent formation of fluorescent silver nanoclusters in hybridized DNA duplexes for single nucleotide mutation identification." *Journal of the American Chemical Society* 132.3 (2009): 932-934.
Gwinn, et al. "Sequence-Dependent Fluorescence of DNA-Hosted Silver Nanoclusters." *Advanced Materials* 20.2 (2008): 279-283.
Heinlein, et al. "Photoinduced electron transfer between fluorescent dyes and guanosine residues in DNA-hairpins." *The Journal of Physical Chemistry* 107.31 (2003): 7957-7964.
Ho, et al. "Mutations of BRAF and KRAS precede the development of ovarian serous borderline tumors." *Cancer research* 64.19 (2004): 6915-6918.
Inouye, et al. "Single-nucleotide polymorphism detection with "wire-like" DNA probes that display quasi "on-off" digital action." *Proceedings of the National Academy of Sciences of the United States of America* 102.33 (2005): 11606-11610.
Kolpashchikov. "Binary malachite green aptamer for fluorescent detection of nucleic acids." *Journal of the American Chemical Society* 127.36 (2005): 12442-12443.
König, et al. "Chemiluminescence in the agglomeration of metal clusters." *Science* 274.5291 (1996): 1353-1354.
Kostrikis, et al. "Spectral genotyping of human alleles." *Science* (New York, NY) 279.5354 (1998): 1228-1229.

(Continued)

*Primary Examiner* — Bradley L Sisson
(74) *Attorney, Agent, or Firm* — Klarquist Sparkman, LLP

(57) ABSTRACT

Described herein are nucleic acid based probes and methods for discriminating and detecting single nucleotide variants in nucleic acid molecules (e.g., DNA). The methods include use of a pair of probes can be used to detect and identify polymorphisms, for example single nucleotide polymorphism in DNA. The pair of probes emit a different fluorescent wavelength of light depending on the association and alignment of the probes when hybridized to a target nucleic acid molecule. Each pair of probes is capable of discriminating at least two different nucleic acid molecules that differ by at least a single nucleotide difference. The methods can probes can be used, for example, for detection of DNA polymorphisms that are indicative of a particular disease or condition.

8 Claims, 29 Drawing Sheets
(29 of 29 Drawing Sheet(s) Filed in Color)

(56) References Cited

OTHER PUBLICATIONS

Kurman, et al. "Pathogenesis of ovarian cancer. Lessons from morphology and molecular biology and their clinical implications." *International journal of gynecological pathology: official journal of the International Society of Gynecological Pathologists* 27.2 (2008): 151.

Kwok. "Methods for genotyping single nucleotide polymorphisms." *Annual review of genomics and human genetics* 2.1 (2001): 235-258.

Lee, et al. "Strongly enhanced field-dependent single-molecule electroluminescence." *Proceedings of the National Academy of Sciences* 99.16 (2002): 10272-10275.

Lilley. "Structures of helical junctions in nucleic acids." *Quaterly reviews of biophysics* 33.02 (2000): 109-159.

Mhlanga, et al. "Using molecular beacons to detect single-nucleotide polymorphisms with real-time PCR." *Methods* 25.4 (2001): 463-471.

Neidig, et al. "Ag K-edge EXAFS analysis of DNA-templated fluorescent silver nanoclusters: insight into the structural origins of emission tuning by DNA sequence variations." *Journal of the American Chemical Society* 133.31 (2011): 11837-11839.

Okamoto, et al. "Pyrene-labeled base-discriminating fluorescent DNA probes for homogeneous SNP typing." *Journal of the American Chemical Society* 126.15 (2004): 4820-4827.

Okamoto, et al. "Design of base-discriminating fluorescent nucleosides." *Journal of Photochemistry and Photobiology C: Photochemistry Reviews* 6.2 (2005): 108-122.

O'Neill, et al. "UV excitation of DNA stabilized Ag cluster fluorescence via the DNA bases," *The Journal of Physical Chemistry C* 115.49 (2011): 24061-24066.

O'Neill, et al. "Hairpins with poly-C loops stabilize four types of fluorescent Ag n: DNA." *The Journal of Physical Chemistry C* 113.11 (2009): 4229-4233.

Park, et al. "Array-based electrical detection of DNA with nanoparticle probes." *Science* 295.5559 (2002): 1503-1506.

Petty, et al. "DNA sensing by amplifying the number of near-infrared emitting, oligonucleotide-encapsulated silver clusters." *Analytical chemistry* 83.15 (2011): 5957-5964.

Petty, et al. "DNA-templated Ag nanocluster formation." *Journal of the American Chemical Society* 126.16 (2004): 5207-5212.

Ritchie, et al. "Ag nanocluster formation using a cytosine oligonucleotide template." *The Journal of Physical Chemistry C* 111.1 (2007): 175-181.

Rodger. *Circular dichroism and linear dichroism*. John Wiley & Sons, Ltd, 1997.

Sharma, et al. "Silver nanocluster aptamers: in situ generation of intrinsically fluorescent recognition ligands for protein detection." *Chem. Commun.* 47.8 (2011):2294-2296.

Sharma, et al. "A complementary palette of fluorescent silver nanoclusters." *Chem. Commun.* 46.19 (2010): 3280-3282.

Sönnichsen, et al. "A molecular ruler based on plasmon coupling of single gold and silver nanoparticles." *Nature biotechnology* 23.6 (2005): 741-745.

Soto-Verdugo, et al. "The properties of small Ag clusters bound to DNA bases," *The Journal of chemical physics* 132.19 (2010): 195102.

Star, et al. "Label-free detection of DNA hybridization using carbon nanotube network field-effect transistors." *Proceedings of the National Academy of Sciences of the United States of America* 103.4 (2006): 921-926.

Stryer, et al. "Energy transfer: a spectroscopic ruler," *Proceedings of the National Academy of Sciences of the United States of America* 58.2 (1967): 719.

Subramanian, et al. "The label-free unambiguous detection and symbolic display of single nucleotide polymorphisms on DNA origami" *Nano letters* 11.2.(2011): 910-913.

Tian, et al. "Single-nucleotide mutation rate increases close to insertions/deletions in eukaryotes." *Nature* 455.7209 (2008): 105-108.

Vosch, et al. "Strongly emissive individual DNA-encapsulated Ag nanoclusters as single-molecule fluorophores." *Proceedings of the National Academy of Sciences* 104.31 (2007): 12616-12621.

Wang, et al. "Large-scale identification, mapping, and genotyping of single-nucleotide polymorphisms in the human genome." *Science* 280.5366 (1998): 1077-1082.

Wilentz, et al. "K-ras mutations in the duodenal fluid of patients with pancreatic carcinoma." *Cancer* 82.1 (1998): 96-103.

Xiao, et al. "Fluorescence Detection of Single Nucleotide Polymorphisms via a Single, Self-Complementary, Triple-stem DNA Probe." *Angew. Chem. Int. Ed. Engl.* 48(24) (2009): 4354-4358.

Xu, et al. "Water-Soluble Fluorescent Silver Nanoclusters." *Advanced Materials* 22.10 (2010): 1078-1082.

Yang, et al. "Protein conformational dynamics probed by single-molecule electron transfer," *Science* 302.5643 (2003): 262-266.

Yau, et al. "Bright two-photon emission and ultra-fast relaxation dynamics in a DNA-templated nanocluster investigated by ultra-fast spectroscopy." *Nanoscale* 4.14 (2012): 4247-4254.

Yeh, et al. "Homogeneous point mutation detection by quantum dot-mediated two-color fluorescence coincidence analysis." *Nucleic acids research* 34.5 (2006): e35-e35.

Yeh, et al. "Tunable blinking kinetics of Cy5 for precise DNA quantification and single-nucleotide difference detection," *Biophysical journal* 95.2 (2008): 729-737.

Yeh, et al. "A DNA—Silver Nanocluster Probe That Fluoresces upon Hybridization." *Nano letters* 10.8 (2010): 3106-3110.

Yeh, et al. "A Beacon of Light." *Nanotechnology Magazine, IEEE*, (2011): 28-33.

Yeh, et al. "Photophysical characterization of fluorescent metal nanoclusters synthesized using oligonucleotides, proteins and small molecule ligands." *Proc. of SPIE*, vol. 7576. 2010.

Yeh, et al. "A fluorescence light-up Ag nanocluster probe that discriminates single-nucleotide variants by emission color." *Journal of the American Chemical Society* 134.28 (2012): 11550-11558.

Yun, et al. "Nanometal surface energy transfer in optical rulers, breaking the FRET barrier." *Journal of the American Chemical Society* 127.9 (2005): 3115-3119.

Zhong, et al. "Single-nucleotide polymorphism genotyping on optical thin-film biosensor chips." *Proceedings of the National Academy of Sciences* 100.20 (2003):11559-11564.

\* cited by examiner

Wild-type target

Mutant-type target

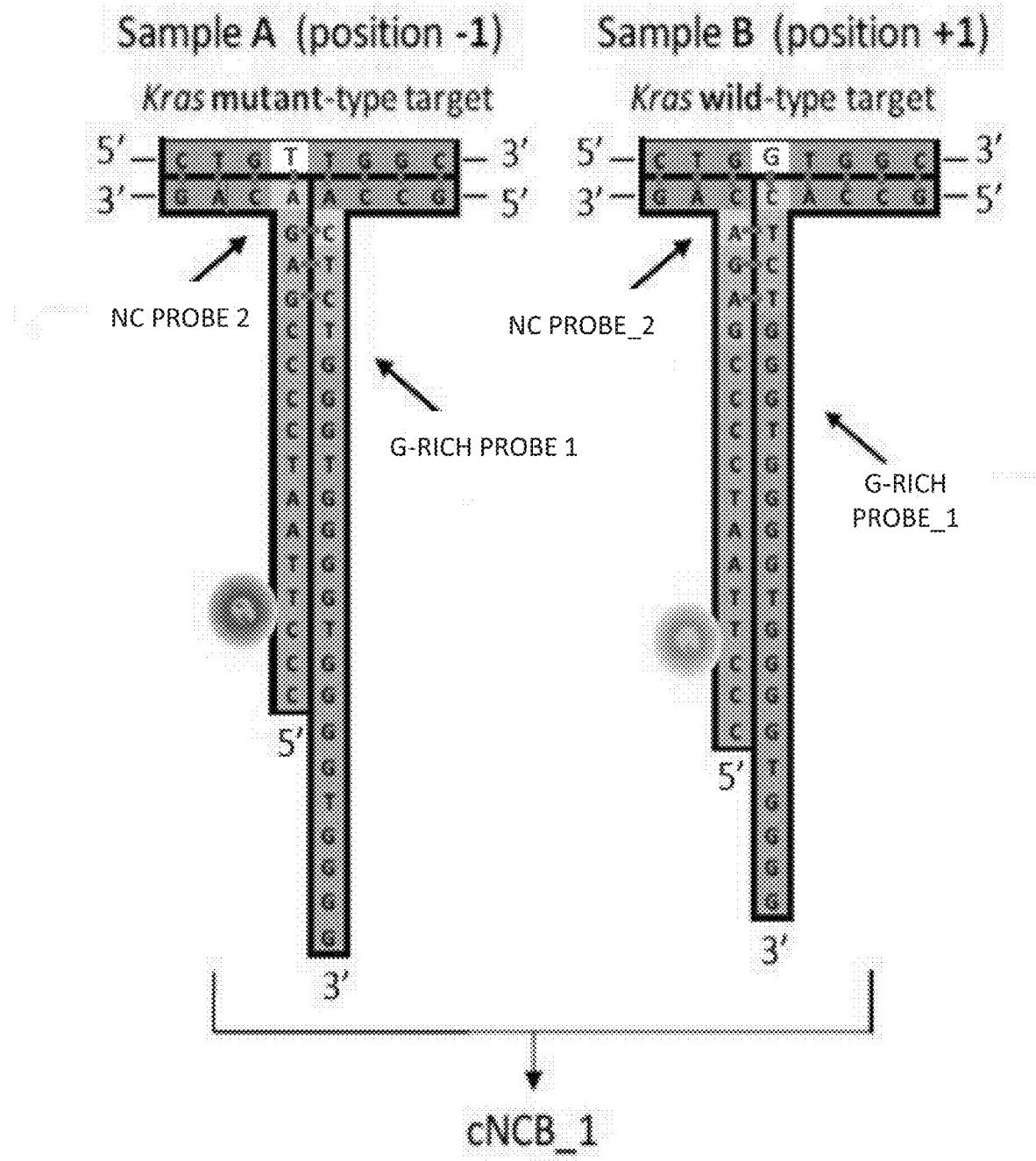

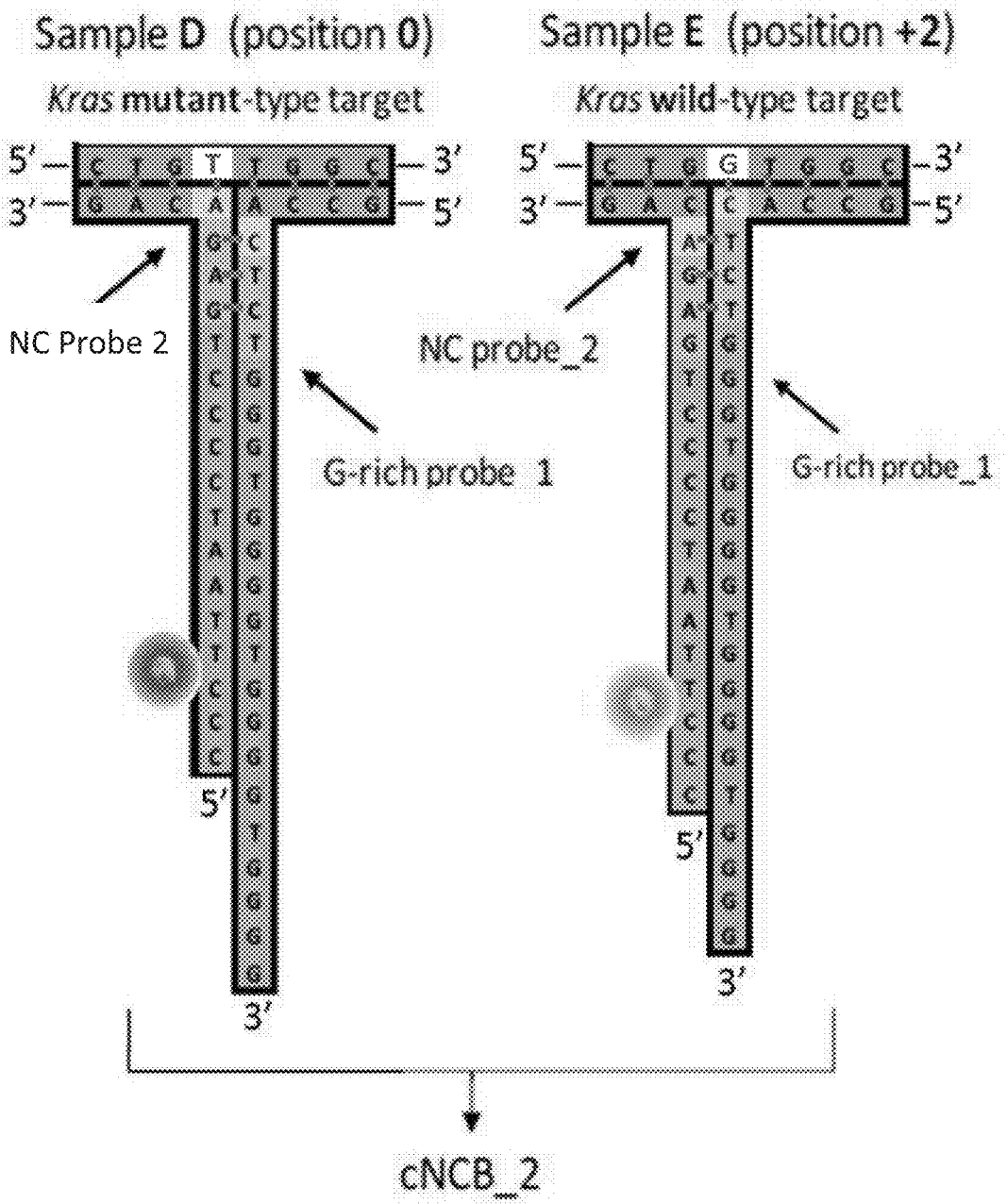

FIG. 6B       *Kras* Targets
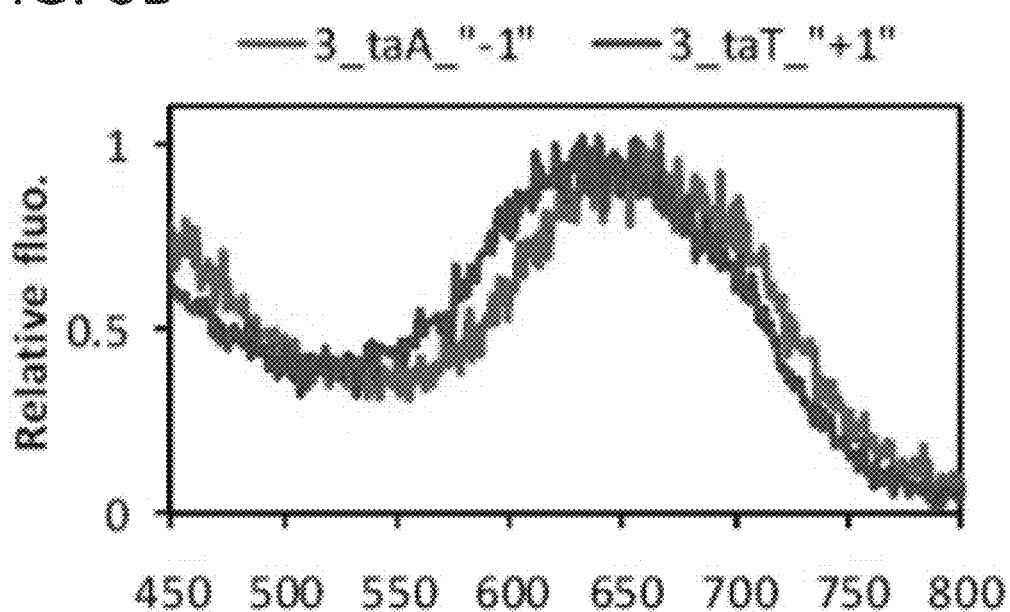
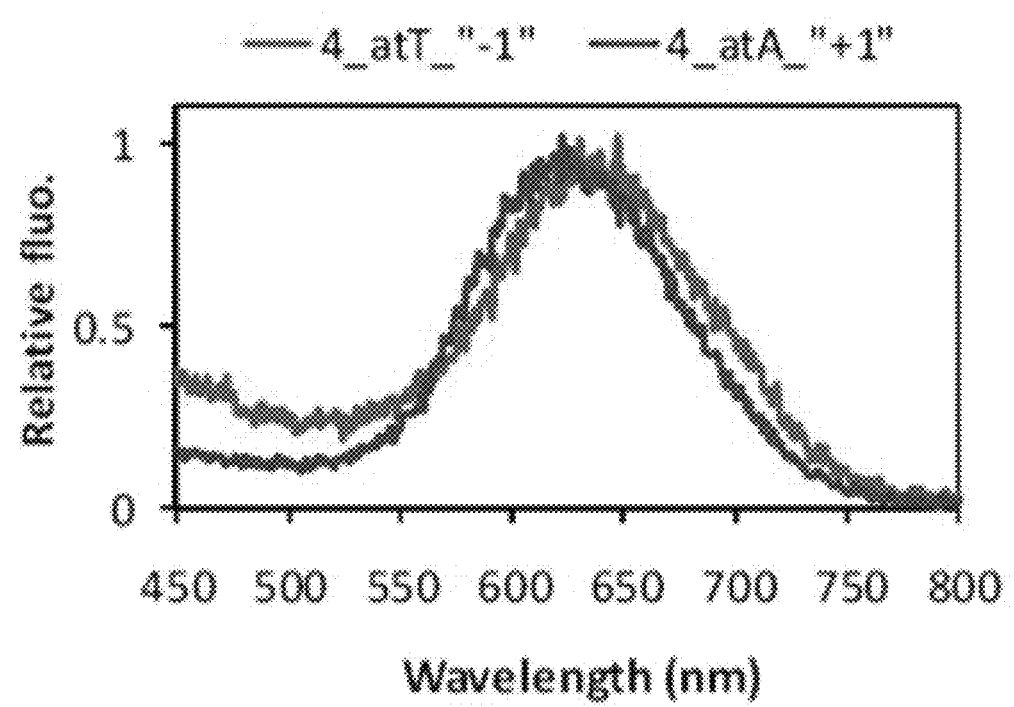

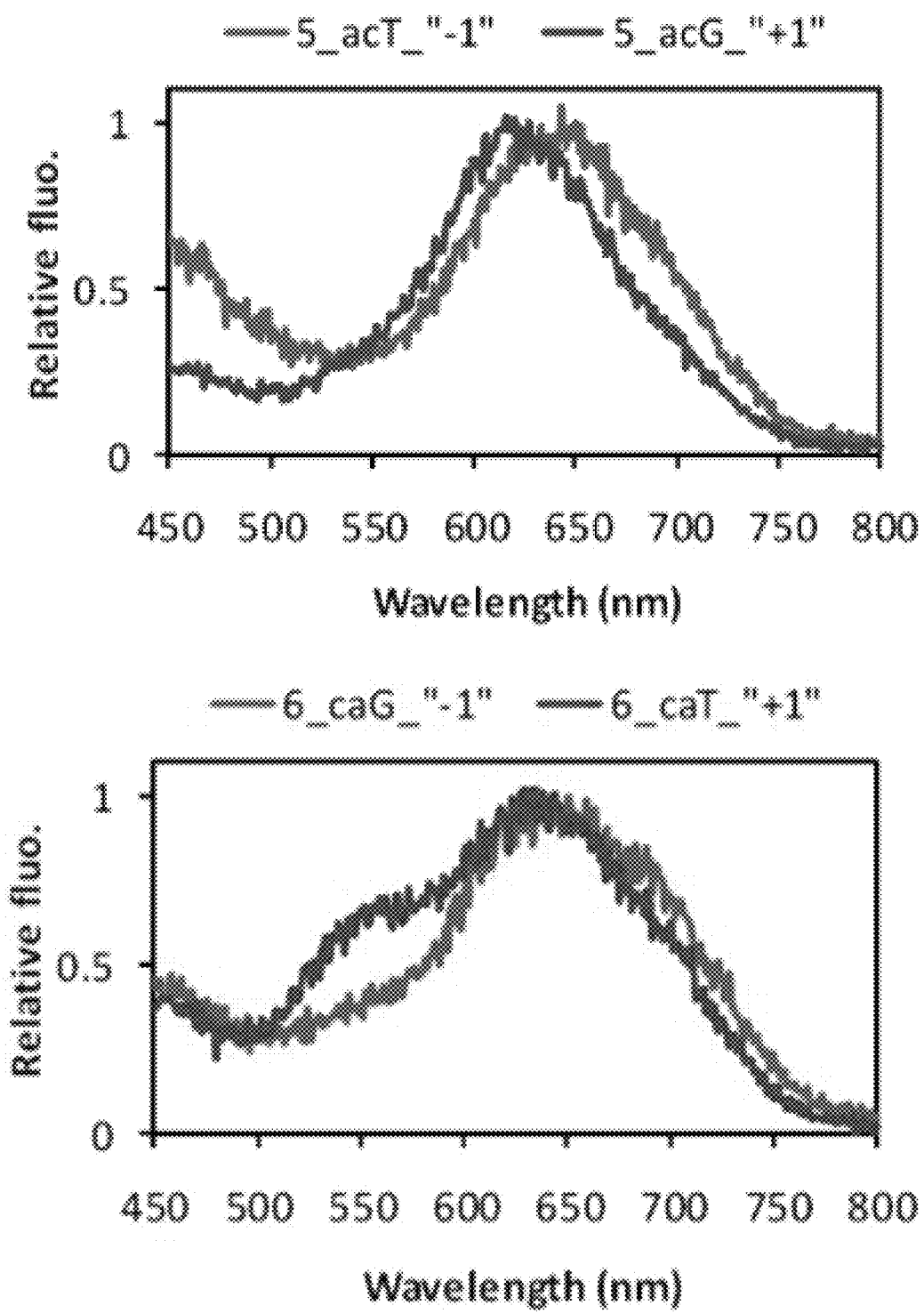

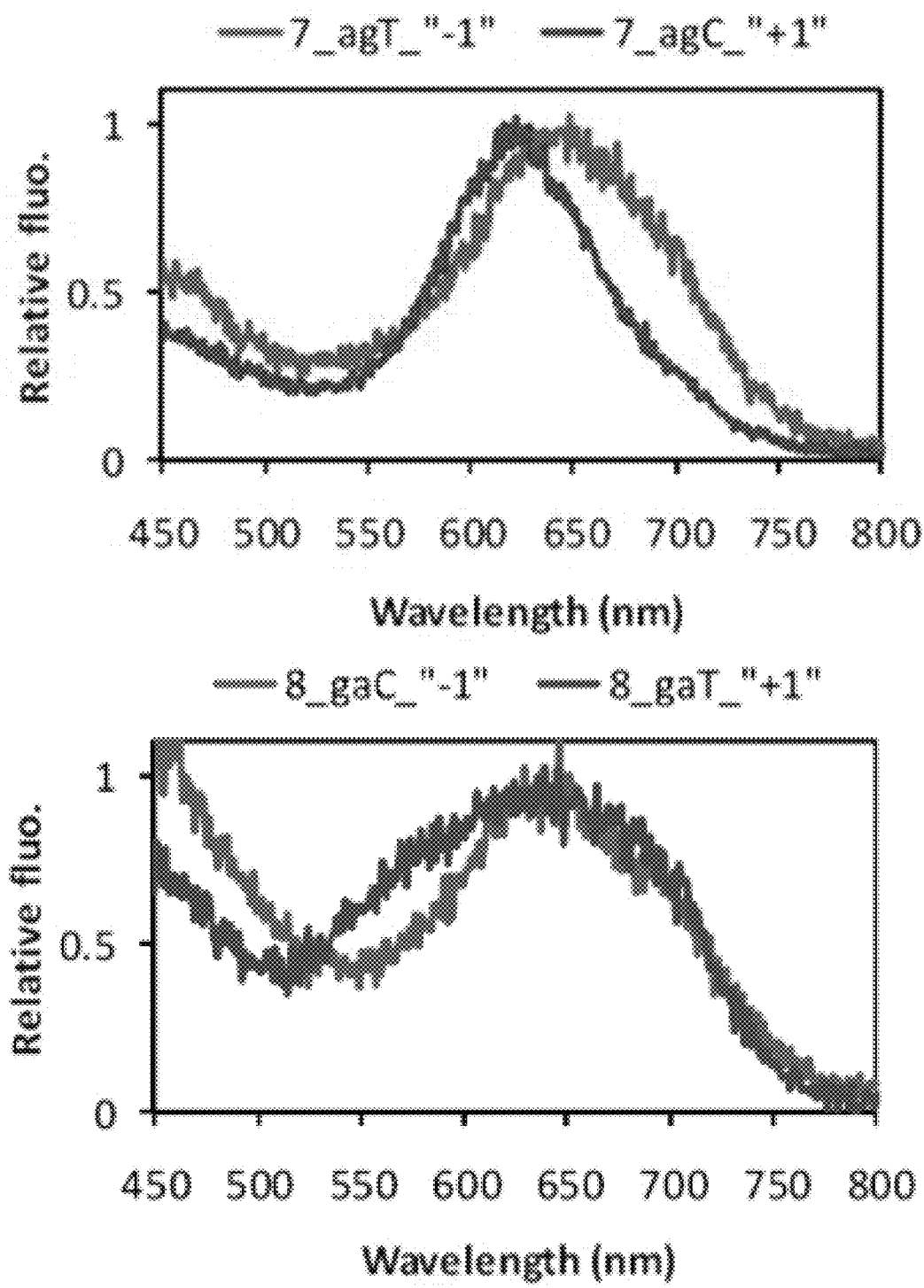

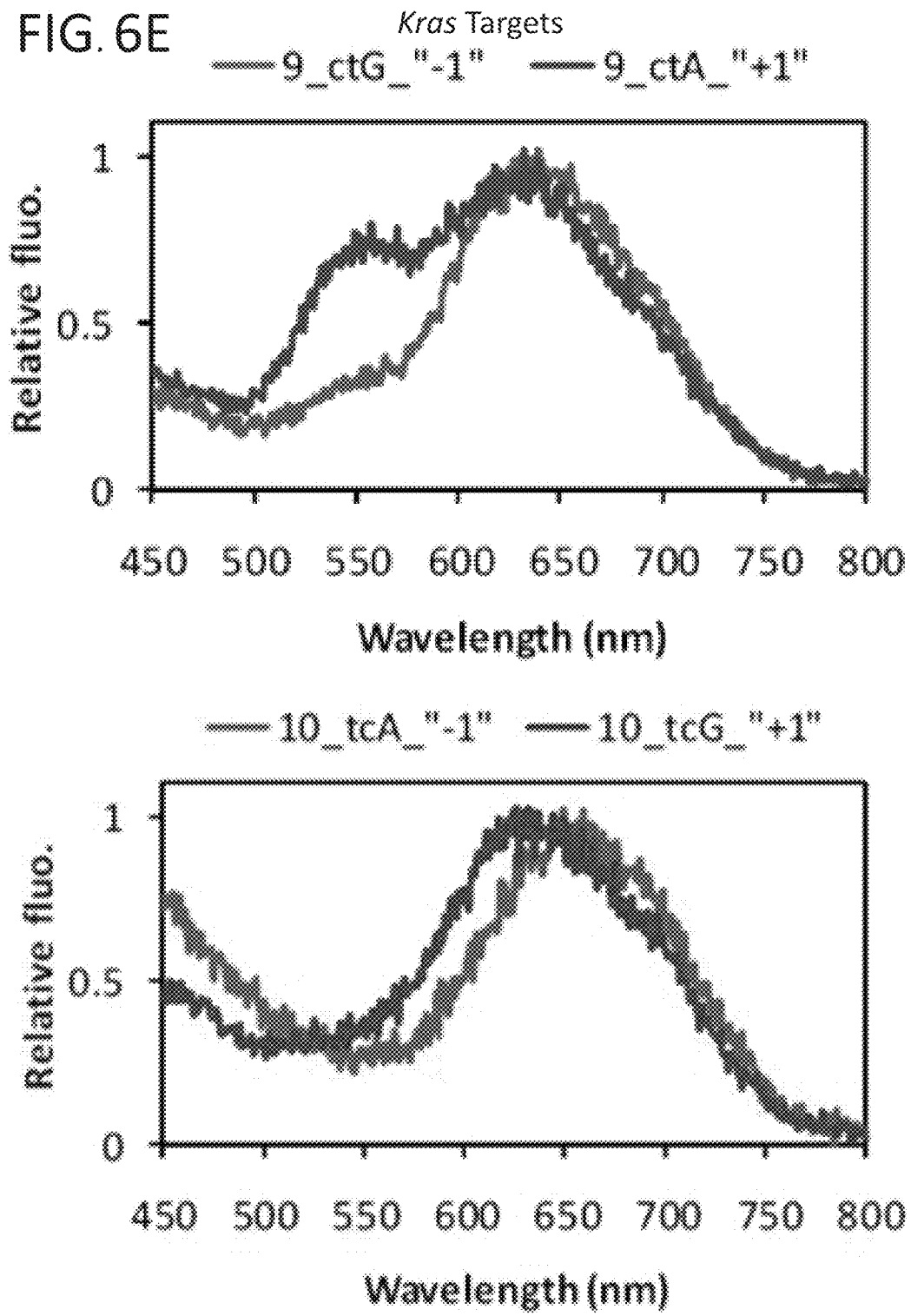

FIG. 7A     *Braf* Targets
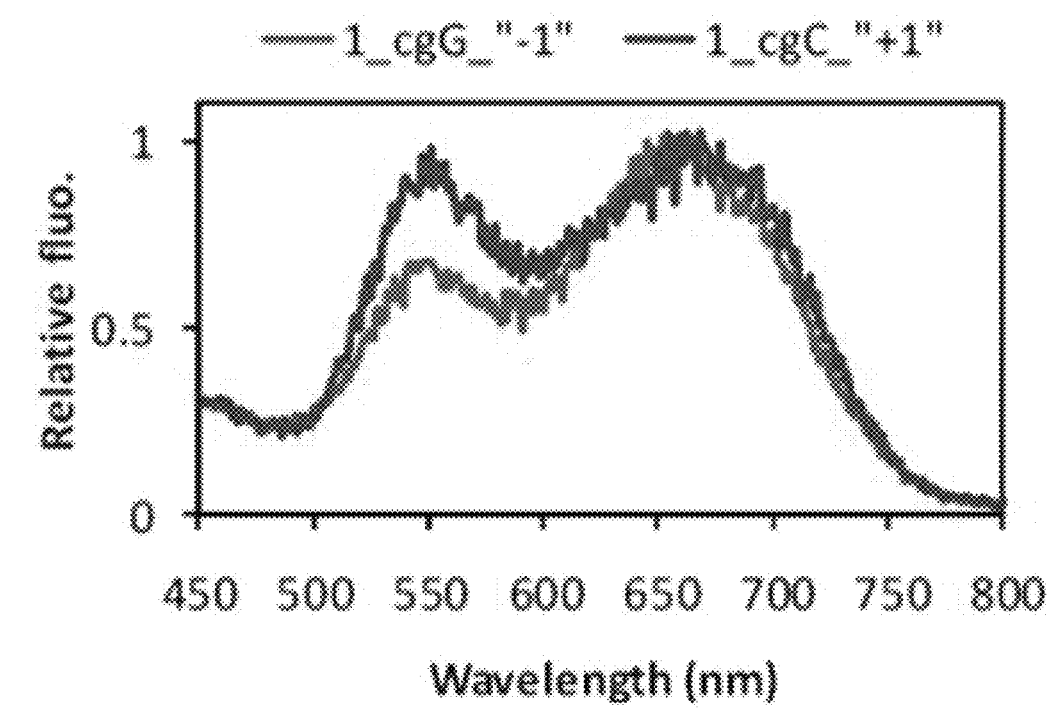
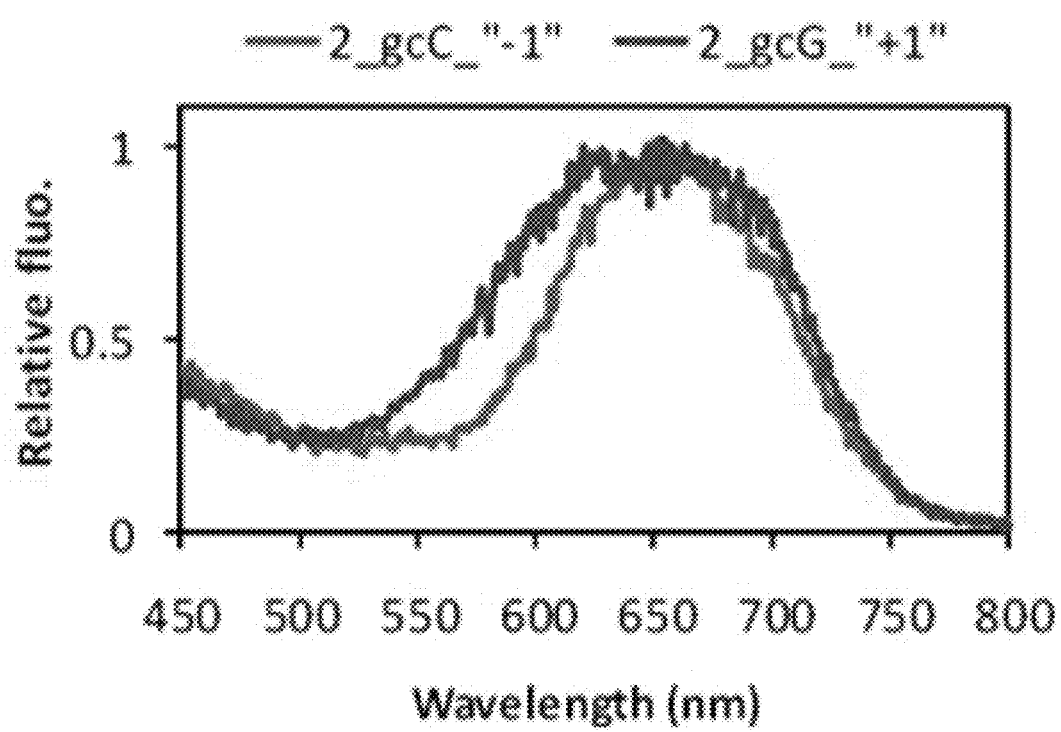

FIG. 7B  *Braf* Targets
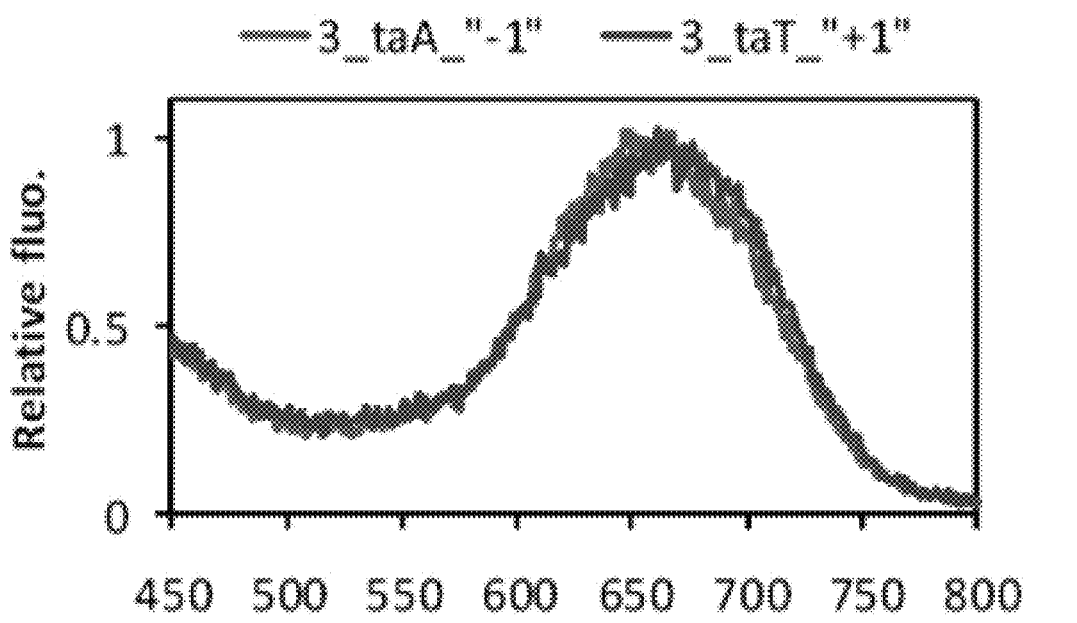
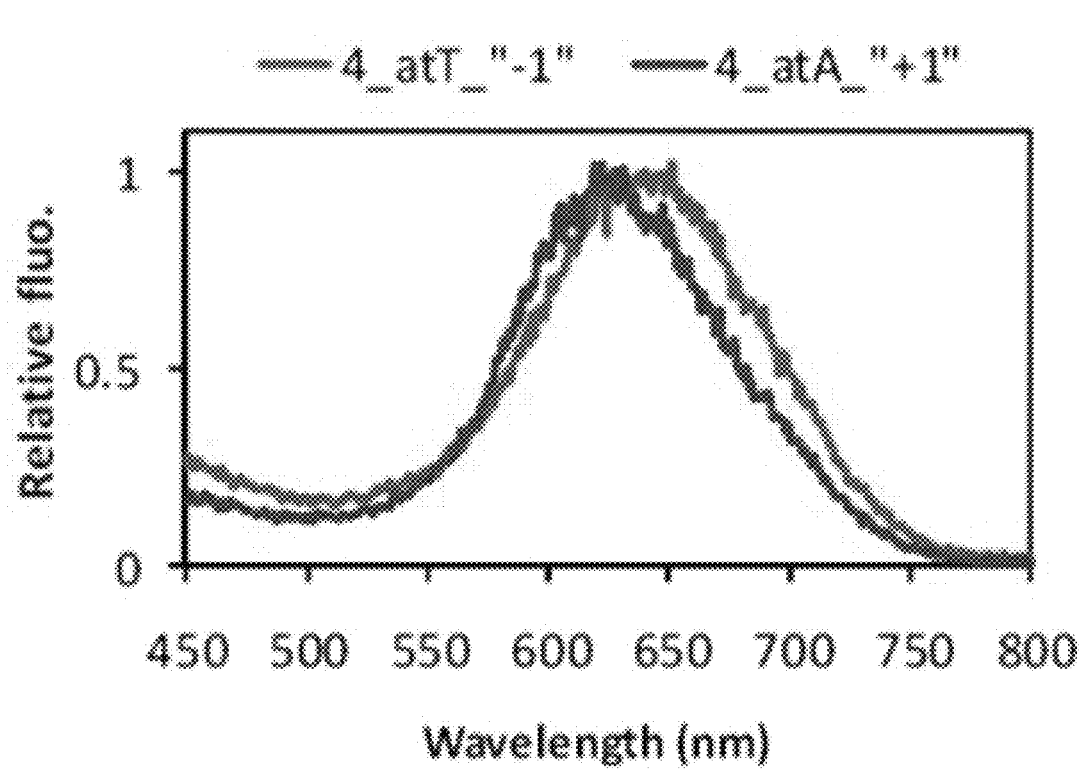

FIG. 7C  *Braf* Targets
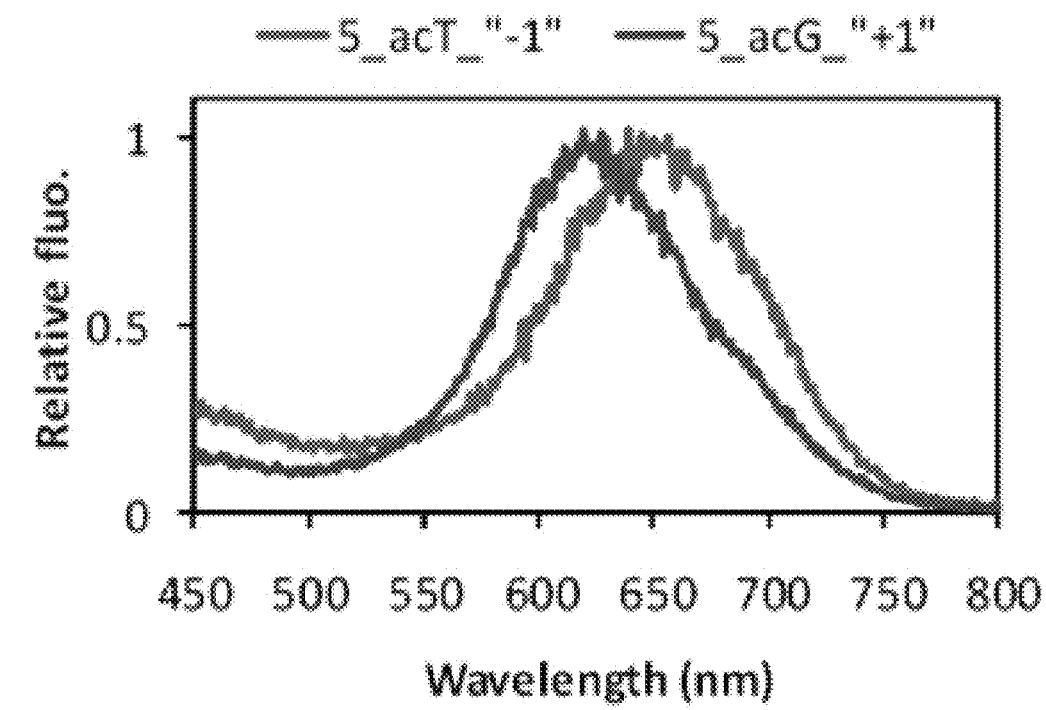
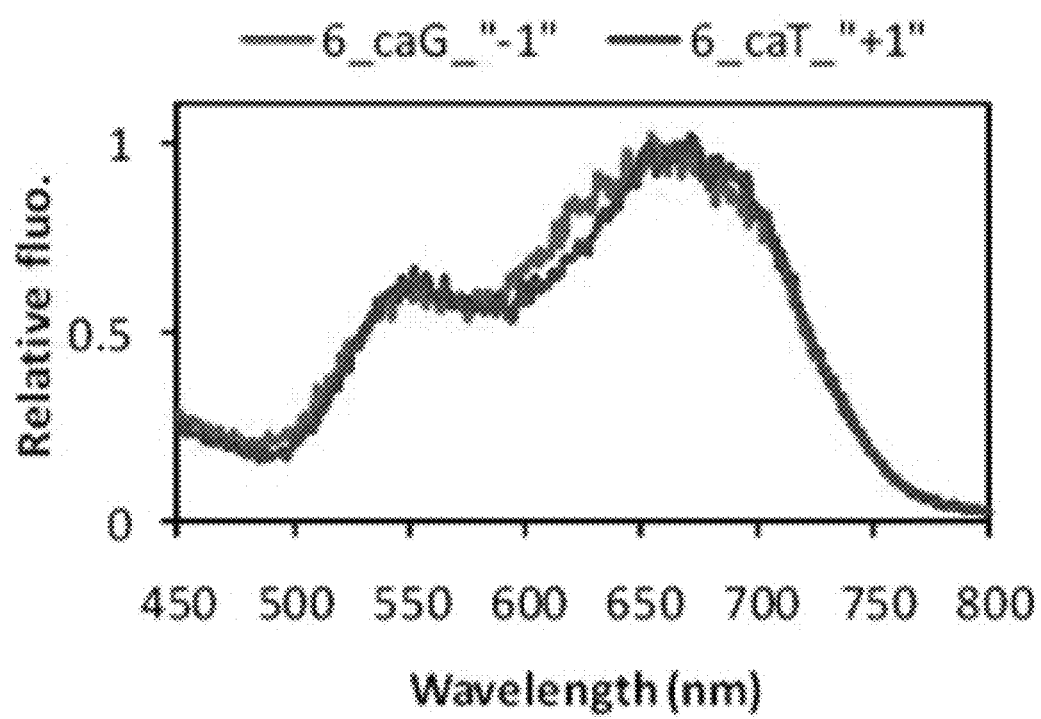

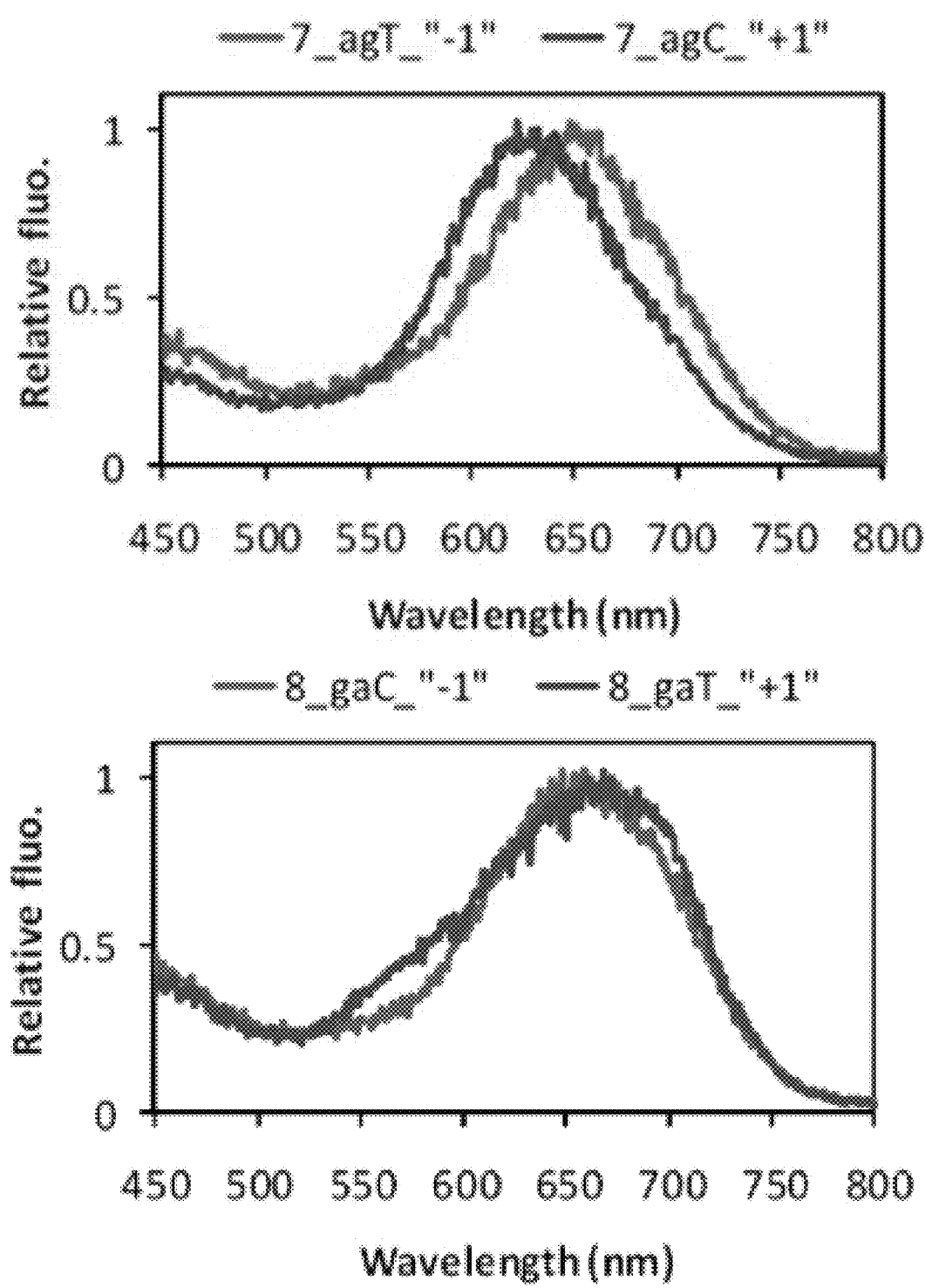
FIG. 7D  *Braf* Targets

FIG. 8A  Sickle cell anemia Targets
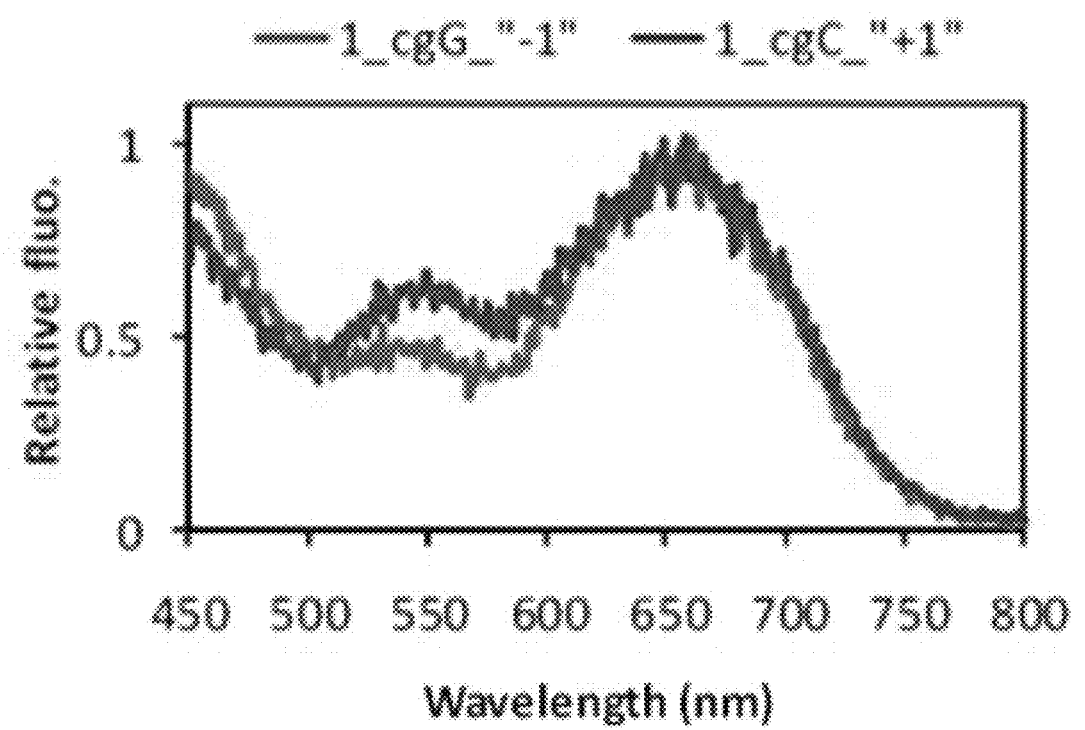
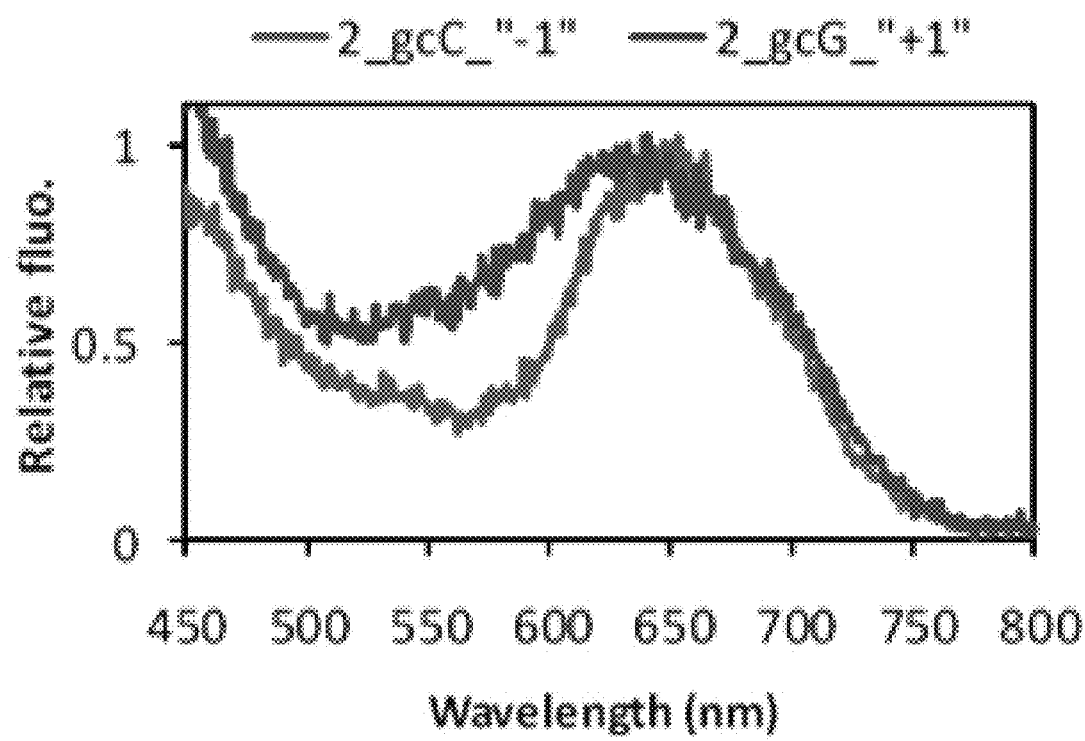

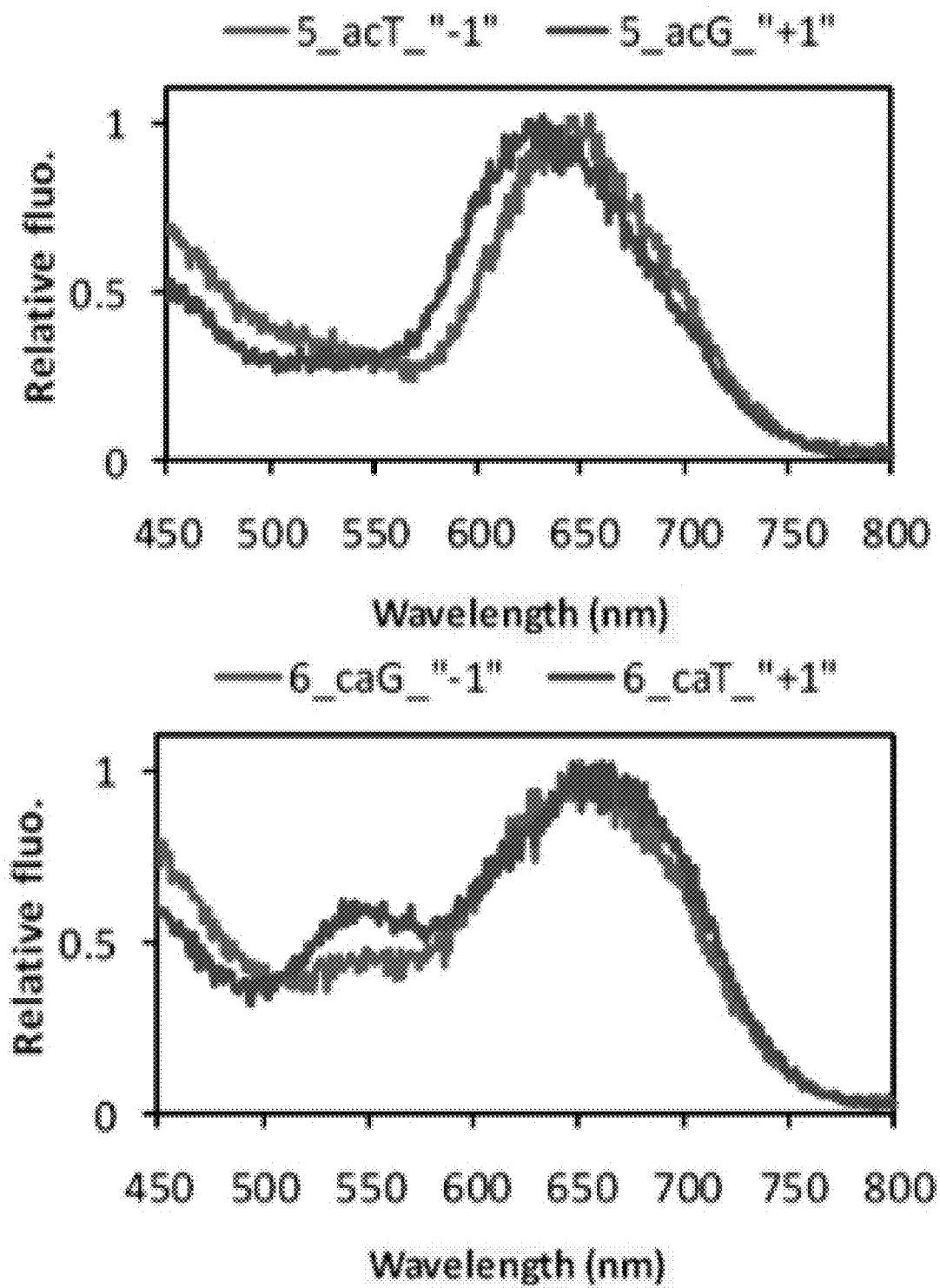

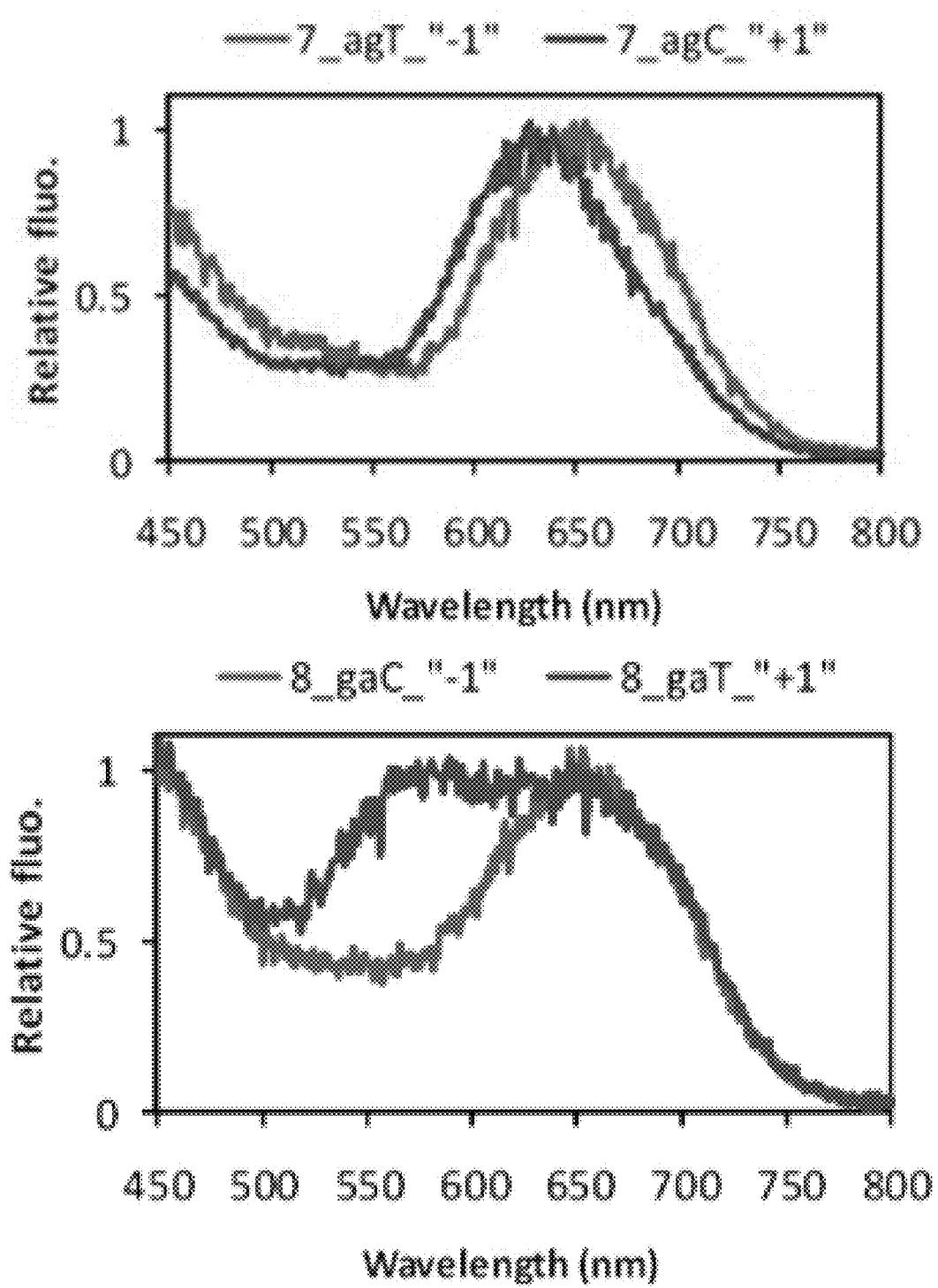
FIG. 8D  Sickle cell anemia Targets

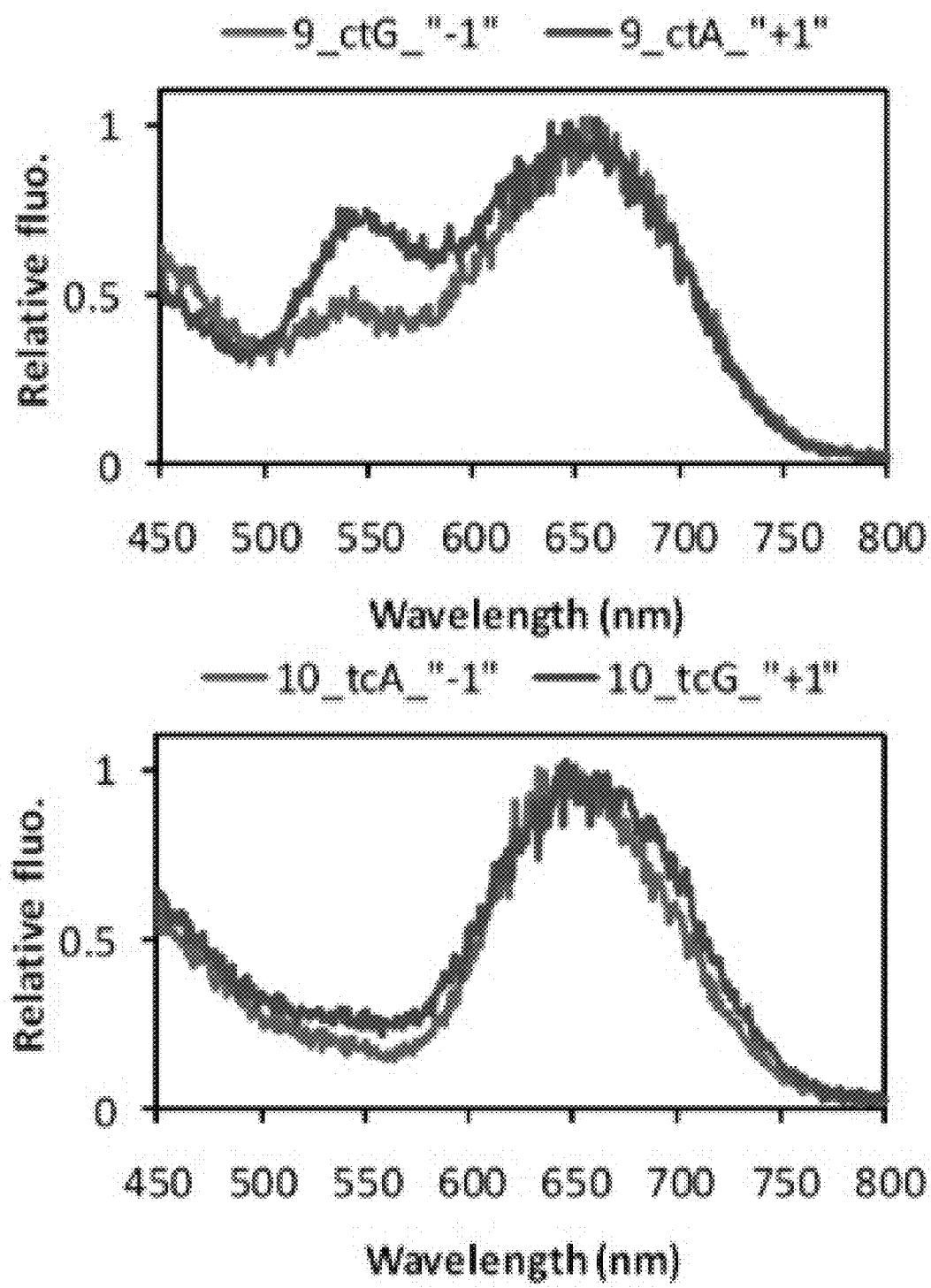

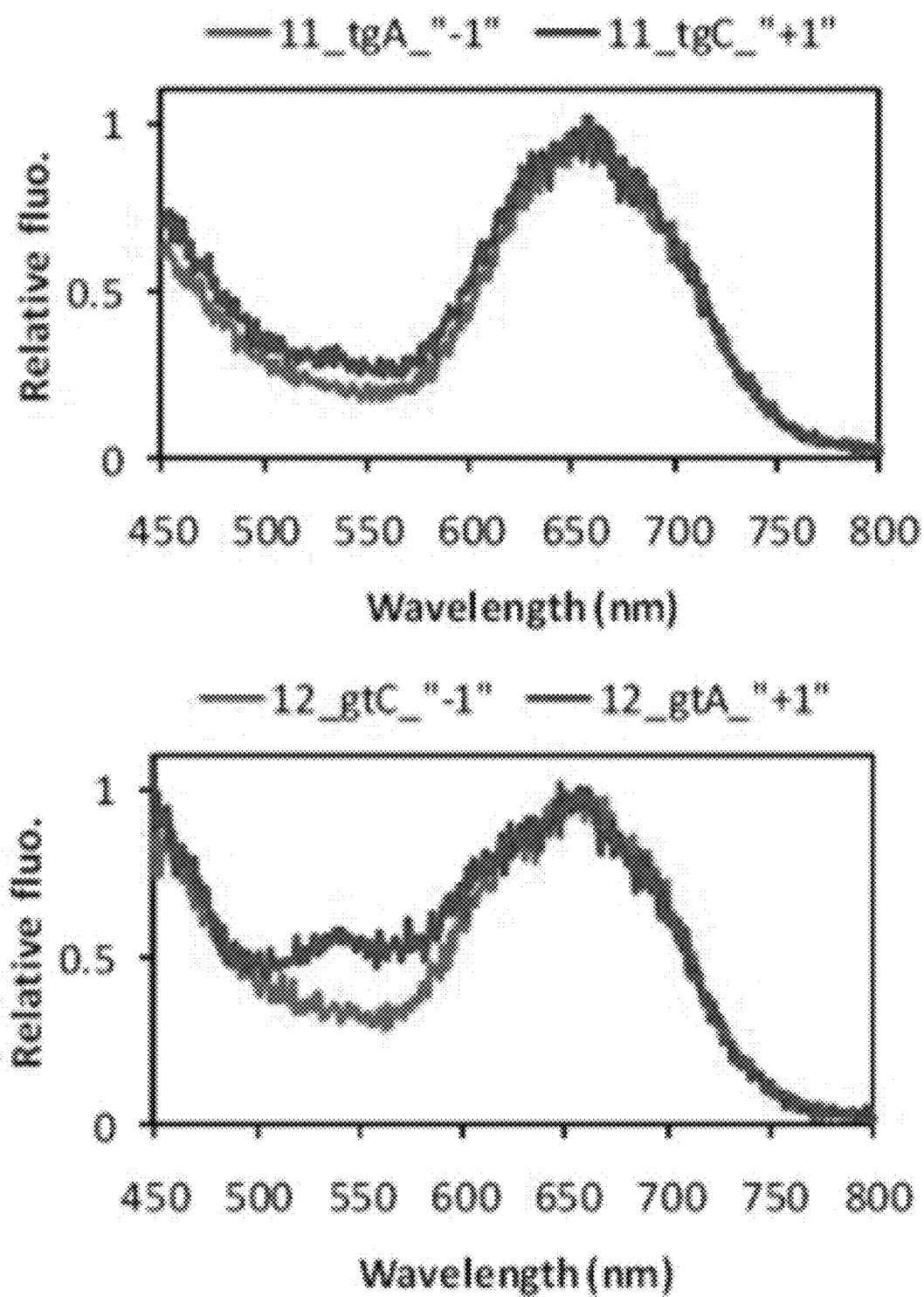
FIG. 8F  Sickle cell anemia Targets

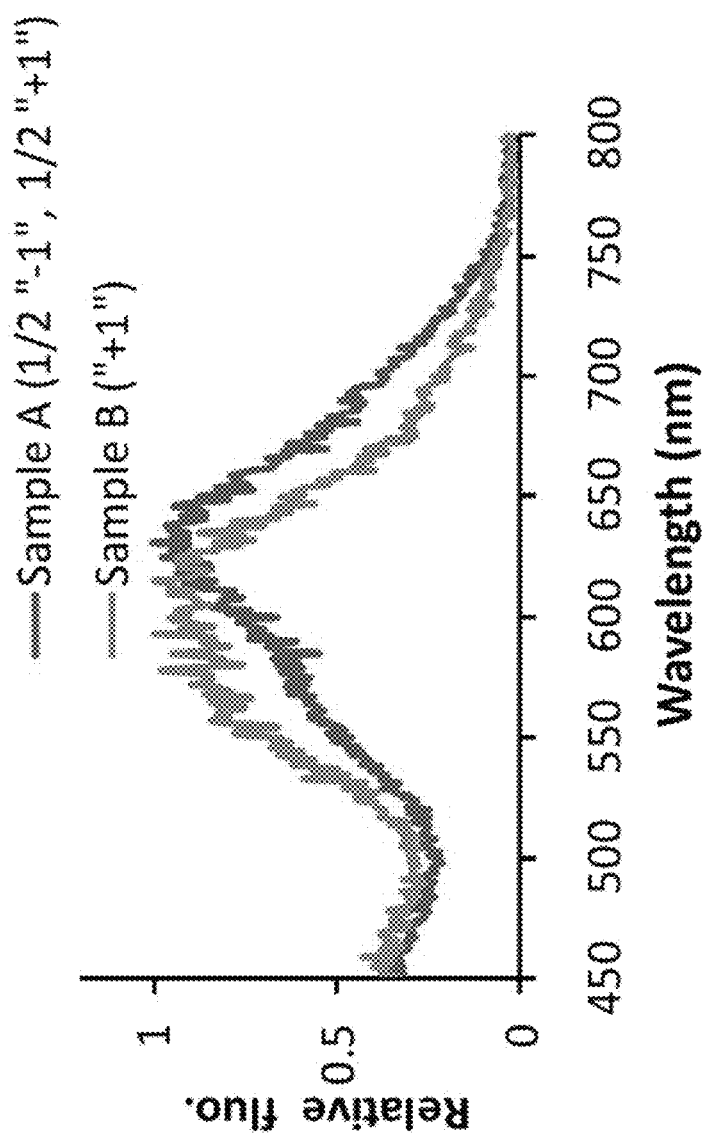
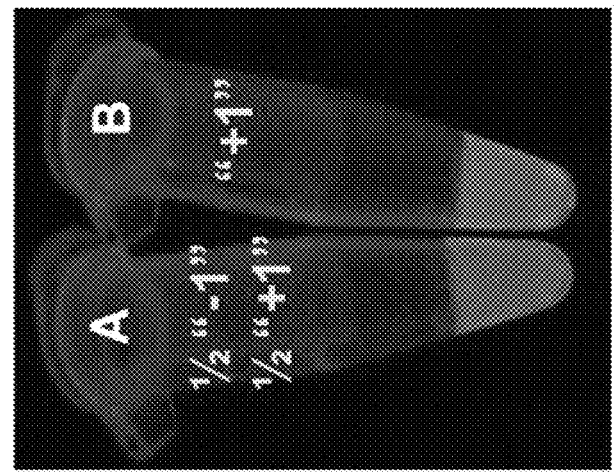
FIG. 9B
FIG. 9A

SEQUENCE LISTING

```
<160> NUMBER OF SEQ ID NOS: 92

<210> SEQ ID NO 1
<211> LENGTH: 42
<212> TYPE: DNA
<213> ORGANISM: artificial sequence
<220> FEATURE:
<223> OTHER INFORMATION: probe

<400> SEQUENCE: 1
cccttaatcc cctataataa attttaaata ttatttatta at                    42

<210> SEQ ID NO 2
<211> LENGTH: 30
<212> TYPE: DNA
<213> ORGANISM: artificial sequence
<220> FEATURE:
<223> OTHER INFORMATION: probe
```

<400> SEQUENCE: 2
tataataaat tttaaatatt atttattaat                     30

<210> SEQ ID NO 3
<211> LENGTH: 12
<212> TYPE: DNA
<213> ORGANISM: artificial sequence
<220> FEATURE:
<223> OTHER INFORMATION: probe

<400> SEQUENCE: 3
cccttaatcc cc                                        12

<210> SEQ ID NO 4
<211> LENGTH: 18
<212> TYPE: DNA
<213> ORGANISM: artificial sequence
<220> FEATURE:
<223> OTHER INFORMATION: probe

<400> SEQUENCE: 4
gggtggggtg gggtgggg                                  18

<210> SEQ ID NO 5
<211> LENGTH: 51
<212> TYPE: DNA
<213> ORGANISM: artificial sequence
<220> FEATURE:
<223> OTHER INFORMATION: probe

<400> SEQUENCE: 5
attaataaat aatatttaaa atttattata atagggtggg gtggggtggg g    51

<210> SEQ ID NO 6
<211> LENGTH: 50
<212> TYPE: DNA
<213> ORGANISM: artificial sequence
<220> FEATURE:
<223> OTHER INFORMATION: probe

<400> SEQUENCE: 6
attaataaat aatatttaaa atttattata tagggtgggg tggggtgggg       50

<210> SEQ ID NO 7
<211> LENGTH: 49
<212> TYPE: DNA
<213> ORGANISM: artificial sequence
<220> FEATURE:
<223> OTHER INFORMATION: probe

<400> SEQUENCE: 7
attaataaat aatatttaaa atttattata agggtgggt ggggtgggg         49

<210> SEQ ID NO 8
<211> LENGTH: 48
<212> TYPE: DNA
<213> ORGANISM: artificial sequence
<220> FEATURE:
<223> OTHER INFORMATION: probe

<400> SEQUENCE: 8
attaataaat aatatttaaa atttattata gggtggggtg gggtgggg         48

<210> SEQ ID NO 9

```
<211> LENGTH: 47
<212> TYPE: DNA
<213> ORGANISM: artificial sequence
<220> FEATURE:
<223> OTHER INFORMATION: probe

<400> SEQUENCE: 9
attaataaat aatatttaaa atttattatg ggtggggtgg ggtgggg         47

<210> SEQ ID NO 10
<211> LENGTH: 46
<212> TYPE: DNA
<213> ORGANISM: artificial sequence
<220> FEATURE:
<223> OTHER INFORMATION: probe

<400> SEQUENCE: 10
attaataaat aatatttaaa atttattagg gtggggtggg gtgggg          46

<210> SEQ ID NO 11
<211> LENGTH: 45
<212> TYPE: DNA
<213> ORGANISM: artificial sequence
<220> FEATURE:
<223> OTHER INFORMATION: probe

<400> SEQUENCE: 11
attaataaat aatatttaaa atttattggg tggggtgggg tgggg           45

<210> SEQ ID NO 12
<211> LENGTH: 44
<212> TYPE: DNA
<213> ORGANISM: artificial sequence
<220> FEATURE:
<223> OTHER INFORMATION: probe

<400> SEQUENCE: 12
attaataaat aatatttaaa atttatgggt ggggtggggt gggg            44

<210> SEQ ID NO 13
<211> LENGTH: 43
<212> TYPE: DNA
<213> ORGANISM: artificial sequence
<220> FEATURE:
<223> OTHER INFORMATION: probe

<400> SEQUENCE: 13
attaataaat aatatttaaa atttagggtg gggtggggtg ggg             43

<210> SEQ ID NO 14
<211> LENGTH: 42
<212> TYPE: DNA
<213> ORGANISM: artificial sequence
<220> FEATURE:
<223> OTHER INFORMATION: probe

<400> SEQUENCE: 14
attaataaat aatatttaaa atttgggtgg ggtggggtgg gg              42

<210> SEQ ID NO 15
<211> LENGTH: 41
<212> TYPE: DNA
<213> ORGANISM: artificial sequence
<220> FEATURE:
<223> OTHER INFORMATION: probe

<400> SEQUENCE: 15
```

```
attaataaat aatatttaaa attgggtggg gtggggtggg g                    41

<210> SEQ ID NO 16
<211> LENGTH: 40
<212> TYPE: DNA
<213> ORGANISM: artificial sequence
<220> FEATURE:
<223> OTHER INFORMATION: probe

<400> SEQUENCE: 16
cccttaatcc ccgagacagc tccaactacc acaagtttat                      40

<210> SEQ ID NO 17
<211> LENGTH: 41
<212> TYPE: DNA
<213> ORGANISM: artificial sequence
<220> FEATURE:
<223> OTHER INFORMATION: probe

<400> SEQUENCE: 17
cccttaatcc cctgagacag ctccaactac acaagtttta t                    41

<210> SEQ ID NO 18
<211> LENGTH: 45
<212> TYPE: DNA
<213> ORGANISM: artificial sequence
<220> FEATURE:
<223> OTHER INFORMATION: probe

<400> SEQUENCE: 18
tcaaggcact cttgcctacg ccactctggg tggggtgggg tgggg                45

<210> SEQ ID NO 19
<211> LENGTH: 60
<212> TYPE: DNA
<213> ORGANISM: homo sapiens

<400> SEQUENCE: 19
ctgaatataa acttgtggta gttggagctg gtggcgtagg caagagtgcc ttgacgatac  60

<210> SEQ ID NO 20
<211> LENGTH: 60
<212> TYPE: DNA
<213> ORGANISM: homo sapiens

<400> SEQUENCE: 20
ctgaatataa acttgtggta gttggagctg ttggcgtagg caagagtgcc ttgacgatac  60

<210> SEQ ID NO 21
<211> LENGTH: 60
<212> TYPE: DNA
<213> ORGANISM: homo sapiens

<400> SEQUENCE: 21
ctgaatataa acttgtggta gttggagctg ctggcgtagg caagagtgcc ttgacgatac  60

<210> SEQ ID NO 22
<211> LENGTH: 60
<212> TYPE: DNA
<213> ORGANISM: homo sapiens

<400> SEQUENCE: 22
ctgaatataa acttgtggta gttggagctg atggcgtagg caagagtgcc ttgacgatac  60
```

<210> SEQ ID NO 23
<211> LENGTH: 37
<212> TYPE: DNA
<213> ORGANISM: artificial sequence
<220> FEATURE:
<223> OTHER INFORMATION: probe

<400> SEQUENCE: 23
cccttaatcc ccgcagctcc aactaccaca agtttat                              37

<210> SEQ ID NO 24
<211> LENGTH: 37
<212> TYPE: DNA
<213> ORGANISM: artificial sequence
<220> FEATURE:
<223> OTHER INFORMATION: probe

<400> SEQUENCE: 24
cccttaatcc cctcagctcc aactaccaca agtttat                              37

<210> SEQ ID NO 25
<211> LENGTH: 37
<212> TYPE: DNA
<213> ORGANISM: artificial sequence
<220> FEATURE:
<223> OTHER INFORMATION: probe

<400> SEQUENCE: 25
cccttaatcc ccccagctcc aactaccaca agtttat                              37

<210> SEQ ID NO 26
<211> LENGTH: 37
<212> TYPE: DNA
<213> ORGANISM: artificial sequence
<220> FEATURE:
<223> OTHER INFORMATION: probe

<400> SEQUENCE: 26
cccttaatcc ccacagctcc aactaccaca agtttat                              37

<210> SEQ ID NO 27
<211> LENGTH: 42
<212> TYPE: DNA
<213> ORGANISM: artificial sequence
<220> FEATURE:
<223> OTHER INFORMATION: probe

<400> SEQUENCE: 27
tcaaggcact cttgcctacg ccaggggtgg ggtgggggtgg gg                       42

<210> SEQ ID NO 28
<211> LENGTH: 42
<212> TYPE: DNA
<213> ORGANISM: artificial sequence
<220> FEATURE:
<223> OTHER INFORMATION: probe

<400> SEQUENCE: 28
tcaaggcact cttgcctacg ccatgggtgg ggtggggtgg gg                        42

<210> SEQ ID NO 29
<211> LENGTH: 42
<212> TYPE: DNA
<213> ORGANISM: artificial sequence
<220> FEATURE:
<223> OTHER INFORMATION: probe

<400> SEQUENCE: 29
tcaaggcact cttgcctacg ccacgggtgg ggtggggtgg gg                42

<210> SEQ ID NO 30
<211> LENGTH: 42
<212> TYPE: DNA
<213> ORGANISM: artificial sequence
<220> FEATURE:
<223> OTHER INFORMATION: probe

<400> SEQUENCE: 30
tcaaggcact cttgcctacg ccaagggtgg ggtggggtgg gg                42

<210> SEQ ID NO 31
<211> LENGTH: 60
<212> TYPE: DNA
<213> ORGANISM: artificial sequence
<220> FEATURE:
<223> OTHER INFORMATION: probe

<400> SEQUENCE: 31
taaaaatagg tgattttggt ctagctacag ggaaatctcg atggagtggg tcccatcagt    60

<210> SEQ ID NO 32
<211> LENGTH: 60
<212> TYPE: DNA
<213> ORGANISM: artificial sequence
<220> FEATURE:
<223> OTHER INFORMATION: probe

<400> SEQUENCE: 32
taaaaatagg tgattttggt ctagctacag tgaaatctcg atggagtggg tcccatcagt    60

<210> SEQ ID NO 33
<211> LENGTH: 60
<212> TYPE: DNA
<213> ORGANISM: artificial sequence
<220> FEATURE:
<223> OTHER INFORMATION: probe

<400> SEQUENCE: 33
taaaaatagg tgattttggt ctagctacag cgaaatctcg atggagtggg tcccatcagt    60

<210> SEQ ID NO 34
<211> LENGTH: 60
<212> TYPE: DNA
<213> ORGANISM: artificial sequence
<220> FEATURE:
<223> OTHER INFORMATION: probe

<400> SEQUENCE: 34
taaaaatagg tgattttggt ctagctacag agaaatctcg atggagtggg tcccatcagt    60

<210> SEQ ID NO 35
<211> LENGTH: 37
<212> TYPE: DNA
<213> ORGANISM: artificial sequence
<220> FEATURE:
<223> OTHER INFORMATION: probe

<400> SEQUENCE: 35
cccttaatcc ccgctgtagc tagaccaaaa tcaccta                      37

<210> SEQ ID NO 36

```
<211> LENGTH: 37
<212> TYPE: DNA
<213> ORGANISM: artificial sequence
<220> FEATURE:
<223> OTHER INFORMATION: probe

<400> SEQUENCE: 36
cccttaatcc cctctgtagc tagaccaaaa tcaccta                              37

<210> SEQ ID NO 37
<211> LENGTH: 37
<212> TYPE: DNA
<213> ORGANISM: artificial sequence
<220> FEATURE:
<223> OTHER INFORMATION: probe

<400> SEQUENCE: 37
cccttaatcc ccctgtagc tagaccaaaa tcaccta                               37

<210> SEQ ID NO 38
<211> LENGTH: 37
<212> TYPE: DNA
<213> ORGANISM: artificial sequence
<220> FEATURE:
<223> OTHER INFORMATION: probe

<400> SEQUENCE: 38
cccttaatcc ccactgtagc tagaccaaaa tcaccta                              37

<210> SEQ ID NO 39
<211> LENGTH: 42
<212> TYPE: DNA
<213> ORGANISM: artificial sequence
<220> FEATURE:
<223> OTHER INFORMATION: probe

<400> SEQUENCE: 39
gggacccact ccatcgagat ttcggggtgg ggtggggtgg gg                        42

<210> SEQ ID NO 40
<211> LENGTH: 42
<212> TYPE: DNA
<213> ORGANISM: artificial sequence
<220> FEATURE:
<223> OTHER INFORMATION: probe

<400> SEQUENCE: 40
gggacccact ccatcgagat ttctgggtgg ggtggggtgg gg                        42

<210> SEQ ID NO 41
<211> LENGTH: 42
<212> TYPE: DNA
<213> ORGANISM: artificial sequence
<220> FEATURE:
<223> OTHER INFORMATION: probe

<400> SEQUENCE: 41
gggacccact ccatcgagat ttccgggtgg ggtggggtgg gg                        42

<210> SEQ ID NO 42
<211> LENGTH: 42
<212> TYPE: DNA
<213> ORGANISM: artificial sequence
<220> FEATURE:
<223> OTHER INFORMATION: probe

<400> SEQUENCE: 42
```

```
gggacccact ccatcgagat ttcagggtgg ggtggggtgg gg                           42

<210> SEQ ID NO 43
<211> LENGTH: 60
<212> TYPE: DNA
<213> ORGANISM: artificial sequence
<220> FEATURE:
<223> OTHER INFORMATION: probe

<400> SEQUENCE: 43
aaacagacac catggtgcac ctgactcctg gggagaagtc tgccgttact gccctgtggg       60

<210> SEQ ID NO 44
<211> LENGTH: 60
<212> TYPE: DNA
<213> ORGANISM: artificial sequence
<220> FEATURE:
<223> OTHER INFORMATION: probe

<400> SEQUENCE: 44
aaacagacac catggtgcac ctgactcctg tggagaagtc tgccgttact gccctgtggg       60

<210> SEQ ID NO 45
<211> LENGTH: 60
<212> TYPE: DNA
<213> ORGANISM: artificial sequence
<220> FEATURE:
<223> OTHER INFORMATION: probe

<400> SEQUENCE: 45
aaacagacac catggtgcac ctgactcctg cggagaagtc tgccgttact gccctgtggg       60

<210> SEQ ID NO 46
<211> LENGTH: 60
<212> TYPE: DNA
<213> ORGANISM: artificial sequence
<220> FEATURE:
<223> OTHER INFORMATION: probe

<400> SEQUENCE: 46
aaacagacac catggtgcac ctgactcctg aggagaagtc tgccgttact gccctgtggg       60

<210> SEQ ID NO 47
<211> LENGTH: 37
<212> TYPE: DNA
<213> ORGANISM: artificial sequence
<220> FEATURE:
<223> OTHER INFORMATION: probe

<400> SEQUENCE: 47
cccttaatcc ccgcaggagt caggtgcacc atggtgt                                37

<210> SEQ ID NO 48
<211> LENGTH: 37
<212> TYPE: DNA
<213> ORGANISM: artificial sequence
<220> FEATURE:
<223> OTHER INFORMATION: probe

<400> SEQUENCE: 48
cccttaatcc cctcaggagt caggtgcacc atggtgt                                37

<210> SEQ ID NO 49
<211> LENGTH: 37
<212> TYPE: DNA
```

<213> ORGANISM: artificial sequence
<220> FEATURE:
<223> OTHER INFORMATION: probe

<400> SEQUENCE: 49
cccttaatcc ccccaggagt caggtgcacc atggtgt    37

<210> SEQ ID NO 50
<211> LENGTH: 37
<212> TYPE: DNA
<213> ORGANISM: artificial sequence
<220> FEATURE:
<223> OTHER INFORMATION: probe

<400> SEQUENCE: 50
cccttaatcc ccacaggagt caggtgcacc atggtgt    37

<210> SEQ ID NO 51
<211> LENGTH: 42
<212> TYPE: DNA
<213> ORGANISM: artificial sequence
<220> FEATURE:
<223> OTHER INFORMATION: probe

<400> SEQUENCE: 51
gggcagtaac ggcagacttc tccggggtgg ggtggggtgg gg    42

<210> SEQ ID NO 52
<211> LENGTH: 42
<212> TYPE: DNA
<213> ORGANISM: artificial sequence
<220> FEATURE:
<223> OTHER INFORMATION: probe

<400> SEQUENCE: 52
gggcagtaac ggcagacttc tcctgggtgg ggtggggtgg gg    42

<210> SEQ ID NO 53
<211> LENGTH: 42
<212> TYPE: DNA
<213> ORGANISM: artificial sequence
<220> FEATURE:
<223> OTHER INFORMATION: probe

<400> SEQUENCE: 53
gggcagtaac ggcagacttc tcccgggtgg ggtggggtgg gg    42

<210> SEQ ID NO 54
<211> LENGTH: 42
<212> TYPE: DNA
<213> ORGANISM: artificial sequence
<220> FEATURE:
<223> OTHER INFORMATION: probe

<400> SEQUENCE: 54
gggcagtaac ggcagacttc tccagggtgg ggtggggtgg gg    42

<210> SEQ ID NO 55
<211> LENGTH: 40
<212> TYPE: DNA
<213> ORGANISM: artificial sequence
<220> FEATURE:
<223> OTHER INFORMATION: probe

<400> SEQUENCE: 55
cccttaatcc ccgtgtcagc tccaactacc acaagtttat    40

<210> SEQ ID NO 56
<211> LENGTH: 45
<212> TYPE: DNA
<213> ORGANISM: artificial sequence
<220> FEATURE:
<223> OTHER INFORMATION: probe

<400> SEQUENCE: 56
tcaaggcact cttgcctacg ccacacaggg tggggtgggg tgggg                45

<210> SEQ ID NO 57
<211> LENGTH: 48
<212> TYPE: DNA
<213> ORGANISM: artificial sequence
<220> FEATURE:
<223> OTHER INFORMATION: probe

<400> SEQUENCE: 57
attaataaat aatatttaaa atttattata ttggttggtt ggttggtt             48

<210> SEQ ID NO 58
<211> LENGTH: 41
<212> TYPE: DNA
<213> ORGANISM: artificial sequence
<220> FEATURE:
<223> OTHER INFORMATION: probe

<400> SEQUENCE: 58
cccttaatcc ccataataaa ttttaaatat tatttattaa t                    41

<210> SEQ ID NO 59
<211> LENGTH: 42
<212> TYPE: DNA
<213> ORGANISM: artificial sequence
<220> FEATURE:
<223> OTHER INFORMATION: probe

<400> SEQUENCE: 59
cccttaatcc cctataataa attttaaata ttatttatta at                   42

<210> SEQ ID NO 60
<211> LENGTH: 43
<212> TYPE: DNA
<213> ORGANISM: artificial sequence
<220> FEATURE:
<223> OTHER INFORMATION: probe

<400> SEQUENCE: 60
cccttaatcc cctataata aattttaaat attatttatt aat                   43

<210> SEQ ID NO 61
<211> LENGTH: 44
<212> TYPE: DNA
<213> ORGANISM: artificial sequence
<220> FEATURE:
<223> OTHER INFORMATION: probe

<400> SEQUENCE: 61
cccttaatcc cctttataat aaattttaaa tattatttat taat                 44

<210> SEQ ID NO 62
<211> LENGTH: 45
<212> TYPE: DNA
<213> ORGANISM: artificial sequence
<220> FEATURE:

<223> OTHER INFORMATION: probe

<400> SEQUENCE: 62
cccttaatcc cctttttataa taaattttaa atattattta ttaat    45

<210> SEQ ID NO 63
<211> LENGTH: 60
<212> TYPE: DNA
<213> ORGANISM: artificial sequence
<220> FEATURE:
<223> OTHER INFORMATION: probe

<400> SEQUENCE: 63
gcatttgaag gtaccctga gcagaaggct ctggtgattg gtggagaggc ttgtatgtgg    60

<210> SEQ ID NO 64
<211> LENGTH: 60
<212> TYPE: DNA
<213> ORGANISM: artificial sequence
<220> FEATURE:
<223> OTHER INFORMATION: probe

<400> SEQUENCE: 64
gcatttgaag gtaccctga gcagaaggct gtggtgattg gtggagaggc ttgtatgtgg    60

<210> SEQ ID NO 65
<211> LENGTH: 37
<212> TYPE: DNA
<213> ORGANISM: artificial sequence
<220> FEATURE:
<223> OTHER INFORMATION: probe

<400> SEQUENCE: 65
cccttaatcc cccagccttc tgctcagggg taccttc    37

<210> SEQ ID NO 66
<211> LENGTH: 42
<212> TYPE: DNA
<213> ORGANISM: artificial sequence
<220> FEATURE:
<223> OTHER INFORMATION: probe

<400> SEQUENCE: 66
acaagcctct ccaccaatca ccaggggtgg ggtggggtgg gg    42

<210> SEQ ID NO 67
<211> LENGTH: 60
<212> TYPE: DNA
<213> ORGANISM: homo sapiens

<400> SEQUENCE: 67
agtcacagca catgacggag gttgtgaggc gctgccccca ccatgagcgc tgctcagata    60

<210> SEQ ID NO 68
<211> LENGTH: 60
<212> TYPE: DNA
<213> ORGANISM: homo sapiens

<400> SEQUENCE: 68
agtcacagca catgacggag gttgtgaggc actgccccca ccatgagcgc tgctcagata    60

<210> SEQ ID NO 69
<211> LENGTH: 37
<212> TYPE: DNA
<213> ORGANISM: artificial sequence
<220> FEATURE:
<223> OTHER INFORMATION: probe

<400> SEQUENCE: 69
cccttaatcc cccgcctcac aacctccgtc atgtgct                    37

<210> SEQ ID NO 70
<211> LENGTH: 42
<212> TYPE: DNA
<213> ORGANISM: artificial sequence
<220> FEATURE:
<223> OTHER INFORMATION: probe

<400> SEQUENCE: 70
agcagcgctc atggtggggg cagtgggtgg ggtggggtgg gg              42

<210> SEQ ID NO 71
<211> LENGTH: 60
<212> TYPE: DNA
<213> ORGANISM: homo sapiens

<400> SEQUENCE: 71
ggagaagatg tacttggaaa taaagtggaa cgaaaagaag atggatttga agatggagta   60

<210> SEQ ID NO 72
<211> LENGTH: 60
<212> TYPE: DNA
<213> ORGANISM: homo sapiens

<400> SEQUENCE: 72
ggagaagatg tacttggaaa taaagtggaa tgaaaagaag atggatttga agatggagta   60

<210> SEQ ID NO 73
<211> LENGTH: 37
<212> TYPE: DNA
<213> ORGANISM: artificial sequence
<220> FEATURE:
<223> OTHER INFORMATION: probe

<400> SEQUENCE: 73
cccttaatcc ccattccact ttatttccaa gtacatc                    37

<210> SEQ ID NO 74
<211> LENGTH: 42
<212> TYPE: DNA
<213> ORGANISM: artificial sequence
<220> FEATURE:
<223> OTHER INFORMATION: probe

<400> SEQUENCE: 74
atcttcaaat ccatcttctt ttcggggtgg ggtggggtgg gg              42

<210> SEQ ID NO 75
<211> LENGTH: 60
<212> TYPE: DNA
<213> ORGANISM: homo sapiens

<400> SEQUENCE: 75
ttctaggttc cttgcgactg ctgtgaattt tgtgatgcac ttggatagtc tctgttactc   60

<210> SEQ ID NO 76
<211> LENGTH: 60
<212> TYPE: DNA
<213> ORGANISM: homo sapiens

```
<400> SEQUENCE: 76
ttctaggttc cttgcgactg ctgtgaattt agtgatgcac ttggatagtc tctgttactc      60

<210> SEQ ID NO 77
<211> LENGTH: 37
<212> TYPE: DNA
<213> ORGANISM: artificial sequence
<220> FEATURE:
<223> OTHER INFORMATION: probe

<400> SEQUENCE: 77
cccttaatcc ccaaaattca cagcagtcgc aaggaac                               37

<210> SEQ ID NO 78
<211> LENGTH: 42
<212> TYPE: DNA
<213> ORGANISM: artificial sequence
<220> FEATURE:
<223> OTHER INFORMATION: probe

<400> SEQUENCE: 78
cagagactat ccaagtgcat cactgggtgg ggtggggtgg gg                         42

<210> SEQ ID NO 79
<211> LENGTH: 60
<212> TYPE: DNA
<213> ORGANISM: homo sapiens

<400> SEQUENCE: 79
tgagctgccc aggaatatcc aggcaagaat gaccatattc tgataattac tcaggcctct      60

<210> SEQ ID NO 80
<211> LENGTH: 60
<212> TYPE: DNA
<213> ORGANISM: homo sapiens

<400> SEQUENCE: 80
tgagctgccc aggaatatcc aggcaagaat taccatattc tgataattac tcaggcctct      60

<210> SEQ ID NO 81
<211> LENGTH: 37
<212> TYPE: DNA
<213> ORGANISM: artificial sequence
<220> FEATURE:
<223> OTHER INFORMATION: probe

<400> SEQUENCE: 81
cccttaatcc ccaattcttg cctggatatt cctgggc                               37

<210> SEQ ID NO 82
<211> LENGTH: 42
<212> TYPE: DNA
<213> ORGANISM: artificial sequence
<220> FEATURE:
<223> OTHER INFORMATION: probe

<400> SEQUENCE: 82
ctgagtaatt atcagaatat ggtcgggtgg ggtggggtgg gg                         42

<210> SEQ ID NO 83
<211> LENGTH: 50
<212> TYPE: DNA
<213> ORGANISM: artificial sequence
<220> FEATURE:
<223> OTHER INFORMATION: probe
```

```
<220> FEATURE:
<221> NAME/KEY: misc_feature
<222> LOCATION: (6)..(10)
<223> OTHER INFORMATION: ggggt or no nucleotides
<220> FEATURE:
<221> NAME/KEY: misc_feature
<222> LOCATION: (11)..(15)
<223> OTHER INFORMATION: ggggt or no nucleotides
<220> FEATURE:
<221> NAME/KEY: misc_feature
<222> LOCATION: (16)..(20)
<223> OTHER INFORMATION: ggggt or no nucleotides
<220> FEATURE:
<221> NAME/KEY: misc_feature
<222> LOCATION: (21)..(25)
<223> OTHER INFORMATION: ggggt or no nucleotides
<220> FEATURE:
<221> NAME/KEY: misc_feature
<222> LOCATION: (26)..(30)
<223> OTHER INFORMATION: ggggt or no nucleotides
<220> FEATURE:
<221> NAME/KEY: misc_feature
<222> LOCATION: (31)..(35)
<223> OTHER INFORMATION: ggggt or no nucleotides
<220> FEATURE:
<221> NAME/KEY: misc_feature
<222> LOCATION: (36)..(40)
<223> OTHER INFORMATION: ggggt or no nucleotides
<220> FEATURE:
<221> NAME/KEY: misc_feature
<222> LOCATION: (41)..(45)
<223> OTHER INFORMATION: ggggt or no nucleotides
<220> FEATURE:
<221> NAME/KEY: misc_feature
<222> LOCATION: (46)..(50)
<223> OTHER INFORMATION: ggggt or no nucleotides

<400> SEQUENCE: 83
ggggtggggt ggggtggggt ggggtggggt ggggtggggt ggggtggggt          50

<210> SEQ ID NO 84
<211> LENGTH: 50
<212> TYPE: DNA
<213> ORGANISM: artificial sequence
<220> FEATURE:
<223> OTHER INFORMATION: probe
<220> FEATURE:
<221> NAME/KEY: misc_feature
<222> LOCATION: (6)..(10)
<223> OTHER INFORMATION: tgggg or no nucleotides
<220> FEATURE:
<221> NAME/KEY: misc_feature
<222> LOCATION: (11)..(15)
<223> OTHER INFORMATION: tgggg or no nucleotides
<220> FEATURE:
<221> NAME/KEY: misc_feature
<222> LOCATION: (16)..(20)
<223> OTHER INFORMATION: tgggg or no nucleotides
<220> FEATURE:
<221> NAME/KEY: misc_feature
<222> LOCATION: (21)..(25)
<223> OTHER INFORMATION: tgggg or no nucleotides
<220> FEATURE:
<221> NAME/KEY: misc_feature
<222> LOCATION: (26)..(30)
<223> OTHER INFORMATION: tgggg or no nucleotides
<220> FEATURE:
<221> NAME/KEY: misc_feature
<222> LOCATION: (31)..(35)
<223> OTHER INFORMATION: tgggg or no nucleotides
<220> FEATURE:
<221> NAME/KEY: misc_feature
<222> LOCATION: (36)..(40)
<223> OTHER INFORMATION: tgggg or no nucleotides
<220> FEATURE:
<221> NAME/KEY: misc_feature
<222> LOCATION: (41)..(45)
```

```
<223> OTHER INFORMATION: tgggg or no nucleotides
<220> FEATURE:
<221> NAME/KEY: misc_feature
<222> LOCATION: (46)..(50)
<223> OTHER INFORMATION: tgggg or no nucleotides

<400> SEQUENCE: 84
tggggtgggg tggggtgggg tggggtgggg tggggtgggg tggggtgggg          50

<210> SEQ ID NO 85
<211> LENGTH: 12
<212> TYPE: DNA
<213> ORGANISM: artificial sequence
<220> FEATURE:
<223> OTHER INFORMATION: probe

<400> SEQUENCE: 85
tttttttttt tt                                                    12

<210> SEQ ID NO 86
<211> LENGTH: 40
<212> TYPE: DNA
<213> ORGANISM: artificial sequence
<220> FEATURE:
<223> OTHER INFORMATION: probe
<220> FEATURE:
<221> NAME/KEY: misc_feature
<222> LOCATION: (5)..(8)
<223> OTHER INFORMATION: ggtt or no nucleotides
<220> FEATURE:
<221> NAME/KEY: misc_feature
<222> LOCATION: (9)..(12)
<223> OTHER INFORMATION: ggtt or no nucleotides
<220> FEATURE:
<221> NAME/KEY: misc_feature
<222> LOCATION: (13)..(16)
<223> OTHER INFORMATION: ggtt or no nucleotides
<220> FEATURE:
<221> NAME/KEY: misc_feature
<222> LOCATION: (17)..(20)
<223> OTHER INFORMATION: ggtt or no nucleotides
<220> FEATURE:
<221> NAME/KEY: misc_feature
<222> LOCATION: (21)..(24)
<223> OTHER INFORMATION: ggtt or no nucleotides
<220> FEATURE:
<221> NAME/KEY: misc_feature
<222> LOCATION: (25)..(28)
<223> OTHER INFORMATION: ggtt or no nucleotides
<220> FEATURE:
<221> NAME/KEY: misc_feature
<222> LOCATION: (29)..(32)
<223> OTHER INFORMATION: ggtt or no nucleotides
<220> FEATURE:
<221> NAME/KEY: misc_feature
<222> LOCATION: (33)..(36)
<223> OTHER INFORMATION: ggtt or no nucleotides
<220> FEATURE:
<221> NAME/KEY: misc_feature
<222> LOCATION: (37)..(40)
<223> OTHER INFORMATION: ggtt or no nucleotides

<400> SEQUENCE: 86
ggttggttgg ttggttggtt ggttggttgg ttggttggtt                      40

<210> SEQ ID NO 87
<211> LENGTH: 40
<212> TYPE: DNA
<213> ORGANISM: artificial sequence
<220> FEATURE:
<223> OTHER INFORMATION: probe
<220> FEATURE:
<221> NAME/KEY: MISC_FEATURE
```

```
<222> LOCATION: (5)..(8)
<223> OTHER INFORMATION: ttgg or no nucleotides
<220> FEATURE:
<221> NAME/KEY: MISC_FEATURE
<222> LOCATION: (9)..(12)
<223> OTHER INFORMATION: ttgg or no nucleotides
<220> FEATURE:
<221> NAME/KEY: MISC_FEATURE
<222> LOCATION: (13)..(16)
<223> OTHER INFORMATION: ttgg or no nucleotides
<220> FEATURE:
<221> NAME/KEY: MISC_FEATURE
<222> LOCATION: (17)..(20)
<223> OTHER INFORMATION: ttgg or no nucleotides
<220> FEATURE:
<221> NAME/KEY: MISC_FEATURE
<222> LOCATION: (21)..(24)
<223> OTHER INFORMATION: ttgg or no nucleotides
<220> FEATURE:
<221> NAME/KEY: MISC_FEATURE
<222> LOCATION: (25)..(28)
<223> OTHER INFORMATION: ttgg or no nucleotides
<220> FEATURE:
<221> NAME/KEY: MISC_FEATURE
<222> LOCATION: (29)..(32)
<223> OTHER INFORMATION: ttgg or no nucleotides
<220> FEATURE:
<221> NAME/KEY: MISC_FEATURE
<222> LOCATION: (33)..(36)
<223> OTHER INFORMATION: ttgg or no nucleotides
<220> FEATURE:
<221> NAME/KEY: MISC_FEATURE
<222> LOCATION: (37)..(40)
<223> OTHER INFORMATION: ttgg or no nucleotides

<400> SEQUENCE: 87
ttggttggtt ggttggttgg ttggttggtt ggttggttgg                              40

<210> SEQ ID NO 88
<211> LENGTH: 12
<212> TYPE: DNA
<213> ORGANISM: artificial sequence
<220> FEATURE:
<223> OTHER INFORMATION: probe

<400> SEQUENCE: 88
cccttaatcc cc                                                            12

<210> SEQ ID NO 89
<211> LENGTH: 120
<212> TYPE: DNA
<213> ORGANISM: homo sapiens

<400> SEQUENCE: 89
tatttttatt ataaggcctg ctgaaaatga ctgaatataa acttgtggta gttggagctg        60
atggcgtagg caagagtgcc ttgacgatac agctaattca gaatcatttt gtggacgaat       120

<210> SEQ ID NO 90
<211> LENGTH: 120
<212> TYPE: DNA
<213> ORGANISM: homo sapiens

<400> SEQUENCE: 90
tatttttatt ataaggcctg ctgaaaatga ctgaatataa acttgtggta gttggagctg        60
gtggcgtagg caagagtgcc ttgacgatac agctaattca gaatcatttt gtggacgaat       120

<210> SEQ ID NO 91
<211> LENGTH: 40
<212> TYPE: DNA
```

```
<213> ORGANISM: artificial sequence
<220> FEATURE:
<223> OTHER INFORMATION: probe

<400> SEQUENCE: 91
cccttaatcc ccgtgtcagc tccaactacc acaagtttat                              40

<210> SEQ ID NO 92
<211> LENGTH: 45
<212> TYPE: DNA
<213> ORGANISM: artificial sequence
<220> FEATURE:
<223> OTHER INFORMATION: probe

<400> SEQUENCE: 92
tcaaggcact cttgcctacg ccacacaggg tggggtgggg tgggg                        45
```

COMPOSITIONS AND METHODS FOR DETECTING SINGLE NUCLEOTIDE POLYMORPHISMS

CROSS REFERENCE TO RELATED APPLICATION

This claims the benefit U.S. Provisional Application No. 61/826,225, filed May 22, 2013, the disclosure of which is incorporated by reference in its entirety.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE DISCLOSURE

This relates to nucleic acid based probes and their uses for discriminating and detecting single nucleotide variants in DNA molecules by light emission color.

BACKGROUND

Variations in the nucleotide sequence of DNA impact if and how an organism develops diseases, and respond to pathogens, chemicals, drugs, vaccines and other agents.

Single-nucleotide variations, such as single-nucleotide polymorphisms (SNPs) or point mutations, play an important role in many human diseases. As genetic markers, SNPs can be used to trace generational inheritance patterns associated with specific diseases. As diagnostic markers, point mutations can be used for early cancer detection. Current methods for single nucleotide variation detection (e.g., genotyping of known SNPs) typically require enzymatic reactions such as primer extension, ligation, and cleavage, making these methods time consuming and expensive. Hybridization-based methods that rely on optical, electrical, or electrochemical signals for discrimination readout are considerably simpler in practice. However, most of these methods rely on differences in the free energy of probe/target binding for SNP differentiation (i.e., hybridization probes bind preferably to the fully matched target rather than the single-base mismatched targets, such as molecular beacons). Such differences in binding free energy are often small and can vary significantly on the basis of target sequence. Therefore, sophisticated probe design algorithms and use of hybridization enhancing moieties are often necessary. Further, optimized assay conditions (such as elevated temperature for molecular beacon discrimination) are often required, which also limit their use at point-of-care settings.

Therefore, there continues to be a need for rapid and precise screening of small genetic variations such as SNPs. The present disclosure meets such needs by removing or minimizing the disadvantages of existing methods, and further reducing costs associated with such probes and methods.

SUMMARY

Methods for detecting a variant nucleic acid sequence are provided herein.

In several embodiments, the methods include detecting a polymorphism in a test nucleic acid molecule compared to a control target nucleic acid molecule. The methods can include providing a test mixture comprising a first nucleic acid probe, a second nucleic acid probe, and the test nucleic acid molecule under conditions that permit duplex formation. The control target nucleic acid molecule comprises a first control nucleotide sequence contiguous to a second control nucleotide sequence. The first probe comprises a hybridization portion complementary to the first control nucleotide sequence, and a nucleation portion comprising templated metal nanoclusters that are fluorescent. The second probe comprises a hybridization portion complementary to the second control nucleotide sequence, and an enhancer portion comprising a nucleotide sequence that enhances fluorescent emission from the metal nanoclusters when associated with the metal nanoclusters. The method further comprises exposing the test mixture to an excitation light and measuring a wavelength of fluorescence emission from the mixture, and detecting the polymorphism by detecting a difference in the wavelength of the fluorescence emission of the test mixture compared to that of a corresponding control mixture comprising the first probe, the second probe, and the control target nucleic acid molecule. In several embodiments, the polymorphism is a single nucleotide polymorphism, such as a nucleotide substitution, deletion, or insertion.

In some embodiments, the polymorphism is a single nucleotide polymorphism located on a position of the first control nucleotide sequence that is immediately adjacent to the second control nucleotide sequence. In some such embodiments, the second probe comprises a nucleotide immediately adjacent to the hybridization portion of the second probe and which is in between the hybridization and enhancer portions, and which is complementary to the single nucleotide polymorphism.

In additional embodiments, the polymorphism is a single nucleotide polymorphism located on a position of the second control nucleotide sequence that is immediately adjacent to the first control nucleotide sequence. In some such embodiments, the first probe comprises a nucleotide immediately adjacent to the hybridization portion of the first probe and in between the hybridization and enhancer portions, and which is complementary to the single nucleotide polymorphism.

The excitation light can be selected from the group consisting of ultraviolet light, visible light, near infrared light or a combination thereof. In some embodiments, the difference in the wavelength of the fluorescence emission of the test mixture compared to that of the corresponding control mixture is at least 1 nm.

In further embodiments, the test nucleic acid molecule comprises a nucleotide sequence, or fragment thereof, selected from the group consisting of the β-globin gene, v-Ki-ras2 Kirsten rat sarcoma viral oncogene homolog (KRAS) gene, v-raf murine sarcoma viral oncogene homolog B1 (BRAF) gene, hexosaminidase A (HEXA) gene, p53 gene, Werner syndrome, RecQ helicase-like (WRN) gene, factor-associated suicide (FAS) gene, fat mass and obesity associates (FTO) gene and transcription factor 7-like 2 (TCF7L2) gene.

Reagents and kits for use in the disclosed methods are also provided.

The foregoing and other features and advantages of this disclosure will become more apparent from the following detailed description of several embodiments which proceeds with reference to the accompanying figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1B shows the probe bound to a first target (e.g., a reference target nucleic acid molecule). Each of the cNCB probes includes a hybridization portion that anneals to the target DNA. In the illustrated embodiment, the NC probe anneals immediately upstream on the target DNA to the annealing position of the enhancer probe. In FIG. 1B, the two probes anneal to the target DNA and the nanoclusters are in close proximity to the enhancer portion of the enhancer probe. In the illustrated embodiment, when illuminated with excitation light, the nanoclusters of the cNCB probe fluoresce at an orange wavelength of visible light. FIG. 1C shows the probe bound to a second target (e.g., a test nucleic acid molecule) that is a single nucleotide G↔T variant of the first target. Binding to the second target results in emission of red light. The wavelength of the emitted light is altered due to the change in position of the enhancer portion of the enhancer probe relative to the nanoclusters of the NC probe, depicted by the vertical arrow.

FIG. 2B shows two-dimensional fluorescence contour plots (emission (nm) on the X-axis and excitation (nm) on the Y-axis) of 11 hybridized samples and a control sample having the NC-probe without an enhancer probe ("NC-bearing strand only"), with the corresponding position number shown on the upper left corner of each plot. Twenty one visible excitation peaks were found in the visible to near-infrared excitation region (450-800 nm), which were categorized into four groups (I, II, III and IV, as indicated on the plots) based on their centroid locations. The control sample showed little fluorescence. The UV excitation regions (250-400 nm, shown on the lower portion of the 2D plots) are independently scaled in order to better display the UV excitation peaks. The 11 hybridized samples includes a common NC-sequence (SEQ ID NO: 1) and 11 different enhancer sequences (SEQ ID NOs: 5, 6, 7, 8, 9, 10, 11, 12, 13, 14 and 15), with each enhancer probe containing the same enhancer sequence (SEQ ID NO: 4) that is offset compared to the other probes. Each of SEQ ID NOs: 5-15 is represented in FIG. 2B as "−3", "−2", "−1", "0", "+1", "+2", "+3", "+4", "+5", "+6" and "+7", respectively (e.g., "−3" represents SEQ ID NO: 5, "−2" represents SEQ ID NO: 6), as aligned with the common NC-sequence (SEQ ID NO: 1).

FIG. 3A is a color photo of the eleven hybridized samples (position −3 to +7 corresponding to enhancer probes SEQ ID NOs: 5-15, respectively) and the control sample (NC-bearing probe without a hybridization partner) under UV 365 nm light. The samples were in 1.5 ml Eppendorf tubes and were placed on a commercial gel imager. FIG. 3B shows the emission spectra of the eleven samples under 365 nm excitation. FIG. 3C shows the emission-spectrum-global-maximum (ESGM), which sets a simple criterion for colorimetric probe design, of the eleven hybridized samples under 305 and 365 nm excitation, respectively. Error bars represent the standard deviations of measurements taken from five independently prepared sample sets.

FIG. 4A shows all 5 alignment positions ("−1", "0", "+1", "+2" and "+3") between the enhancer sequence (lower strand) and the NC-nucleation sequence (top strand). The ligand/base environment created around the 5'-CCCTT-3' section of the NC-nucleation sequence is identical for positions −1 and +3, as indicated by the dashed line boxes. FIG. 4B shows the fluorescence emission spectra of the 5 hybridized samples under 365 nm excitation. The spectra between 700-750 nm was removed due to a large peak caused by second-order diffraction of the 365 nm excitation.

FIGS. 5A-5E show the schematics and results for detecting a single-nucleotide variant in a Kras oncogene using the probes of the present disclosure. The cNCB_1 is the combination of "NC probe_1" (SEQ ID NO: 16) with "G-rich probe_1" (SEQ ID NO: 18), and separately the cNCB_2 is the combination of "NC probe_2" (SEQ ID NO: 17) with "G-rich probe_1" (SEQ ID NO: 18). The single-nucleotide mutation was a GGT (wild-type) to GTT (mutant-type) mutation in codon 12 of the Kras gene. FIGS. 5A and 5B are schematics showing the alignment of the three-way junction (3WJ) structures of the cNCB_1 and cNCB_2 with the Kras wild-type and mutant targets. The alignment of the individual strands of each of the probes is dictated by its binding/hybridization with the target sequences, which in turn determines the color emission by the probe. Sample A is the combination of the cNCB_1 with the Kras mutant target (red color emission) and Sample B is the combination of the cNCB_1 with the Kras wild-type target (yellow/orange color emission). Sample D is the combination of the cNCB_2 with the Kras mutant target (red color emission) and Sample E is the combination of the cNCB_2 with the Kras wild-type target (yellow/orange color emission). FIG. 5C shows color photos of 6 samples under 365 nm irradiation. The left image was taken 60 minutes after mixing the cNCB_1 (Samples A and B) and cNCB_2 (Samples D and E) probes with the Kras wild-type (+1 or +2) and mutant (−1 or 0) targets (no prior UV exposure). The middle image was taken at 500 minutes (no prior UV exposure). The right image was taken at 60 minutes, following multiple short UV exposures. FIGS. 5D and 5E show emission spectra (under 365 nm excitation) of the 6 samples at 60 minutes (top), 500 minutes (middle), and at 60 minutes but with multiple short UV exposures (bottom), respectively.

FIGS. 6A-6F show the emission spectra, under 365 nm excitation, for 12 different cNCBs (12 sample sets) used to discriminate six different single-nucleotide substitution scenarios in a Kras sequence (i.e., C↔G, G↔A, C↔T, A↔C, T↔A and G↔T). Each sample set was a unique cNCB. Each of the six single-nucleotide substitution scenarios were tested with two different cNCBs (or two different sample sets).

FIGS. 7A-7F show the emission spectra, under 365 nm excitation, for 12 different cNCBs (12 sample sets) used to discriminate six different single-nucleotide substitution scenarios in a Braf sequence (i.e., C↔G, G↔A, C↔T, A↔C, T↔A and G↔T). Each sample set was a unique cNCB. Each of the six single-nucleotide substitution scenarios were tested with two different cNCBs (or two different sample sets).

FIGS. 8A-8F show the emission spectra, under 365 nm excitation, for 12 different cNCBs (12 sample sets) used to discriminate six different single-nucleotide substitution scenarios in a disease related Sickle-Cell Anemia nucleotide sequence (i.e., C↔G, G↔A, C↔T, A↔C, T↔A and G↔T). Each sample set was a unique cNCB. Each of the six single-nucleotide substitution scenarios were tested with two different cNCBs (or two different sample sets).

FIGS. 9A and 9B shows the detection of Kras point mutations in two clinical samples using a cNCB. Sample A contained Kras heterozygous targets (both GGT and GAT targets), while sample B contained only Kras wild-type target (GGT target). The cNCB used here, denoted cNCB_3, includes two probes: the NC-nucleation sequence (SEQ ID NO: 91), and the G-rich sequence (SEQ ID NO: 92). The cNCB_3 was designed to hybridize to both the wild-type and mutant sequences. Position +1 with the GGT target, and position −1 with the GAT target. FIG. 9A is a photo of the cNCB_3 mixed with DNA amplified from the two clinical samples. The color of sample A, with both the GGT and GAT targets, appeared red shifted due to the fact that about half the cNCB probes targets generated a position −1 conformation. FIG. 9B shows the emission spectra of samples A and B.

SEQUENCE LISTING

Figure 1A:
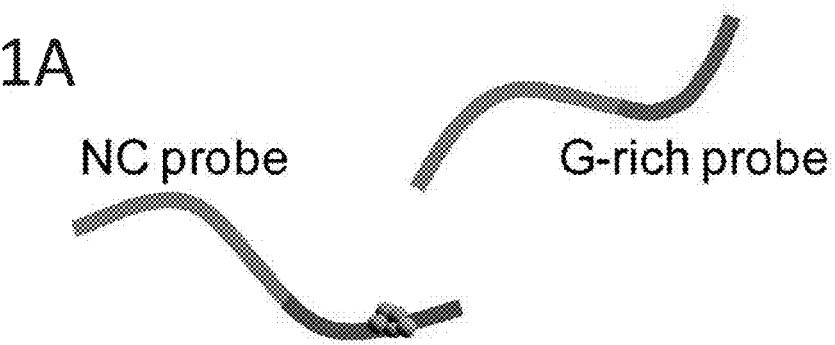
FIGS. 1A-1C show schematic diagrams illustrating the function of the disclosed chameleon Nanocluster Beacons (cNCBs). The cNCBs include a nanocluster (NC) probe and an enhancer (or G-rich) probe (FIG. 1A).

The nucleic and amino acid sequences listed in the accompanying sequence listing are shown using standard letter abbreviations for nucleotide bases as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~20 kb), which was created on May 20, 2014 which is incorporated by reference herein.

DETAILED DESCRIPTION

I. Summary of Terms

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. As used herein, the term "comprises" means "includes." Thus, "comprising a nucleic acid molecule" means "including a nucleic acid molecule" without excluding other elements. It is further to be understood that any and all base sizes given for nucleic acids are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

3' end: The end of a nucleic acid molecule that does not have a nucleotide bound to it 3' of the terminal residue.

5' end: The end of a nucleic acid sequence where the 5' position of the terminal residue is not bound by a nucleotide.

Analog: Analog, as used herein, refers to a chemical or compound that shares similar functional properties and/or structural properties with a different chemical or compound.

Chameleon Nanocluster Beacon: (cNCB). A cNCB includes two single-stranded nucleic acid probes that are designed to complement with contiguous sections of a target nucleic acid. One of the probes of the cNCB includes a "nucleation portion" that includes a nucleotide sequence that can bind to metal nanoclusters. The other probe of the cNCB includes an "enhancer portion" that includes a nucleotide sequence which can produces an enhancement in fluorescence from the nanoclusters when the enhancer sequence is in sufficient proximity to the nanoclusters and the hybridized probe is subjected to excitation light (e.g., ultraviolet light). When the two probes are brought into sufficient proximity by binding the contiguous sections of the target nucleic acid sequence, the nucleation portion (and the metal nanoclusters) and the enhancement portion are in close proximity, which can be detected by detecting an increase in fluorescence intensity of the metal nanoclusters. When the underlying sequence of the target nucleic acid varies (e.g., due to a polymorphism) the alignment of the metal nanoclusters and the enhancer sequence is offset. Offsetting this alignment causes a resulting change in the wavelength (e.g., the fluorescence spectra) of the fluorescence emitted from the nanoclusters, which can be detected, and used to identify the variant in the variant target nucleic acid sequence.

Complementary: Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions. In particular examples disclosed herein, the complementary sequence is complementary at a labeled nucleotide, and at each nucleotide immediately flanking the labeled nucleotide.

Consists of and Consists Essentially of: With regard to a polynucleotide (such as a probe or primer), a polynucleotide consists essentially of a specified nucleotide sequence if it does not include any additional nucleotides. However, the polynucleotide can include additional non-nucleic acid components, such as labels (for example, fluorescent, radioactive, or solid particle labels), sugars, peptidic backbones, synthetic substituents or lipids. With regard to a polynucleotide, a polynucleotide that consists of a specified nucleotide sequence does not include any additional nucleotides, nor does it include additional non-nucleic acid components, such as lipids, sugars or labels other than templated metal nanoclusters. Thus, reference to a polynucleotide that "consists of" a nucleotide sequence including a nucleation sequence, the polynucleotide can include templated metal nanoclusters (but not other types of labels), unless indicated otherwise.

Contacting: Placement in direct physical association, for example solid, liquid or gaseous forms. Contacting includes, for example, direct physical association of fully- and partially-solvated molecules.

Control: A sample or standard used for comparison with an experimental sample. In some embodiments, the control is a sample obtained from a healthy subject (or a plurality of healthy subjects), such as a subject or subjects not expected or known to have a particular polymorphism. In additional embodiments, the control is a historical control or standard reference value or range of values (such as a previously tested control sample or plurality of such samples), or group of samples that represent baseline or normal values. A positive control can be an established standard that is indicative of a specific polymorphism. In some embodiments a control nucleic acid is one that lacks a particular polymorphism, and is used in assays for comparison with a test nucleic acid, to determine if the test nucleic acid includes the polymorphism.

Detecting: To identify the existence, presence, or fact of something. General methods of detecting are known to the skilled artisan and may be supplemented with the protocols and reagents disclosed herein. For example, included herein are methods of detecting a nucleic acid molecule in sample. Detection can include a physical readout, such as fluorescence output.

Enhancer Sequence: A nucleotide sequence that when placed in proximity to another nucleic acid molecule having templated metal nanoclusters increases the fluorescence intensity of the metal nanocluster when exposed to excitation light. Exemplary enhancer sequences are known in the art and disclosed herein.

Excitation Light: Light of any wavelength that is capable of causing template metal nanoclusters to fluoresce. Non-limiting examples of excitation light include visible light, ultraviolet and near infrared light.

Hybridization: To form base pairs between complementary regions of two strands of DNA, RNA, or between DNA and RNA, thereby forming a duplex molecule, for example. Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
  Hybridization: 5×SSC at 65° C. for 16 hours
  Wash twice: 2×SSC at room temperature (RT) for 15 minutes each
  Wash twice: 0.5×SSC at 65° C. for 20 minutes each
High Stringency (Detects Sequences that Share at Least 80% Identity)
  Hybridization: 5x-6×SSC at 65° C.-70° C. for 16-20 hours
  Wash twice: 2×SSC at RT for 5-20 minutes each
  Wash twice: 1×SSC at 55° C.-70° C. for 30 minutes each
Low Stringency (Detects Sequences that Share at Least 60% Identity)
  Hybridization: 6×SSC at RT to 55° C. for 16-20 hours
  Wash at least twice: 2x-3×SSC at RT to 55° C. for 20-30 minutes each Increase or Decrease: A statistically significant positive or negative change, respectively, in quantity from a control value. An increase is a positive change, such as a 50%, 100%, 200%, 300%, 400% or 500% increase as compared to the control value. A decrease is a negative change, such as a 50%, 100%, 200%, 300%, 400% or 500% decrease as compared to a control value.

Isolated: An "isolated" biological component (such as a nucleic acid molecule) has been substantially separated, produced apart from, or purified away from other biological components. Nucleic acid molecules which have been "isolated" include nucleic acids molecules purified by standard purification methods, as well as those chemically synthesized. Isolated does not require absolute purity, and can include nucleic acid molecules that are at least 50% isolated, such as at least 75%, 80%, 90%, 95%, 98%, 99% or even 100% isolated.

Metal nanocluster: Collections of small numbers (e.g., 2-30 atoms) of noble metal atoms (e.g., gold or silver atoms) with physical sizes close to the Fermi wavelength of an electron (~0.5 nm for gold and silver). The metal atoms can have affinity for nitrogen atoms on DNA, including the N3 of cytosine and the N7 of guanine. Metal nanoclusters for use with the disclosed embodiments are fluorescent, that is, they have the ability to emit light of a particular wavelength (emission wavelength) when exposed to light of another wavelength (excitation wavelength).

Specific nucleotide sequence ("nucleation sequences") that are useful for interacting with metal nanoclusters and forming DNA templated metal nanoclusters are disclosed herein. Examples of metal nanoclusters for use as fluorescent reporters, and methods of producing templated metal nanoclusters on DNA oligonucleotides are known. See, e.g., U.S. Pat. App. Pub. 2011/0212540 entitled "Probe and Method for DNA Detection", which was filed Feb. 22, 2011, and is incorporated by reference herein in its entirety. See also Richie et al., "Ag Nanocluster Formation using a cytosine oligonucleotide template," *J Phys Chem C,* 111, 175-181, 2006, which is incorporated by reference herein in its entirety.

Nucleation Sequence: A sequence of nucleotides capable of binding or associating with metal atoms to form templated metal nanoclusters. The portion of a nucleic acid molecule including a nucleation sequence of nucleotides is referred to as the "nucleation portion" of the nucleic acid molecule. Exemplary nucleation sequences are known and provided herein.

Nucleic acid: A deoxyribonucleotide or ribonucleotide polymer, which can include analogues of natural nucleotides that hybridize to nucleic acid molecules in a manner similar to naturally occurring nucleotides. In a particular example, a nucleic acid molecule is a single stranded (ss) DNA or RNA molecule, such as a probe or primer. In another particular example, a nucleic acid molecule is a double stranded (ds) nucleic acid, such as a target nucleic acid. Examples of modified nucleic acids are those with altered backbones, such as peptide nucleic acids (PNA).

Nucleotide: The fundamental unit of nucleic acid molecules. A nucleotide includes a nitrogen-containing base attached to a pentose monosaccharide with one, two, or three phosphate groups attached by ester linkages to the saccharide moiety.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, as known in the art.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, and 2,6-diaminopurine.

Examples of modified sugar moieties which may be used to modify nucleotides at any position on its structure include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Polymorphism: A variation in a gene sequence. The polymorphisms can be those variations (DNA sequence differences, e.g., substitutions, deletions, or insertions) which are generally found between individuals or different ethnic groups and geographic locations which, while having a different sequence, produce functionally equivalent gene products. Typically, the term can also refer to variants in the sequence which can lead to gene products that are not functionally equivalent. Polymorphisms also encompass variations which can be classified as alleles and/or mutations which can produce gene products which may have an altered function. Polymorphisms also encompass variations which can be classified as alleles and/or mutations which either produce no gene product or an inactive gene product or an active gene product produced at an abnormal rate or in an inappropriate tissue or in response to an inappropriate stimulus. Alleles are the alternate forms that occur at the polymorphism.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation.

Probe: Probes are short nucleic acid molecules, usually DNA oligonucleotides, typically of about 20-100 nucleotides in length, used to detect the presence of a complementary target DNA strand in a sample. All or a portion of a probe can be annealed to a complementary target DNA strand by nucleic acid hybridization to form a hybrid between the primer and the target DNA strand. Therefore, probes can be used to identify a target nucleic acid molecule, wherein the sequence of the probe is specific for the target nucleic acid molecule, for example so that the probe will hybridize to the target nucleic acid molecule under very high stringency hybridization conditions.

Typically, probes include at least about 10 contiguous nucleotides, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50 contiguous nucleotides, that are complementary to a target nucleic acid molecule, such as 20-70 nucleotides, 20-60 nucleotides, 20-50 nucleotides, 20-40 nucleotides, or 20-30 nucleotides. Probes can also be of a maximum length, for example no more than 20, 25, 25, 40, 50, 75 or 100 nucleotides in length. The specificity of a particular probe typically increases with an increase in the number of complementary nucleotides on the probe.

The probe can also include additional nucleotides that are not complementary to the target nucleic acid molecule. The additional nucleotides can be used, for example, for detection of the probe in a sample. In several embodiments, the probes disclosed herein include a hybridization portion that is complementary to a test nucleic acid sequence, and a nucleation portion (that can associate with metal nanoclusters) or an enhancer portion (that can enhance the fluorescence of metal nanoclusters associated with the nucleation portion. The additional nucleotides can be located 5' or 3' of the hybridization nucleotides.

Methods for preparing and using nucleic acid probes are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990).

Sample: A sample, such as a biological sample, is a sample obtained from a subject. As used herein, biological samples include all clinical samples useful for detection of a polymorphism, including, but not limited to, cells, tissues, and bodily fluids, such as: blood; derivatives and fractions of blood, such as serum; urine; sputum; or CVS samples. In a particular example, a sample includes blood obtained from a human subject, such as whole blood or serum.

Sequence identity/similarity: The identity/similarity between two or more nucleic acid sequences is expressed in terms of the identity between the sequences. Sequence identity can be measured in terms of percentage identity; the higher the percentage, the more identical the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biotechnology (NCBI, National Library of Medicine, Building 38A, Room 8N805, Bethesda, Md. 20894) and on the Internet, for use in connection with the sequence analysis programs blastp, blastn, blastx, tblastn, and tblastx. Additional information can be found at the NCBI web site. BLASTN is used to compare nucleic acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

One indication that two nucleic acid molecules are closely related is that the two molecules hybridize to each other under stringent conditions, as described above.

Single nucleotide polymorphism (SNP): The polynucleotide sequence variation present at a single nucleotide residue within different alleles of the same genomic sequence. This variation may occur within the coding region or non-coding region (i.e., in the promoter region) or an intergenic (between genes) sequence of a genomic sequence. Detection of one or more SNPs allows differentiation of different alleles of a single genomic sequence.

Subject: Any mammal, such as humans, non-human primates, pigs, sheep, cows, rodents and the like. In two non-limiting examples, a subject is a human subject or a murine subject. Thus, the term "subject" includes both human and veterinary subjects.

Test nucleic acid molecule: A nucleic acid molecule whose detection, quantitation, qualitative detection, characterization, or a combination thereof, is intended. For example, the test nucleic acid molecule can be a defined region or particular portion of a nucleic acid molecule, for example a portion of a genome (such as a gene or a region of DNA or RNA containing a gene (or portion thereof) of interest). The nucleic acid molecule need not be in a purified form. Various other nucleic acid molecules can also be present with the test nucleic acid molecule. For example, the test nucleic acid molecule can be a specific nucleic acid molecule (which can include RNA or DNA), for which the detection of a particular polymorphism is intended. In some examples, a test nucleic acid includes a viral nucleic acid molecule, or a bacterial nucleic acid molecule. Purification or isolation of the test nucleic acid molecule, if needed, can be conducted by methods known to those in the art, such as by using a commercially available purification kit or the like.

Under conditions sufficient for: A phrase that is used to describe any environment that permits a desired activity. In one example the desired activity is hybridization of a probe to a target nucleic acid molecule.

Wild-type: The genotype or phenotype that is most prevalent in nature. The naturally occurring, non-mutated version of a nucleic acid sequence. Among multiple alleles, the allele with the greatest frequency within the population is usually (but not necessarily) the wild-type. The term "native" can be used as a synonym for "wild-type."

II. Detecting Sequence Variation

A method is disclosed for detecting a nucleic acid sequence variation between a test nucleic acid and a control nucleic acid using cNCBs. The cNCB includes two probes that each include portions complementary to contiguous sections of the control nucleic acid sequence. The two probes can also include regions of complementarity with each other, e.g., to make the three-way-junction (3WJ) discussed below. One of the probes of the cNCB includes a "nucleation portion" that includes a nucleotide sequence that can bind to metal nanoclusters. The other probe of the cNCB includes an "enhancer portion" that includes a nucleotide sequence that can enhance fluorescence emitted from the nanoclusters when in sufficient proximity to the nanoclusters. When the two probes are brought into sufficient proximity by binding the contiguous sections of the control nucleic acid sequence, the nucleation portion (and the metal nanoclusters) and the enhancement portion are in close proximity, which can be detected by detecting an increase in fluorescence intensity of the metal nanoclusters.

With reference to FIG. 5, the probes for use in the disclosed embodiments are based on a 3WJ design where a single nucleotide substitution on the target DNA (positioned at the branch point of the 3WJ) causes frame-shift base pairing in the third arm of the 3WJ that is perpendicular to the target nucleic acid molecule. This frame-shift base pairing moves the enhancer sequence relative to the NC-nucleation sequence by two nucleotides, resulting in a detectable change in fluorescence emission wavelength of the metal nanoclusters. Thus, when the underlying sequence of the target nucleic acid varies (e.g., due to a polymorphism) the alignment of the metal nanoclusters and the enhancer sequence is offset, which causes a detectable change in the wavelength (e.g., the fluorescence spectra) of the fluorescence emitted from the nanoclusters. This detectable change in fluorescence can be detected and used to identify the variant in the variant target nucleic acid sequence.

As illustrated by FIG. 1, the method can include mixing the test nucleic acid, a first probe and a second probe under conditions sufficient for duplex formation to form a test mixture. The first and second probes include hybridization portions that include sequences complementary to the sequence of a control nucleic acid molecule, which includes a first control nucleotide sequence contiguous to a second control nucleotide sequence. The hybridization portions of the first and second probes are complementary to the first and second control nucleic acid sequences, respectively.

The first probe also includes a nucleation portion including templated metal nanoclusters, which can fluoresce when exposed to excitation light (e.g., UV light). The second probe includes an enhancer portion including a nucleotide sequence that enhances fluorescent emission from the metal nanoclusters when associated with the metal nanoclusters (see, e.g., FIGS. 1B and 1C).

The test mixture is exposed to excitation light, and any corresponding fluorescence is measured. Detecting a difference in the wavelength of the fluorescence emission of the test mixture compared to that of a corresponding control mixture comprising the first probe, the second probe, and the control nucleic acid molecule detects the presence of a polymorphism in the test nucleic acid molecule compared to the control nucleic acid molecule.

Thus, a difference between the emission from the test mixture and the control mixture indicates sequence variation at the junction of the hybridization portions of the first and second probe. The difference in wavelength fluorescence emission between the test mixture and the control mixture can be a visible color difference. In more embodiments, the difference in wavelength fluorescence emission between the test mixture and the control mixture is at least 1 nm (such as at least 2, 3, 4, 5, 6, 7, 89, 10, 15, 20, 25, 30, 40, 50, 60, 70, 80, 90, or 100 nm). The test nucleic acid molecule may be compared to multiple different reference standard nucleic acid molecules.

In some embodiments, the sequence variation detected is an SNP. The measured fluorescence of the control mixture serves as a reference standard for comparison purposes to the measured fluorescence of the test mixture. Where the control mixture and the test mixture provide the same or substantially similar measurable wavelength or range of wavelengths upon exposure to excitation light, it may be concluded that the test nucleic acid molecule and the control nucleic acid molecule have the same nucleotide sequence across the junction of the hybridization portions of the first and second probes. Where the control mixture and the test mixture provide the different measurable wavelength or range of wavelengths upon exposure to excitation light, it may be concluded that the test nucleic acid molecule and the control nucleic acid molecule do not have the same nucleotide sequence across the junction of the hybridization portions of the first and second probes.

Using the 3WJ design of the first and second probes (see FIG. 5), the first probe can include a hybridization portion that complements with a control allele (e.g., a wild-type allele) of a known polymorphism, and the second probe can be designed to complement with the most common variant allele of the polymorphism (e.g., a SNP). As illustrated in the Examples, the emission profile of the two probes hybridized to the target nucleic acid molecule can distinguish the control allele and the most common variant allele, one of which will be complementary to the hybridization portion of the first or second probe, respectively. Additionally, the emission profile can further distinguish if the target nucleic acid molecule includes neither the control allele nor the most common variant.

Information about sequence variation can be used in a variety of ways. For example, polymorphisms, such as SNPs, can be used to assess allelic frequencies within populations, construct genetic maps, or identify genetic diseases. Melting profiles and the resulting sequence variation information can be useful for studying molecular interactions and signal transduction systems, such as nucleic acid interactions with hormones, repressors, transcription factors, chromatin, and other cellular molecules; in vitro molecular mechanisms, such as RNA splicing or post-transcriptional modification; and for studying the role of modified bases in nucleic acid chemistry, such as for drug design and development of anti-viral agents.

SNPs and their allelic variants are well known and multiple SNP databases are available via the world-wide web. For example, the National Center for Biotechnology Information (NCBI) hosts a publicly accessible SNP database (dbSNP) containing a broad collection of genetic polymorphisms. SNPedia is another publicly available database containing approximately 37,954 available SNPs. Generally, SNPs are given identification numbers (IDs) proceeded by "rs" or "Rs", which refers to "Reference SNP". SNPs may be searched by their Rs number and/or by the disease or condition that the SNP has been associated to or linked with. Therefore, using 3WJ design, the first and second probes can be designed to distinguish between two alleles of a SNP, such as the wild-type and most common variant alleles. In some embodiments, a genetic disease in a subject is detected based on a difference between the emission profiles of a nucleic acid obtained from that subject and the corresponding wild-type nucleic acid. In particular embodiments, the genetic disease results from an SNP.

In addition to polymorphism discrimination, the disclosed methods of using cNCBs can also be used to quantify a polymorphism in a sample, for example, to determine an amount of the test nucleic acid in the sample, by comparing the fluorescence of the test mixture to that of a control mixture with a known amount of DNA including a particular polymorphic or control nucleic acid molecule. Additionally, if a test sample includes both polymorphic and control sequences, the disclosed methods can be used to determine the proportion of polymorphic to control nucleic acid sequences in the sample by comparing the fluorescence of the test mixture to that of a control mixture with a known mixture of polymorphic:control nucleic acid molecules.

Additionally, the environmental sensitivity of DNA/Ag NCs can also be used to create a spectroscopic ruler that can report small conformational change or change in spatial arrangement due to various biomolecular interactions. Such a ruler would complement existing spectroscopic rulers, such energy transfer-based, electron transfer-based, switching dynamics-based, nanometal surface energy transfer-based, or plasmon coupling-based rulers.

A. Probes

As disclosed herein, the cNCBs include a first probe and a second probe, which together can be used to detect a polymorphism in a target nucleic acid molecule. The first probe can include a nucleation sequence upon which metal nanoclusters can be templated. The metal nanoclusters are associated with a nucleation sequence that can part of one of the cNCB probes. The nucleation sequence can include, for example, the nucleotide sequence set forth as CCCT-TAATCCCC (SEQ ID NO: 88). In several embodiments, the first probe includes the nucleotide sequence of 5'-CCCT-TAATCCCC (SEQ ID NO: 88)-N-$H_1$-3', wherein N is any nucleotide and $H_1$ is the hybridization portion and comprises a nucleotide sequence of at least 10 nucleotides. In a related aspect, $H_1$ comprises a nucleotide sequence of from 15 to 45. In another aspect, the first probe comprises, consists of, or consists essentially of the nucleotide sequence set forth as one of SEQ ID NOs: 23-26, 35-38, 47-50, 65, 69, 73, 77 and 81.

The first probe can be at least 20 nucleotides in length. For example, the hybridization portion of the first probe can be at least 10 nucleotides in length and/or the nucleation portion of the first probe can be at least 10 nucleotides in length. In additional embodiments, the hybridization portion of the first probe has a $T_m$ of from about 10° C. to about 100° C.

The second probe can include an enhancer sequence that, when placed in proximity to another nucleic acid molecule having templated metal nanocluster, increases the fluorescence intensity of the metal nanoclusters when exposed to excitation light. Exemplary enhancer sequences that may be used in the disclosed embodiments include those listed in Table 1 below.

TABLE 1

| SEQ ID NO: | Name of probe | Sequence (5'-3') | Length (nts.) |
|---|---|---|---|
| 4 | G-rich portion_1 | GGGTGGGGTGGGGTGGGG | 18 |
| 83 | G-rich repeat (F) | (GGGGT)$_n$; n = 1-10 | 5-50 |
| 84 | G-rich repeat (R) | (TGGGG)$_n$; n = 1-10 | 5-50 |
| 85 | T-repeat | TTTTTTTTTTTT | 12 |
| 86 | GT-repeat (F) | (GGTT)$_n$; n = 1-10 | 4-40 |
| 87 | GT-repeat (R) | (TTGG)$_n$; n = 1-10 | 4-40 |

For example, the enhancer sequence can include the nucleotide sequence set forth as GGGTGGGGTGGGGTGGGG (SEQ ID NO: 4). In another aspect, the enhancer sequence comprises a nucleotide sequence selected from the group consisting of 5'-(GGGGT)$_n$-3' (SEQ ID NO: 83); 5'-TTTTTTTTTTTT-3' (SEQ ID NO: 85); 5'-(TGGGG)$_n$-3'(SEQ ID NO: 84); 5'-(GGTT)$_n$-3'(SEQ ID NO: 86); 5'-(TTGG)$_n$-3' (SEQ ID NO: 87) and combinations thereof, wherein n is from 1 to 5 (or 1, 2, 3, 4, or 5). In related aspect, the enhancer portion of the second probe comprises at least 40% guanine or analog thereof. In a related aspect, the enhancer portion of the second probe comprises from 40% to 95% (such as 40%, 45%, 50%, 55%, 60%, 65%, 70%, 75%, 80%, 85%, 90% or 95%) guanine or analog thereof. In related aspect, the enhancer portion of the second probe comprises at least 40% thymine or analog thereof. In a related aspect, the second portion of the second nucleic acid molecule comprises from 40% to 95% (such as 40%, 45%, 50%, 55%, 60%, 65%, 70%, 75%, 80%, 85%, 90% or 95%) thymine or analog thereof. In a related aspect, the enhancer sequence comprises a nucleotide sequence comprising at least 5 thymine bases. In a related aspect, the enhancer sequence comprises a nucleotide sequence comprising from about 5 to 20 thymine bases (or 5, 6, 7, 8, 9, 10, 11, 12, 13, 14, 15, 16, 17, 18, 19 or 20). Ina related aspect, the enhancer sequence comprises a nucleotide sequence comprising at least 5 guanine bases. In a related aspect, the enhancer sequence comprises a nucleotide sequence comprising from about 5 to 20 guanine bases (or 5, 6, 7, 8, 9, 10, 11, 12, 13, 14, 15, 16, 17, 18, 19 or 20). In several embodiments, the enhancer portion of the second probe comprises or consists of guanine and/or thymine nucleotides, or analogs thereof.

In some embodiments, the second nucleic acid probe includes the nucleotide sequence set forth as 5'-H$_2$-N-GGGTGGGGTGGGGTGGGG-3' (SEQ ID NO: 4), wherein H$_2$ is the hybridization portion of the probe and comprises a nucleotide sequence of at least 10 nucleotides and N is any nucleotide. In a related aspect, H$_2$ comprises a nucleotide sequence of from 15 to 45 nucleotides. In another aspect, the second probe comprises, consists of, or consists essentially of the nucleotide sequence set forth as one of SEQ ID NOs: 27-30, 39-42, 51-54, 66, 70, 74, 78 and 82.

The second probe can be at least 20 nucleotides in length. For example, the hybridization portion of the second probe can be at least 10 nucleotides in length and/or the enhancer portion of the second probe can be at least 10 nucleotides in length. In additional embodiments, the hybridization portion of the second probe has a T$_m$ of from about 10° C. to about 100° C.

In further embodiments, the first and second probes comprise or consist of nucleotide sequences set forth as:
(i) one of SEQ ID NOs: 23-26 and one of SEQ ID NOs: 27-30, respectively;
(ii) one of SEQ ID NOs: 35-38 and one of SEQ ID NOs: 39-42, respectively;
(iii) one of SEQ ID NOs: 47-50 and one of SEQ ID NOs: 51-54, respectively;
(iv) SEQ ID NO: 65 and SEQ ID NO: 67, respectively;
(v) SEQ ID NO: 69 and SEQ ID NO: 70, respectively;
(vi) SEQ ID NO: 73 and SEQ ID NO: 74, respectively;
(vii) SEQ ID NO: 77 and SEQ ID NO: 78, respectively; or
(viii) SEQ ID NO: 81 and SEQ ID NO: 82, respectively.

As discussed in the Examples, the enhancer sequence, and the alignment of the enhancer sequence with the metal nanoclusters, can alter the emission profile of the nanoclusters to excitation light. For example, when an enhancer of 12 thymine bases (SEQ ID NO: 85) was placed in proximity to the NC-nucleation sequence, the resulting emission profile was altered to a more green fluorescence, whereas, whereas red fluorescence enhancement dominated for an enhancer of substantial guanine content (e.g., SEQ ID NO: 4) on the same nucleation sequence (see the position-shifting experiments shown in FIGS. 2 and 3). These two different fluorescence emission colors from two distinct enhancer sequences show that the ligand/base environment surrounding the Ag NC is a strong determinant of the fluorescence emission color and intensity.

The first and second probes for use in the disclosed methods can be designed and synthesized by one of ordinary skill in the art by identifying any particular SNP and/or mutant sequence and the nucleic acid sequence on either side of the SNP and/or mutation. This sequence information may then be used as the basis for the developing a pair of probes that is capable of hybridizing with the nucleic acid sequence containing the SNP and/or mutation. In most cases, the nucleic acid sequence on either side of the SNP will be a nucleic acid sequence found in the genome of organism of interest or may be based on cDNA (derived from mRNA of an expressed sequence).

B. Metal Nanoclusters

The disclosed embodiments take advantage of the fluorescent properties of metal (e.g., silver) nanoclusters when the nanoclusters are brought near a DNA sequence referred to herein as an "enhancer sequence". The metal of the templated metal nanoclusters can be a noble metal, such as silver, gold, or copper. DNA-templated silver nanoclusters can emit colored light through interactions with "enhancer" sequences. The color of the emitted light was found to depend on the particular enhancer sequence. Silver nanoclusters are groups of from about 2 to about 30 silver atoms that are sub 2 nm in size with the properties of good fluorescence, good photostability, and electroluminescence. These silver nanoclusters, which are templated on the nucleation sequence of an embodiment probe, function as fluorescence reporters.

To form metal nanoclusters on DNA, positively charged metal ions (e.g., Ag+ atoms) are first attached to ssDNA (e.g., cytosine nucleotides) spontaneously in solution. Then, a reductant (e.g., sodium borohydride) is added to reduce the charge of the atoms (e.g., Ag+ to Ag(0)), after which metal atom "clusters" will form. The ssDNA prevents the metal cluster "from growing out of control". Clusters that become a "nanoparticle" (size >5 nm) are not fluorescent.

Examples of metal nanoclusters for use as fluorescent reporters, and methods of producing templated metal nanoclusters on DNA oligonucleotides are known. See, e.g., U.S. Pat. App. Pub. 2011/0212540 entitled "Probe and Method for DNA Detection", which was filed Feb. 22, 2011, and is incorporated by reference herein in its entirety. See also Richie et al., "Ag Nanocluster Formation using a cytosine oligonucleotide template," *J Phys Chem C,* 111, 175-181, 2006, which is incorporated by reference herein in its entirety. The basis for the operation of the templated metal nanoclusters is a controlled conversion of DNA-templated silver nanoclusters between a dark, non-emissive state, which is their state when not associated with an enhancer sequence, and a bright, emissive state when associated with the enhancer sequence. Unlike prior use of metal nanoclusters, the present method involves tuning the fluorescent emission properties of the metal nanoclusters (e.g., a wavelength shift of 60-70 nm) by altering the relative positions of the nanoclusters to the and the enhancer sequence.

The disclosure of the following references and their description of templated metal nanoclusters and their use and detection is incorporated by reference herein in its entirety: Petty et al., *J American Chemical Society* 2004, 126, 5207; Vosch et al., *Proc. Natl. Acad. Sci. U.S.A.* 2007, 104, 12616; Gwinn et al., *Adv. Mater.* 2008, 20, 279; Petty et al., *Anal. Chem.* 2011, 83, 5957; Sharma et al., *Chem. Commun.* 2010, 46, 3280; Sharma et al., *Chem. Commun.* 2011, 47, 2294; Neidig et al., *J. Am. Chem. Soc.* 2011, 133, 11837; and Yeh et al., *Nano Lett.* 2010, 10, 3106.

Noble metal nanoclusters, such as those made of silver, gold, copper, or other noble metals typically include collections of a number of metal atoms (approximately 2-30 atoms or 2, 3, 4, 5, 6, 7, 8, 9, 10, 11, 12, 13, 14, 15, 16, 17, 18, 19, 20, 21, 22, 23, 24, 25, 26, 27, 28, 29 or 30 atoms) with physical sizes close to the Fermi wavelength of an electron (e.g., about 0.5 nm for gold and silver). They behave like molecular systems and yield fluorescence emission in the UV-visible and infrared range. In some examples, oligonucleotide-templated silver nanoclusters ("DNA/Ag NCs"), which are a versatile set of fluorophores that have been used for a variety of applications including live cell imaging, detection of specific metal ions, and single-nucleotide variation identification. DNA/Ag NCs can be biocompatible and can have better photostability than commonly used organic dyes. Unlike organic dyes and photoluminescent nanocrystals, they are subject to silver oxidation/reduction or nanocluster ("NC") regrouping, which results in conversion among different NC species. These different species may provide different color emissions.

Figure 1B:
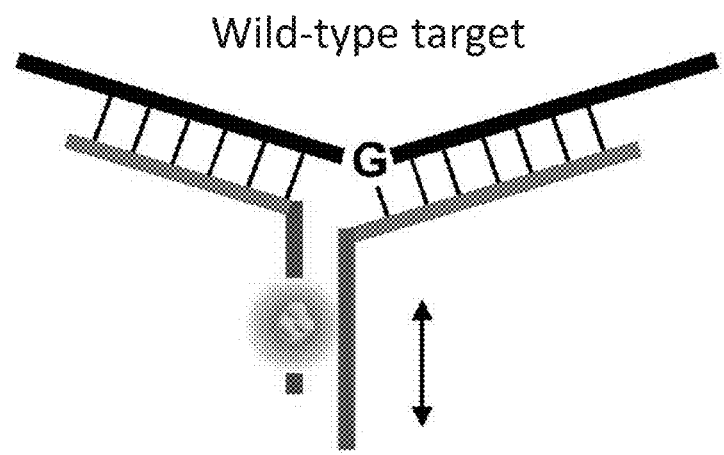
Figure 1C:
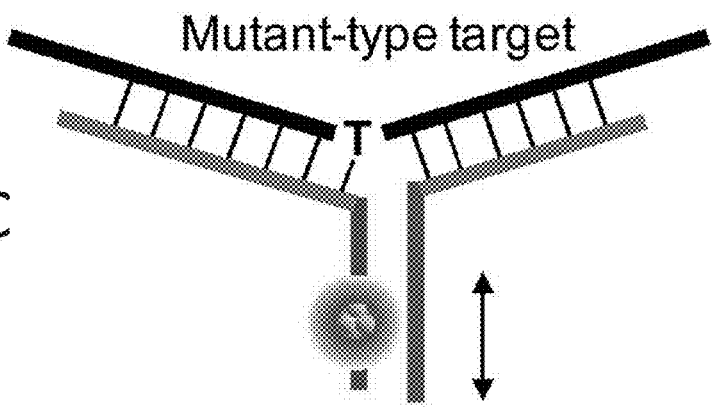

In the disclosed embodiments, the proximity of metal nanoclusters with an enhancer sequence occurs when the NC and enhancer portions of two probes of the cNCB are brought into close proximity by the hybridization of the hybridization portion of the probes with a contiguous portion of a target nucleic acid molecule. Prior to hybridization, the nanoclusters are only weakly fluorescent or non-fluorescent. For example, the schematic diagram of FIG. 1A shows two probes that make up a cNCB, when the probes are not yet hybridized to the target DNA. The Ag NCs on the nucleation sequence of the unhybridized probe are referred to as "dark Ag-NCs". The schematic diagrams of FIG. 1B and FIG. 1C show the probe hybridized to a wide-type target and a mutant type target, respectively. After hybridization, the fluorescence emission from the silver nanoclusters is enhanced (the probe "lights up") because the nanoclusters which are templated onto the nucleation sequence are brought into proximity with the guanine(s) from the enhancer sequence. As discussed in more detail herein, by altering the alignment of the metal nanoclusters with the enhancer sequence, the emission wavelength of light emitted from the nanoclusters can be altered.

The association of the metal nanoclusters on the first probe with the enhancement portion of the second probe can increase the fluorescence emission of the templated metal nanoclusters by at least 2-fold fold. In a related aspect, the association of the metal nanoclusters on the first probe with the enhancement portion of the second probe can increase the fluorescence emission of the templated metal nanoclusters from about 2-fold to about 500-fold (such as about 2, 3, 4, 5, 6, 7, 8, 9, 10, 20, 30, 40, 50, 60, 70, 80, 90, 100, 125, 150, 175, 200, 225, 250, 275, 300, 325, 350, 375, 400, 425, 450, 475 or 500-fold).

Detection of fluorescence emission can be performed according to known methods, for example as described herein. The excitation light can be selected from the group consisting of ultraviolet light, visible light, near infrared light or a combination thereof. In a related aspect, the wavelength of excitation light is from 200 nm to 2000 nm (or 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1050, 1100, 1150, 1200, 1250, 1300, 1350, 1400, 1450, 1500, 1550, 1600, 1650, 1700, 1750, 1800, 1850, 1900, 1950 or 2000 nm).

C. Test and Control Nucleic Acid Molecules

The nucleic acid molecules analyzed can be single- or double-stranded, though certain embodiments employ double-stranded nucleic acids, such as dsDNA molecules. The method is not limited to detection sequence variability between or among dsDNA molecules, however. For example (and without limitation), sequence variations in single-stranded mRNA molecules can be analyzed by using complementary RNA or DNA molecules to determine the melting profiles of the mRNAs based on the corresponding dsRNA or dsRNA/DNA hybrid molecules.

The test and control nucleic acid molecules can be obtained from any suitable source and can be of any type, such as being isolated from a subject or obtained from another party that has isolated the nucleic acid. The size of the nucleic acids analyzed also can vary. For example, the target nucleic acid sequence can be any length, such as at least 20 nucleotides (such as at least 30, 40, 50, 60, 70, 80, 90, 100, 150, 200, 300, 400, 500, 600, 700, 800, 900, or at least 1000 or more nucleotides) in length. In some embodiments, the target nucleic acid sequence can also have a maximum length, such as no more than 1000 nucleotides (such as no more than 500, 300, 200, 100, 90, 80, 70, 60, 50, 40, 30, or no more than 20 nucleotides in length). In some embodiments, the target nucleic acid sequence is genomic DNA. The test and control nucleic acids can be selected according to a particular characteristic. For example, genomic sequences located near markers for genetic disease can be analyzed to detect sequence variation among wild-type and mutant forms, or a nucleic acid can be selected based on nucleotide composition.

Additionally, the test and control nucleic acids can be processed or manipulated, such as being amplified, digested by restriction endonucleases, or labeled. In some embodiments, the nucleic acids are diluted in one or more solutions, arranged in an array, and/or placed on a solid substrate (for example, a DNA microchip). In certain embodiments, the nucleic acids are diluted in an organic or inorganic solvent to form solutions. The solution optionally can contain additives, such as stabilizers, preservatives, or buffers.

In some embodiments, the target nucleic acid molecule is a gene sequence or fragment thereof. For example, the target nucleic acid molecule can be a nucleotide sequence of the β-globin gene (GeneID: 3043), v-Ki-ras2 Kirsten rat sarcoma viral oncogene homolog (KRAS) gene (GeneID: 3845), v-raf murine sarcoma viral oncogene homolog B1 (BRAF) gene (GeneID: 673), hexosaminidase A (HEXA) gene (GeneID: 3073), p53 gene (GeneID: 7157), Werner syndrome, RecQ helicase-like (WRN) gene (GeneID: 7486), factor-associated suicide (FAS) gene (GenBank Acc. No. M67454), fat mass and obesity associates (FTO) gene (GeneID: 79068), and transcription factor 7-like 2 (TCF7L2) gene (GeneID: 6934), or a fragment thereof. In some embodiments, the target nucleic acid molecule comprises or consists of the nucleotide sequence set forth as one of SEQ ID NOs: 19-22, 31-34, 43-46, 63, 64, 67, 68, 71, 72, 75, 76, 79, 80, 89 and 90.

Prior knowledge about the existence of any variation among the sequences is not necessary. In fact, determining melting profiles and detecting differences between or among the corresponding nucleic acids can be accomplished without any prior knowledge about the existence of any variant sequence, such as an SNP, small insertion, small deletion, or small inversion.

D. Exemplary Disorders and Polymorphisms

The disclosed methods are useful for the detection of polymorphisms that are indicative of a particular disease or condition. Therefore, the disclosed methods can be used to diagnose a subject with a particular disease or condition by detecting a polymorphism in a sample from that subject that is indicative of the disease or condition. In some embodiments, a subject is selected for testing that has, or is suspected of having, the disease or condition.

1. Tay-Sachs Disease

Tay-Sachs disease, also known as GM2 gangliosidosis or hexosaminidase A deficiency, is a rare autosomal recessive genetic disorder. In its most common variant, known as infantile Tay-Sachs disease, it causes a progressive deterioration of nerve cells and of mental and physical abilities that commences around six months of age and usually results in death by the age of four. The disease occurs when harmful quantities of cell membrane components known as gangliosides accumulate in the brain's nerve cells, eventually leading to the premature death of the cells. A ganglioside is a form of sphingolipid, which makes Tay-Sachs disease a member of the sphingolipidoses. There is no known cure or treatment.

Tay-Sachs results from mutations in the HEXA gene on human chromosome 15, which encodes the alpha-subunit of beta-N-acetylhexosaminidase A, a lysosomal enzyme. By 2000, more than 100 different mutations had been identified in the human HEXA gene. Each of these mutations alters the gene's protein product (i.e., the enzyme), sometimes severely inhibiting its function. These mutations have included single base insertions and deletions, splice phase mutations, missense mutations, and other more complex patterns. The most common polymorphism in Tay-Sachs disease is SNP ID: Rs28940871.

Methods of identifying a subject with, or suspected of having, Tay-Sachs disease are known in the art. For example, one test for Tay-Sachs involves an enzyme assay that measures hexosaminidase activity in serum, fibroblasts or leukocytes. Total hexosaminidase enzyme activity is decreased in individuals with Tay-Sachs as is the percentage of hexosaminidase A. After confirmation of decreased enzyme activity in an individual, confirmation by molecular analysis can be pursued. Patients with infantile onset Tay-Sachs disease have a "cherry red" macula in the retina, easily observable by a physician using an ophthalmoscope. This red spot is a retinal area that appears red because of gangliosides in the surrounding retinal ganglion cells. Unlike other lysosomal storage diseases (e.g., Gaucher disease, Niemann-Pick disease, and Sandhoff disease), hepatosplenomegaly (liver and spleen enlargement) is not seen in Tay-Sachs.

2. Li-Fraumeni Syndrome

Li-Fraumeni syndrome is a rare autosomal dominant hereditary disorder that greatly increases susceptibility to cancer. This syndrome is also known as the Sarcoma, breast, leukemia and adrenal gland (SBLA) syndrome. The syndrome is linked to germline mutations of the p53 tumor suppressor gene, which normally helps control cell growth. The mutations may be inherited or may arise de novo early in embryogenesis, or in one of the parent's germ cells. The most common polymorphism in Li-Fraumeni syndrome is SNP ID: Rs28934578.

The TP53 gene is responsible for initiating DNA repair mechanisms and/or apoptosis upon detection of DNA damage. Thus, Li-Fraumeni syndrome, with one of the two p53 copies already mutated, predisposes a person to cancer development because only one additional mutation (in the second p53 allele) is necessary to impair a significant portion of the tumor suppressor system. This "second hit", which can be affected by environmental factors, can directly lead to both p53 alleles being impaired and thus potentiate cancer development. Methods of identifying a subject with, or suspected of having, Li-Fraumeni syndrome are known in the art. Persons with Li-Fraumeni syndrome have an approximately 25-fold increased risk of developing a malignant tumor by age 50 than the population average, and are at risk for a wide range of malignancies, with particularly high occurrences of breast cancer, brain tumors, acute leukemia, soft tissue sarcomas, bone sarcomas, and adrenal cortical carcinoma.

3. Werner's Syndrome

Werner syndrome (WS), also known as "adult progeria" is a rare, autosomal recessive progeroid syndrome (PS), which is characterized by the appearance of premature aging. Affected individuals typically grow and develop normally until puberty; the mean age of diagnosis is twenty-four, often realized when the adolescent growth spurt is not observed. The median and mean age of death is 47-48 and 54 years, respectively; the main course of death is cardiovascular disease or cancer.

Methods of identifying a subject with, or suspected of having, Werner syndrome are known in the art. For example, the appearance of affected individuals is abnormal. They exhibit growth retardation, short stature, premature graying of hair, alopecia (hair loss), wrinkling, prematurely aged face with a beaked nose, skin atrophy (wasting away) with scleroderma-like lesions, lipodystrophy (loss of fat tissues), abnormal fat deposition leading to thin legs and arms, and severe ulcerations around the Achilles tendon and malleoli (around ankles). Other medical signs include change in voice (weak, hoarse, high-pitched), atrophy of gonads leading to reduced fertility, bilateral cataract (clouding of lens), premature arteriosclerosis (thickening and loss of elasticity of arteries), calcinosis (calcium deposits in blood vessels), atherosclerosis (blockage of blood vessels), type 2 diabetes, osteoporosis (loss of bone mass), telangiectasia, and malignancies. In fact, the prevalence of rare cancers, such as meningiomas, increases in individuals with Werner syndrome.

Approximately 90% of individuals presenting Werner syndrome have any of a range of mutations in the eponymous gene, WRN; the only gene currently attributed to cause Werner syndrome. WRN, which lies on chromosome 8 in humans, encodes the WRNp protein, a 1432 amino acid protein with a central domain resembling members of the RecQ helicases. WRNp is active in unwinding DNA, a step necessary in DNA repair and DNA replication. Since WRNp's function depends on DNA, it is only functional when localized to the nucleus.

Mutations which cause Werner syndrome all occur at the regions of the gene which encode for protein, and not at non-coding regions. The most common polymorphism in Werner syndrome is SNP ID: rs17847577. These mutations can have a range of effects. They may decrease the stability of the transcribed messenger RNA (mRNA), which increases the rate at which they are degraded. With less mRNA, less is available to be translated into the WRNp protein. Mutations may also lead to the truncation (shortening) of the WRNp protein leading to the loss of its nuclear localization signal sequence, thus it is no longer transported into the nucleus where it interacts with the DNA. This leads to a reduction in DNA repair. Furthermore, mutated proteins are more likely to be degraded than normal WRNp. Apart from causing defects in DNA repair, its aberrant association with p53 down-regulates the function of p53, leading to a reduction in p53-dependent apoptosis and increase the survival of these dysfunctional cells.

4. Type-2 Diabetes

Diabetes mellitus type 2 is a metabolic disorder that is characterized by high blood glucose in the context of insulin resistance and relative insulin deficiency. The classic symptoms are excess thirst, frequent urination, and constant hunger. Obesity is thought to be the primary cause of type 2 diabetes in people who are genetically predisposed to the disease.

As of 2011, more than 36 genes have been found that contribute to the risk of type 2 diabetes. All of these genes together still only account for 10% of the total heritable component of the disease. The TCF7L2 allele, for example, increases the risk of developing diabetes by 1.5 times and is the greatest risk of the common genetic variants. Most of the genes linked to diabetes are involved in beta cell functions. There are a number of rare cases of diabetes that arise due to an abnormality in a single gene (known as monogenic forms of diabetes or "other specific types of diabetes"). These include maturity onset diabetes of the young (MODY), Donohue syndrome, and Rabson-Mendenhall syndrome, among others. Maturity onset diabetes of the young constitutes 1-5% of all cases of diabetes in young people. A common polymorphism in Type-2 diabetes is SNP ID Rs9939609.

Methods of identifying a subject with, or suspected of having, type-2 diabetes are known in the art. The World Health Organization definition of diabetes is for a single raised glucose reading with symptoms, otherwise raised values on two occasions, of either: fasting plasma glucose ≥7.0 mmol/l (126 mg/dl) or with a glucose tolerance test, two hours after the oral dose a plasma glucose ≥11.1 mmol/l (200 mg/dl). A random blood sugar of greater than 11.1 mmol/l (200 mg/dL) in association with typical symptoms or a glycated hemoglobin (HbA$_{1c}$) of greater than 6.5% is another method of diagnosing diabetes. In 2009 an International Expert Committee that included representatives of the American Diabetes Association (ADA), the International Diabetes Federation (IDF), and the European Association for the Study of Diabetes (EASD) recommended that a threshold of ≥6.5% HbA$_{1c}$, should be used to diagnose diabetes. This recommendation was adopted by the American Diabetes Association in 2010. Positive tests should be repeated unless the person presents with typical symptoms and blood sugars >11.1 mmol/l (>200 mg/dl).

5. Additional Embodiments

The methods and probes disclosed herein can be used to detect the SNPs disclosed in the following references, each of which is incorporated by reference herein in its entirety: Kwok et al., *Ann. Rev. Genomics Hum. Genetics* 2001, 2, 235; Tian et al., Chen, J. Q. *Nature* 2008, 455, 105; Wilentz et al., *Cancer* 1998, 82, 96; Wang et al., *Science* 1998, 280, 1077; Kostrikis et al., *Science* 1998, 279, 1228; Zhong et al., *Proc. Natl. Acad. Sci. U.S.A.* 2003, 100, 11559; Kolpashchikov et al., *J. Am. Chem. Soc.* 2005, 127, 12442; Xiao et al., *Chem. Int. Ed.* 2009, 48, 4354; Park et al., *Science* 2002, 295, 1503; Star et al., *Proc. Natl. Acad. Sci. U.S.A.* 2006, 103, 921; Boon et al., *Nat. Biotechnol.* 2000, 18, 1096; Inouye et al., *Proc. Natl. Acad. Sci. U.S.A.* 2005, 102, 11606; Mhlanga et al., *Methods* 2001, 25, 463; de Kok et al., *Hum. Mutation* 2002, 19, 554; Okamoto et al., *J. Am. Chem. Soc.* 2004, 126, 4820.

VI. Kits

The probes and reagents disclosed herein can be supplied in the form of a kit for use in an assay to identify or characterize a test nucleic acid molecule. In such a kit, an appropriate amount of one or more of the probes disclosed herein, for example a probe comprising or consisting of the sequence set forth as one of SEQ ID NOs: 23-30, 35-42, 47-54, 65-66, 69-70, 73-74, 77-78, or 81-82 are provided in one or more containers. A nucleic acid probe may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, ampoules, or bottles. For probes including a nucleation sequence, the probe can include templated metal nanoclusters. Control reagents, such as control nucleic acid molecules can also be included.

In some embodiments, the kit can include a first probe and a second probe, wherein the first and second probes comprise or consist of nucleotide sequences set forth as:

(a) one of SEQ ID NOs: 23-26 and one of SEQ ID NOs: 27-30, respectively;

(b) one of SEQ ID NOs: 35-38 and one of SEQ ID NOs: 39-42, respectively;

(c) one of SEQ ID NOs: 47-50 and one of SEQ ID NOs: 51-54, respectively;

(d) SEQ ID NO: 65 and SEQ ID NO: 67, respectively;

(e) SEQ ID NO: 69 and SEQ ID NO: 70, respectively;

(f) SEQ ID NO: 73 and SEQ ID NO: 74, respectively;

(g) SEQ ID NO: 77 and SEQ ID NO: 78, respectively; or (h) SEQ ID NO: 81 and SEQ ID NO: 82, respectively.

In some examples, one or more sets of probes, may be provided in pre-measured single use amounts in individual, typically disposable, tubes or equivalent containers. With such an arrangement, the sample to be tested for the presence of the target nucleic acids can be added to the individual tube(s) and amplification carried out directly.

The amount of nucleic acid probe supplied in the kit can be any appropriate amount, and may depend on the target market to which the product is directed. For instance, if the kit is adapted for research or clinical use, the amount of each nucleic acid primer provided would likely be an amount sufficient to prime several detection reactions. General guidelines for determining appropriate amounts may be found in Innis et al., Sambrook et al., and Ausubel et al.

In some embodiments, kits also may include the reagents necessary to carry out fluorescence detection assays, including sample preparation reagents, appropriate buffers, salts, tubes or assay cells.

In other particular embodiments, the kit includes equipment, reagents, and instructions for extracting and/or purifying nucleic acid molecules from a sample.

EXAMPLES

The following examples are provided to illustrate particular features of certain embodiments, but the scope of the claims should not be limited to those features exemplified.

Example 1

Preparation of DNA-Templated Metal Nanoclusters and Enhancer Sequences

This example provides methods for preparing metal nanoclusters (e.g., silver) on nucleic acid molecules (e.g., DNA) and enhancer sequences.

All DNA probes used herein were synthesized by INTEGRATED DNA TECHNOLOGIES INCORPORATED and were purified by desalting. DNA-templated silver nanoclusters were synthesized using the protocol developed by Petty and coworkers (Ritchie et al., *J. Phys. Chem. C,* 2007, 111, 175), which is incorporated by reference in its entirety. Briefly, nanocluster-bearing probes were first dissolved in ultrapure deionized water. Silver nanoclusters ("Ag NCs") were formed by adding $AgNO_3$ (99.9%, Sigma-Aldrich) to the DNA solution, followed by reduction with $NaBH_4$. Final concentrations were 15 μM in NC-bearing probe, 180 μM in $AgNO_3$, and 180 μM in $NaBH_4$ in 20 mM pH 6.6 sodium phosphate buffer. The aqueous solution of $NaBH_4$ was prepared by dissolving $NaBH_4$ powder in water and adding the required volume to the $DNA/Ag^+$ mixture within 30 seconds, followed by vigorous shaking for 5 seconds. The reaction was kept in the dark at room temperature for 18 hours before use. Probe-target hybridization was also carried out in 20 mM pH 6.6 sodium phosphate buffer at a 1:1 probe/target ratio. The sample was heated to 95° C. for 45 seconds and then slowly cooled to and kept at room temperature for an hour.

Fluorescence emission was measured using a VARIAN CARY ECLIPSE fluorescence spectrophotometer. A long pass filter (FF01-409/LP, SEMROCK) was placed in the emission light path in order to eliminate a second order diffraction peak of the excitation source in the emission spectrum scan. Absorbance was measured using an AGILENT 8453 UV/Visible spectrophotometer and a cuvette (16.100E-Q-10/z15, STARNA CELLS) having 1 cm path length. Images of samples were acquired using a digital camera (Model no. C-770 ultra zoom, OLYMPUS) with the samples illuminated by 365 nm light provided by a SYNGENE InGenius gel imager.

Table 2 below provides the nucleic acid sequences of example oligonucleotides used to prepare probes having silver nanoclusters. The nucleotides of the sequences shown in table 2 below that acted as the NC-nucleation or enhancer sequence are shown in bold type font. The SNP sites and the nucleotides designed to generate frame-shift base pairing are italicized.

TABLE 2

| SEQ ID NO: | Name of probe | Sequence (5'-3') | Length (nts.) |
|---|---|---|---|
| 1 | NC-bearing stand | CCC TTAAT CCCC TAT AAT AAA TTT TAA ATA TTA TTT ATT AAT | 42 |
| 2 | Probe_H | TAT AAT AAA TTT TAA ATA TTA TTT ATT AAT | 30 |
| 3 | Probe NC | CCC TTA ATC CCC | 12 |
| 4 | G-rich portion_1 | GGGTGGGGTGGGGTGGGG | 18 |
| 5 | G-rich probe_"-3" | ATT AAT AAA TAA TAT TTA AAA TTT ATT ATA ATA GGGTGGGGTGGGGTGGGG | 51 |
| 6 | G-rich probe_"-2" | ATT AAT AAA TAA TAT TTA AAA TTT ATT ATA TA *GGGTGGGGTGGGGTGGGG* | 50 |
| 7 | G-rich probe_"-1" | ATT AAT AAA TAA TAT TTA AAA TTT ATT ATA A *GGGTGGGGTGGGGTGGGG* | 49 |
| 8 | G-rich probe_"0" | ATT AAT AAA TAA TAT TTA AAA TTT ATT ATA GGGTGGGGTGGGGTGGGG | 48 |
| 9 | G-rich probe_"+1" | ATT AAT AAA TAA TAT TTA AAA TTT ATT AT GGGTGGGGTGGGGTGGGG | 47 |
| 10 | G-rich probe_"+2" | ATT AAT AAA TAA TAT TTA AAA TTT ATT A GGGTGGGGTGGGGTGGGG | 46 |
| 11 | G-rich probe_"+3" | ATT AAT AAA TAA TAT TTA AAA TTT ATT GGGTGGGGTGGGGTGGGG | 45 |
| 12 | G-rich probe_"+4" | ATT AAT AAA TAA TAT TTA AAA TTT AT GGGTGGGGTGGGGTGGGG | 44 |

TABLE 2-continued

| SEQ ID NO: | Name of probe | Sequence (5'-3') | Length (nts.) |
|---|---|---|---|
| 13 | G-rich probe_"+5" | ATT AAT AAA TAA TAT TTA AAA TTT A GGGTGGGGTGGGGTGGGG | 43 |
| 14 | G-rich probe_"+6" | ATT AAT AAA TAA TAT TTA AAA TTT GGGTGGGGTGGGGTGGGG | 42 |
| 15 | G-rich probe_"+7" | ATT AAT AAA TAA TAT TTA AAA TT GGGTGGGGTGGGGTGGGG | 41 |
| 55 | NC probe_3 | CCC TTAAT CCCC GTGT CAG CTC CAA CTA CCA CAA GTT TAT | 40 |
| 56 | G-rich probe_3 | TCA AGG CAC TCT GCC CTA CGC CA CACA GGGTGGGGTGGGGTGGGG | 45 |
| 57 | Heteropolymer enhancer probe | ATT AAT AAA TAA TAT TTA AAA TTT ATT ATA TTGGTTGGTTGGTTGGTT | 48 |
| 58 | NC-bearing probe_"-1" | CCC TTAAT CCCC AT AAT AAA TTT TAA ATA TTA TTT ATT AAT | 41 |
| 59 | NC-bearing probe_"0" | CCC TTAAT CCCC TAT AAT AAA TTT TAA ATA TTA TTT ATT AAT | 42 |
| 60 | NC-bearing probe_"+1" | CCC TTAAT CCCC T TAT AAT AAA TTT TAA ATA TTA TTT ATT AAT | 43 |
| 61 | NC-bearing probe_"+2" | CCC TTAAT CCCC TT TAT AAT AAA TTT TAA ATA TTA TTT ATT AAT | 44 |
| 62 | NC-bearing probe_"+3" | CCC TTAAT CCCC TTT TAT AAT AAA TTT TAA ATA TTA TTT ATT AAT | 45 |

Example 2

Alignment of DNA-Templated Metal Nanoclusters with Enhancer Sequence Determines Fluorescence Emission Color This example shows that the fluorescence emission color of a nucleic acid probe having silver nanoclusters (NC-nucleation sequence) brought in proximity to the enhancer sequence can change (a shift of from about 60 nm to about 70 nm) depending on the alignment of the NC-nucleation sequence with the enhancer sequence.

Figure 2A:
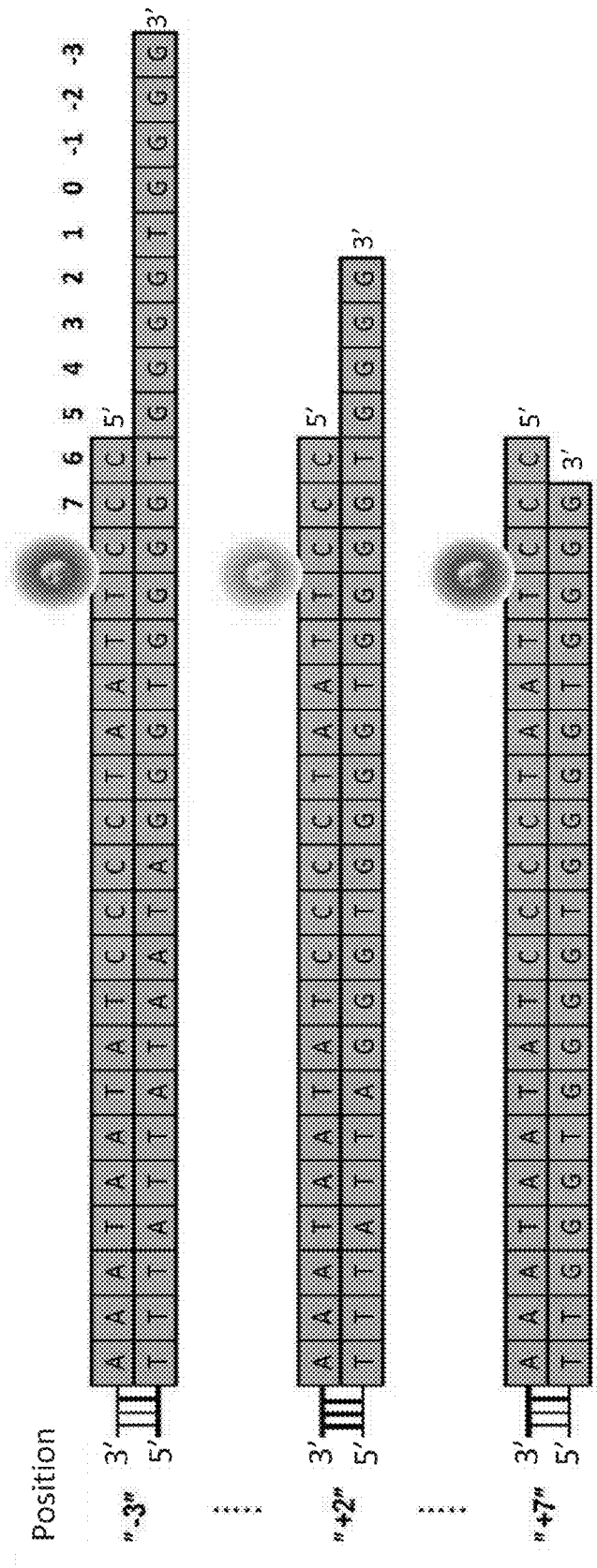
FIGS. 2A and 2B show three different alignments ("−3", "+2" and "+7") of the same NC-sequence (upper strand; SEQ ID NO: 3) and enhancer sequence (lower strand; SEQ ID NO: 4) and a cartoon of the effect the alignment has on fluorescence emission color, with a red light-up color for positions "−3" and "+7", and a yellow/orange color for position "+2".
Figure 2B:
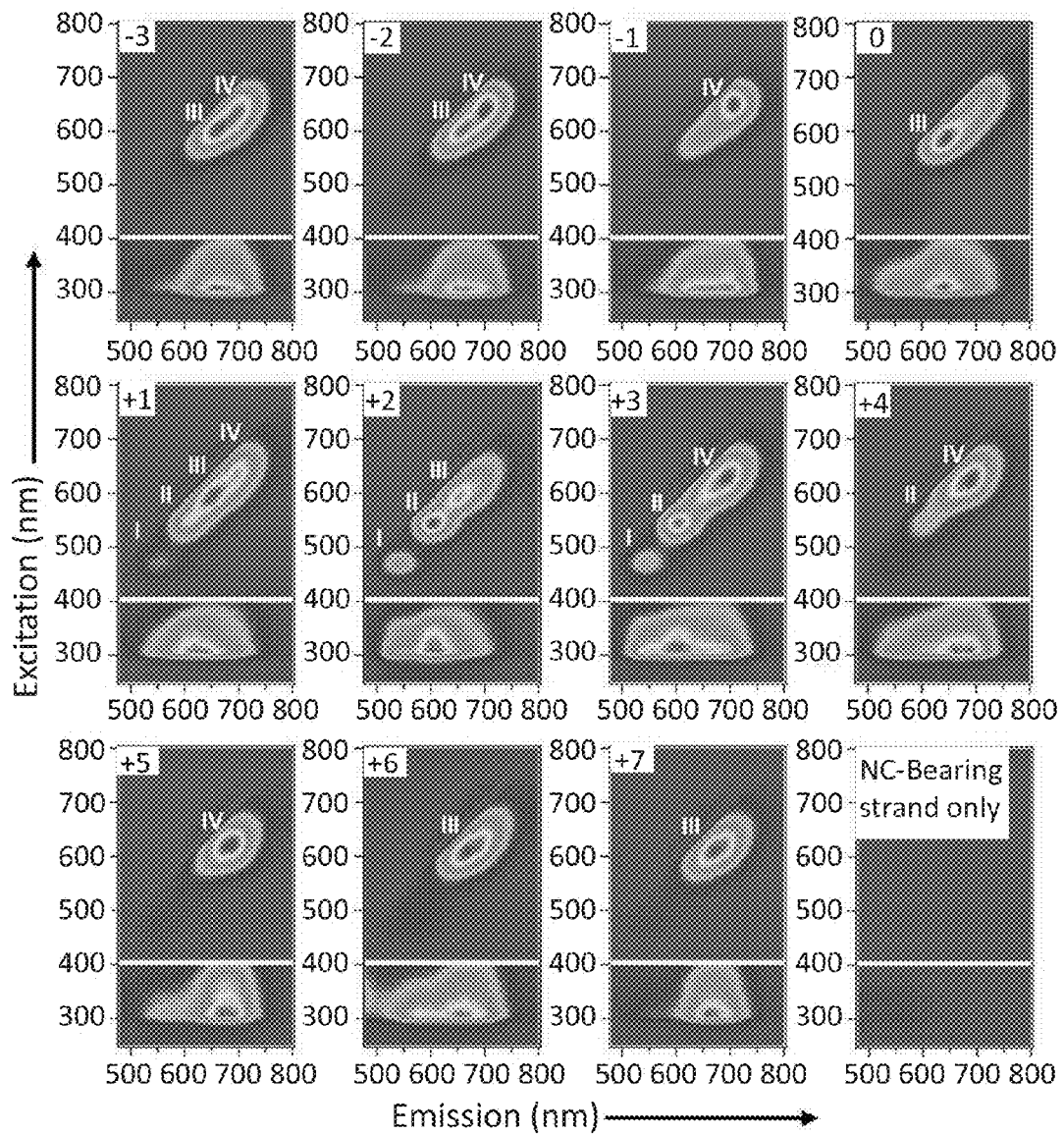

Different light-up colors can be obtained from the same NC-nucleation sequence (which carries a non-emissive Ag NC) and the same enhancer sequence by changing the position of the enhancer relative to the NC-nucleation sequence. As shown in FIG. 2A different relative positions between the enhancer sequence and the NC-nucleation sequences (named "position −3" to "position +7") were produced by hybridizing a common NC-bearing probe (SEQ ID NO: 1) shown in table 2, which carried non-emissive Ag NC) with 11 different guanine-rich (G-rich) probes (SEQ ID NOs: 5-15) shown in table 2, which had a common enhancer sequence (SEQ ID NO: 4). The longest G-rich probe (G-rich probe "−3") contained 51 bases, with each subsequent G-rich probe shortened by one nucleotide. SEQ ID NO: 1 comprises the 12 nucleic acid nanocluster nucleation sequence (5'-CCCTTAATCCCC-3'; SEQ ID NO: 88) designed by Richards et al. (see: Richards et al., "Oligonucleotide-Stabilized Ag Nanocluster Fluorescence," Journal of the American Chemical Society, April 2008, vol. 130, pp. 5038-5039, incorporated by reference.

The 2D fluorescence contour plots (FIG. 2B) show the hybridized samples generated multiple spectral peaks when excited in the visible to near-infrared region (450-800 nm). Corresponding to different light-up nanocluster species, these spectral peaks (called visible excitation peaks) could be categorized into four groups. Other than visible excitation peaks, UV excitation peaks appeared in the UV excitation region (250-400 nm, shown in the lower portion of the 2D plots with an independent intensity scale). In dilute solutions, the UV excitation spectra of DNA/Ag NCs are well matched to absorption spectra of DNA (using short path length cuvettes). Moreover, the fluorescence emission of DNA/Ag NCs upon UV excitation is highly depolarized, suggesting a rapid energy transfer mechanism between the bases and the Ag NCs. Here, a similar mechanism is most likely responsible for the UV excitation features was observed (FIG. 2B), albeit the UV excitation maxima in our spectra (ca. 300 nm) are red-shifted from the absorption maxima of the bases (ca. 260 nm). This red shift is due to the strong absorption of 260 nm light by the DNA bases. The 260 nm light is heavily attenuated by the time it reaches the center of the 1 cm cuvette. Having similar UV excitation peaks for all Ag nanocluster species templated on DNA (regardless of their emission color) is a useful feature for either multiplexed assays or homogeneous assays that employ a broad spectrum of fluorescent nanoclusters.

Figure 3A:
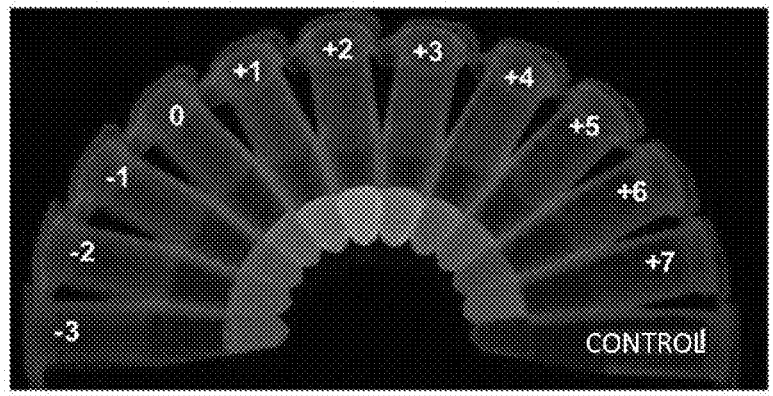
FIGS. 3A-3C show light emission color of cNCBs can be tuned by repositioning the enhancer sequence with respect to the NC-nucleation sequence (SEQ ID NO: 3).
Figure 3B:
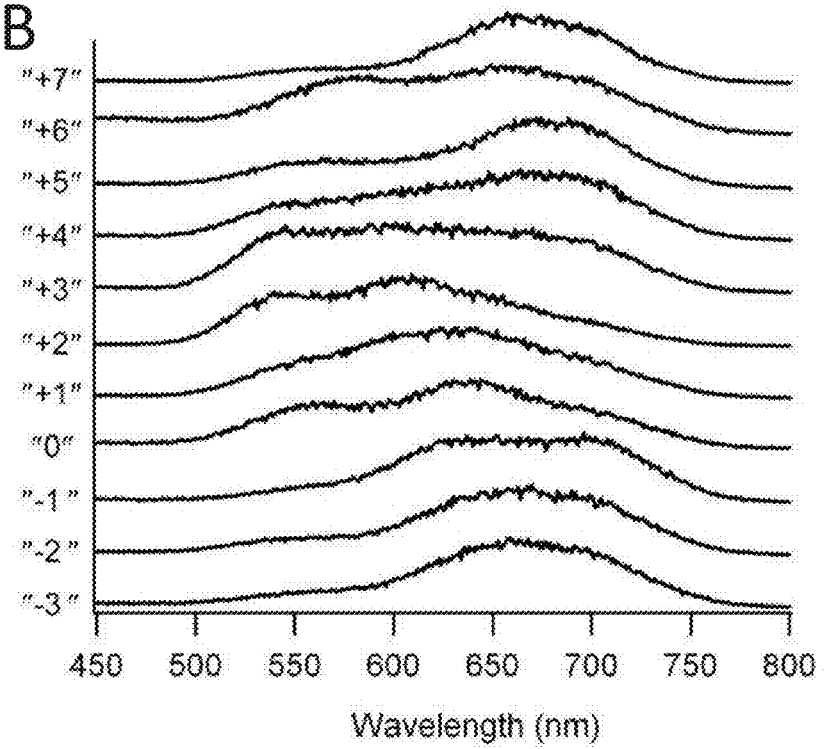
Figure 3C:
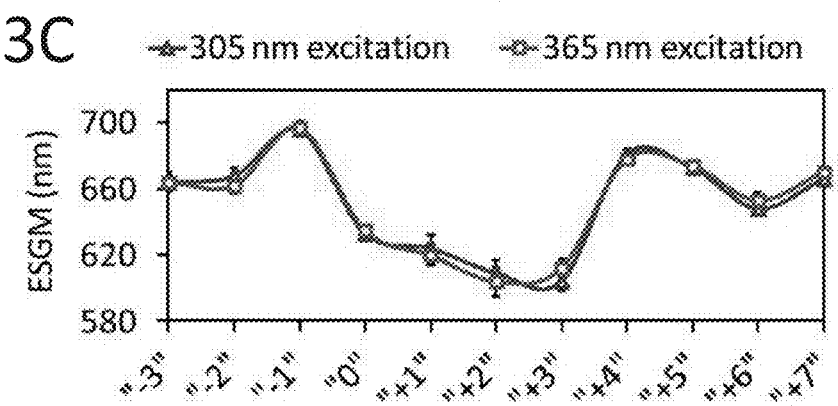

NCs can be seen under UV light (FIG. 3A). Visible excitation peaks were well resolved, symmetric, and distributed diagonally in the 2D fluorescence contour plots, whereas the UV excitation peaks were poorly resolved, asymmetric, and distributed horizontally. Despite these differences, the profiles of the UV excitation spectra reflect, to some extent, the types and the relative populations of light-up nanocluster species produced in individual samples. As a result, differences in the fluorescence emission color can be visualized among the 11 samples under UV 365 nm excitation (FIG. 3A). The colors of position +1, +2, and +3 samples were blue shifted, mainly due to the presence of type I and type II light-up nanocluster species in these samples. The samples were in 1.5 ml EPPENDORF tubes and were placed on a commercial gel imager. The image was acquired by a digital camera and presented here without any contrast/color adjustment. The color variation is more clearly seen in FIG. 3B, where the emission spectra are plotted. The emission-spectrum-global-maximum (ESGM, defined as the wavelength where the emission spectrum is the highest) was used as a gross indicator of color for each sample (FIG. 3C). While the exact separation distance between the Ag NC and the enhancer sequence in each position was not initially known, subtle repositioning of the enhancer sequence relative to the NC-nucleation sequence (e.g., from position −1 to 0 or from position +3 to +4) can shift the ESGM by as much as 60-70 nm (FIG. 3C). The ability to obtain measurably different fluorescent read out using the same enhancer sequence shifted only by a single nucleotide is unique to NCBs. It is an environmental sensitivity not seen in organic dyes or semiconductor quantum dots that opens the door to the creation of a new type of probe that can sense small variations in DNA sequences.

Figure 4A:
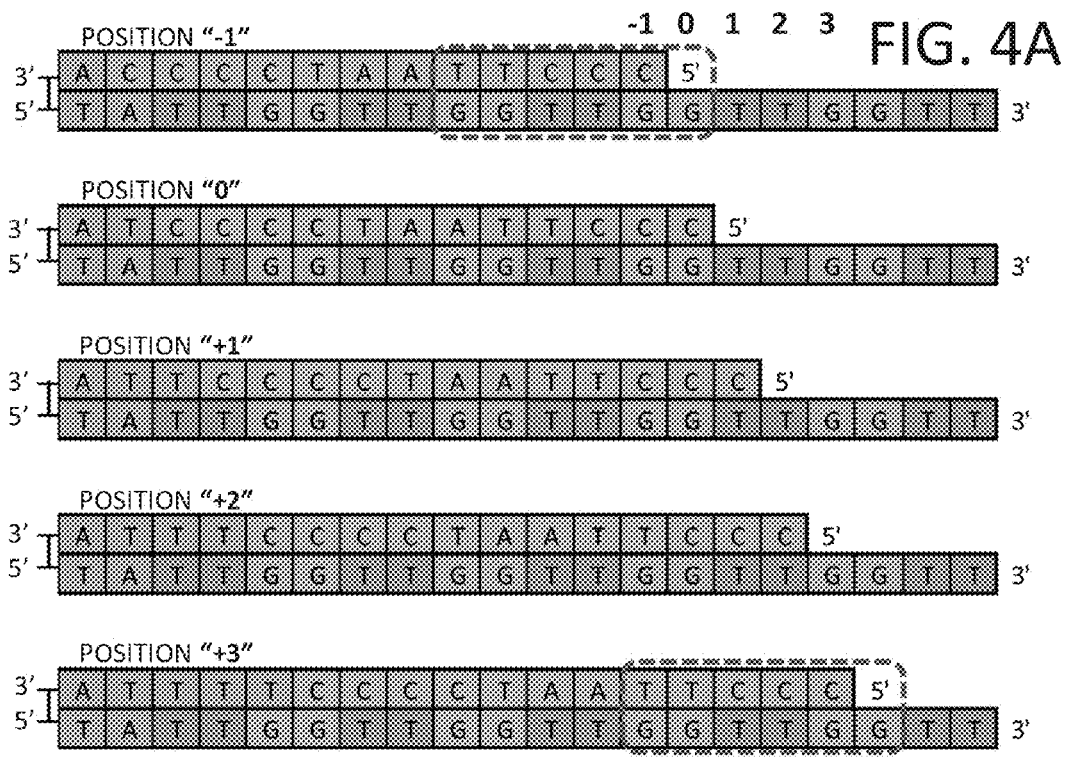
FIGS. 4A and 4B show the effect of repositioning the alignment of an enhancer probe relative to a nanocluster-bearing probe. Five hybridized samples were prepared. Each sample included a common heteropolymer enhancer probe (SEQ ID NO: 57) with five different nanocluster bearing probes (SEQ ID NOs: 58-62). The hybridization alignment between the enhancer probe and each of the five nanocluster bearing probes differs by the advancement along the enhancer sequence, one nucleotide at a time. This creates five different alignment positions between the enhancer probe and the five different NC-bearing sequences.
Figure 4B:
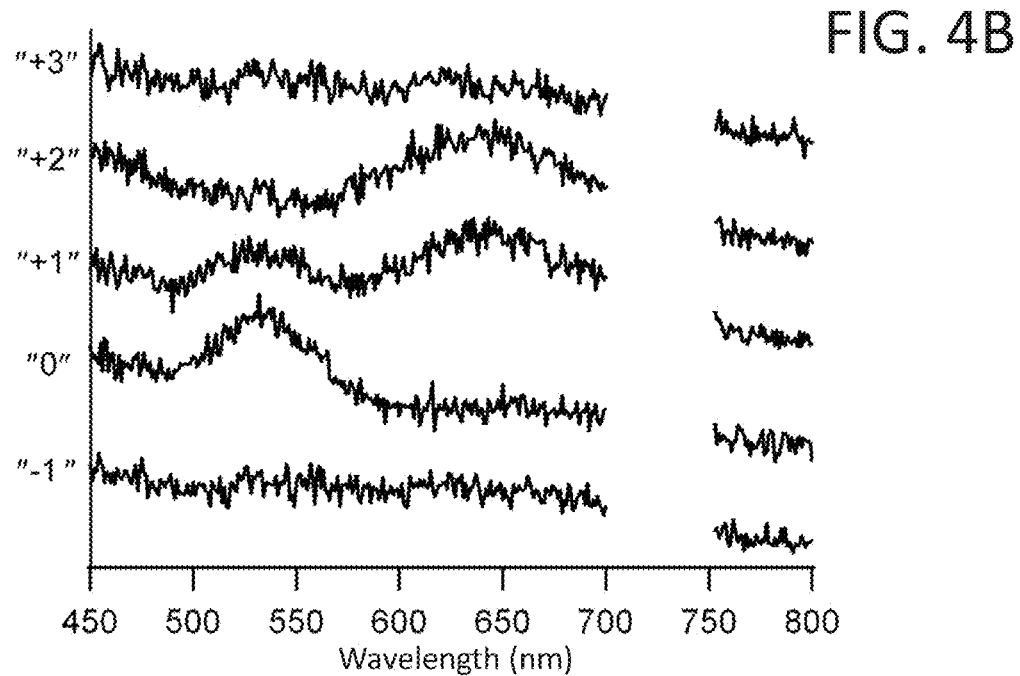

Further, a heteropolymer enhancer with periodic $T_2$ and $G_2$ content (e.g., 5'-$T_2$-$(G_2T_2)_4$-3'), depending upon the relative position between the NC-nucleation and the heteropolymer enhancer sequences, cycles the emission between green and red (see FIGS. 4A and 4B). Color switching between green and red suggests that a very short-range interaction (potentially direct contact) between the enhancer bases and the Ag NC determines the emission color of Ag NC. Due to this short-range interaction, it is not surprising that a 100 nm shift in ESGM from position 0 to position +1 (FIG. 4B), corresponding to the spectral separation between the green (535 nm) and red (636 nm) light-up nanocluster species previously identified.

FIGS. 2A and 4A are schematics to guide potential understanding and may not reflect the true alignment between the NC-nucleation sequence and the enhancer sequence.

The large ESGM shifts seen upon a change in alignment by two nucleotides between the NC-probe and the enhancer probe was exploited to directly and quantitatively identify disease related SNPs.

Example 3

Detection of Single-Nucleotide Substitutions in Kras Nucleotide Sequences with cNCBs This example shows that cNCBs detect single-nucleotide substitutions in different Kras nucleotide sequence targets. This example validates the application of these probes as a tool for detecting SNPs related to disease states and conditions in subjects.

Table 3 below provides the nucleic acid sequences of the target sequences (wild-type or "wt" sequence) used as a reference for comparison to the test sequences (disease carrier sequence contain a SNP or "mt") and the associated NC-nucleation ("NC-probe") and enhancer ("G-rich probe") sequences. The NC-nucleation and enhancer sequences are shown in bold type font. The SNP sites and the nucleotides designed to generate frame-shift base pairing are italicized.

TABLE 3

| SEQ ID NO: | Name of probe | Sequence (5'-3') | Length (nts.) |
|---|---|---|---|
| 16 | NC probe_1 | CCC TTAAT CCCC GAGA CAG CTC AAA CTA CCA CAA GTT TAT | 40 |
| 17 | NC probe_2 | CCC TTAAT CCCC T GAGA CAG CTC AAA CTA CCA CAA GTT TAT | 41 |
| 18 | G-rich probe_1 | TCA AGG CAC TCT TGC CTA CGC CA CTCT GGGTGGGGTGGGGTGGGG | 45 |
| 19 | Kras G wt target | CTG AAT ATA AAC TTG TGG TAG TTG GAG CTG G TG G*C*G TAG GCA AGA GTG CCT TGA CGA TAC | 60 |
| 20 | Kras T mt target | CTG AAT ATA AAC TTG TGG TAG TTG GAG CTG T TG G*C*G TAG GCA AGA GTG CCT TGA CGA TAC | 60 |
| 21 | Kras C target | CTG AAT ATA AAC TTG TGG TAG TTG GAG CTG C TG GCG TAG GCA AGA GTG CCT TGA CGA TAC | 60 |
| 22 | Kras A target | CTG AAT ATA AAC TTG TGG TAG TTG GAG CTG A TG GCG TAG GCA AGA GTG CCT TGA CGA TAC | 60 |
| 23 | Kras NC probe g | CCC TTAAT CCCC *G* CAG CTC AAA CTA CCA CAA GTT TAT | 37 |
| 24 | Kras NC probe t | CCC TTAAT CCCC *T* CAG CTC AAA CTA CCA CAA GTT TAT | 37 |
| 25 | Kras NC probe c | CCC TTAAT CCCC *C* CAG CTC AAA CTA CCA CAA GTT TAT | 37 |
| 26 | Kras NC probe a | CCC TTAAT CCCC *A* CAG CTC AAA CTA CCA CAA GTT TAT | 37 |

TABLE 3-continued

| SEQ ID NO: | Name of probe | Sequence (5'-3') | Length (nts.) |
|---|---|---|---|
| 27 | Kras G-rich probe g | TCA AGG CAC TCT TGC CTA CGC CA G GGGTGGGGTGGGGTGGGG | 42 |
| 28 | Kras G-rich probe t | TCA AGG CAC TCT TGC CTA CGC CA T GGGTGGGGTGGGGTGGGG | 42 |
| 29 | Kras G-rich probe c | TCA AGG CAC TCT TGC CTA CGC CA C GGGTGGGGTGGGGTGGGG | 42 |
| 30 | Kras G-rich probe a | TCA AGG CAC TCT TGC CTA CGC CA A GGGTGGGGTGGGGTGGGG | 42 |
| 89 | Kras A 120 nt target | TATTTTTATTATAAGGCCTGCTGAAAATGACTG AATATAAACTTGTGGTAGTTGGAGCTGATGGCG TAGGCAAGAGTGCCTTGACGATACAGCTAATTC AGAATCATTTTGTGGACGAAT | 120 |
| 90 | Kras G 120 nt target | TATTTTTATTATAAGGCCTGCTGAAAATGACTG AATATAAACTTGTGGTAGTTGGAGCTGGTGGCG TAGGCAAGAGTGCCTTGACGATACAGCTAATTC AGAATCATTTTGTGGACGAAT | 120 |

Probes cNCB_1 and cNCB_2 were specifically designed to differentiate a single-nucleotide substitution (G→T) in codon 12 of the Kras oncogene (Rs121913529). The "G" nucleotide represents the wild-type sequence (Sample B or reference sequence), and the "T" nucleotide represents the mutant sequence (Sample A or test nucleotide sequence) in this scenario. The cNCB_1 was generated by mixing "NC probe_1" (SEQ ID NO: 16) with "G-rich probe_1" (SEQ ID NO: 18), and the cNCB_2 was generated by mixing "NC probe_2" (SEQ ID NO: 17) with "G-rich probe_1" (SEQ ID NO: 18). Thus, cNCB_1 and _2 shared a common enhancer sequence.

Figure 5C:
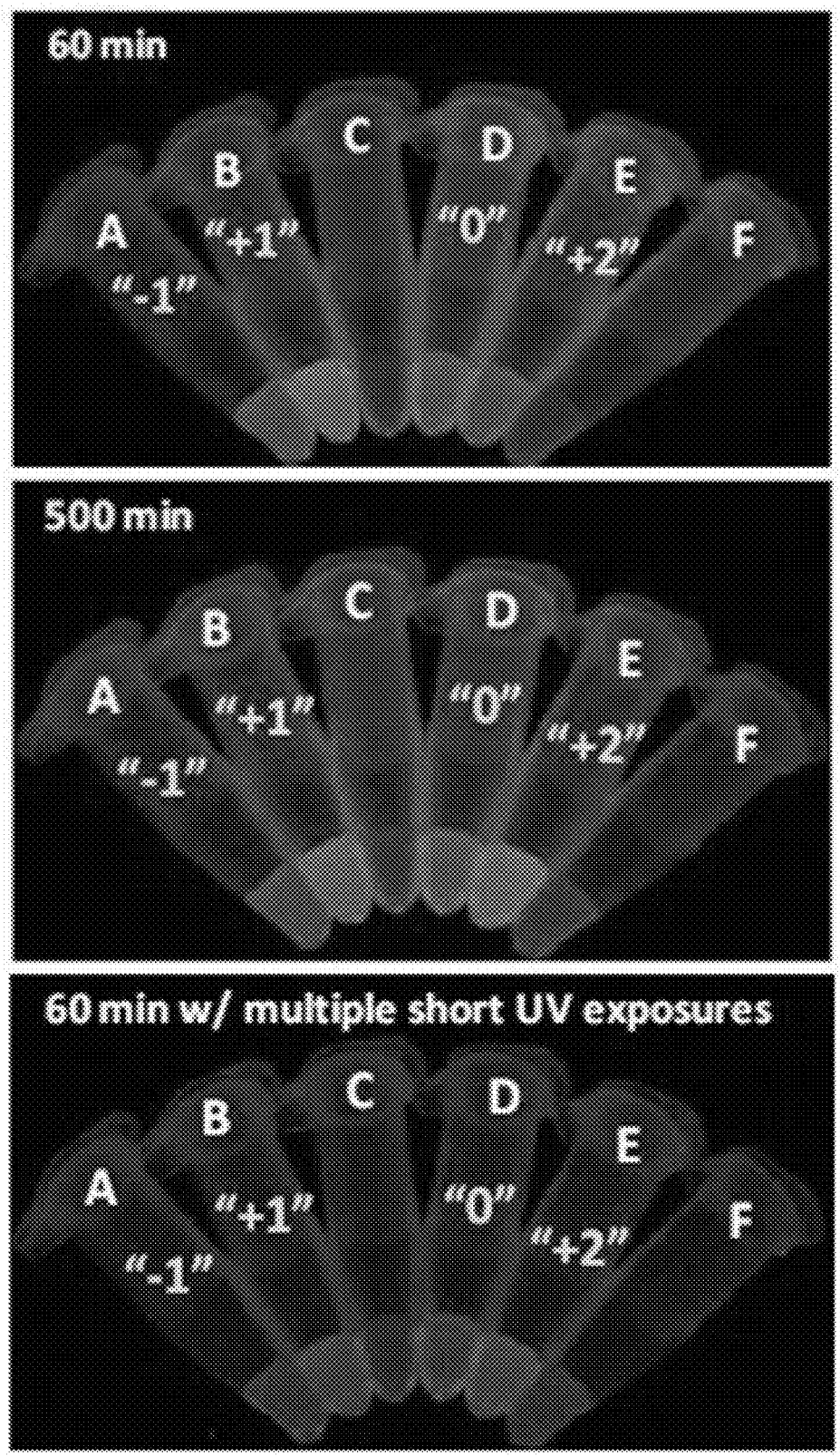
Figure 5D:
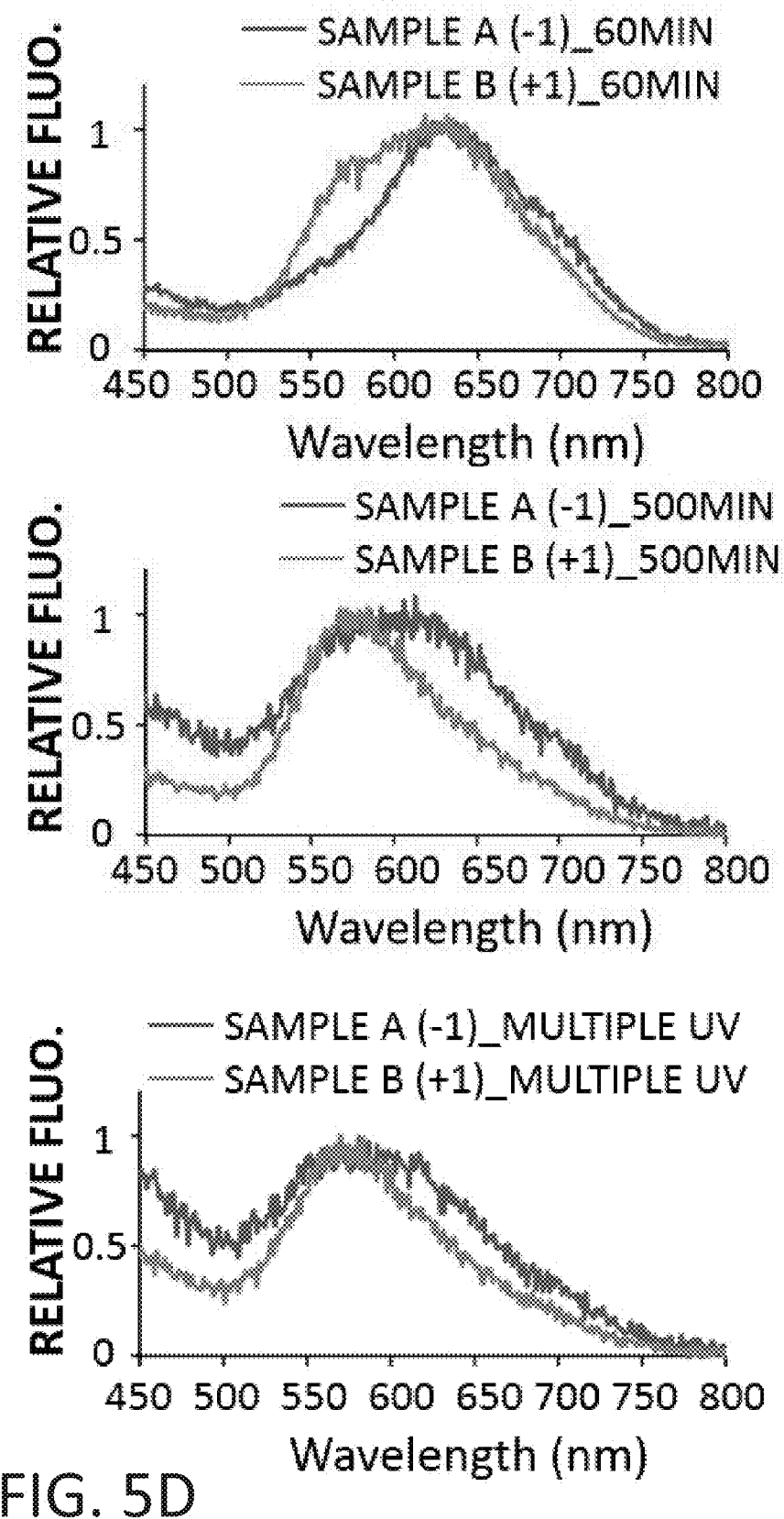
Figure 5E:
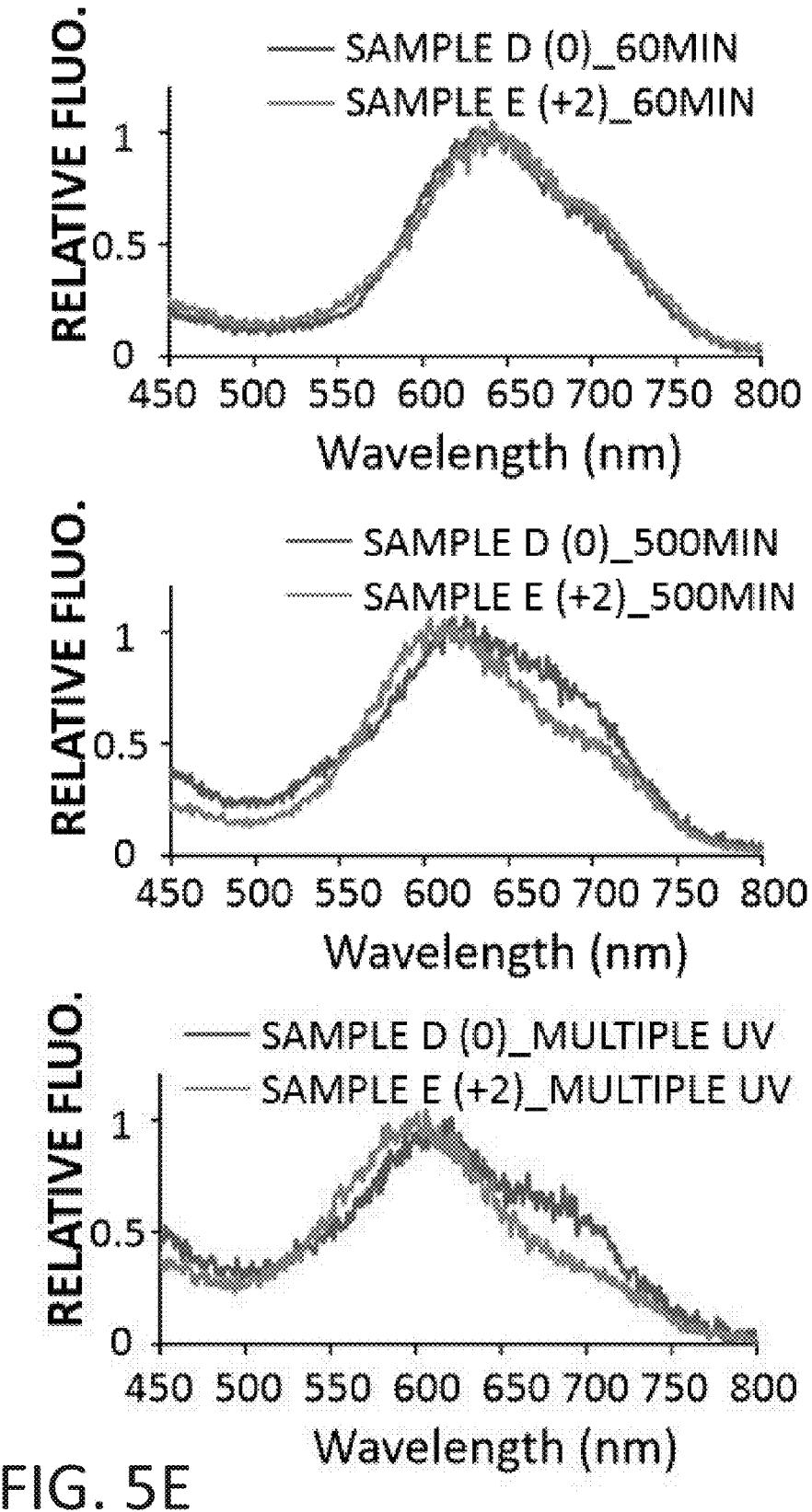
Figure 6A:
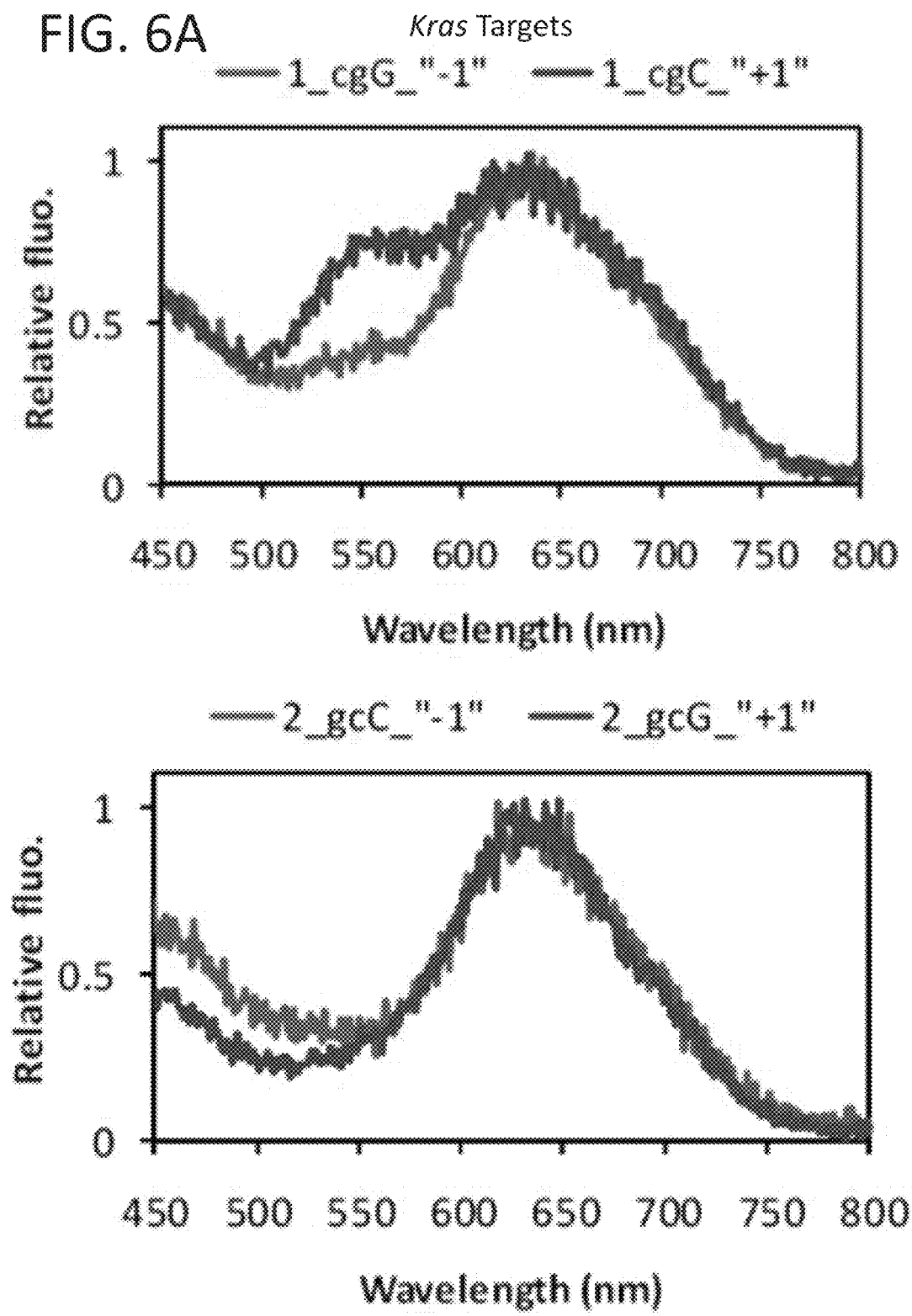
Figure 6F:
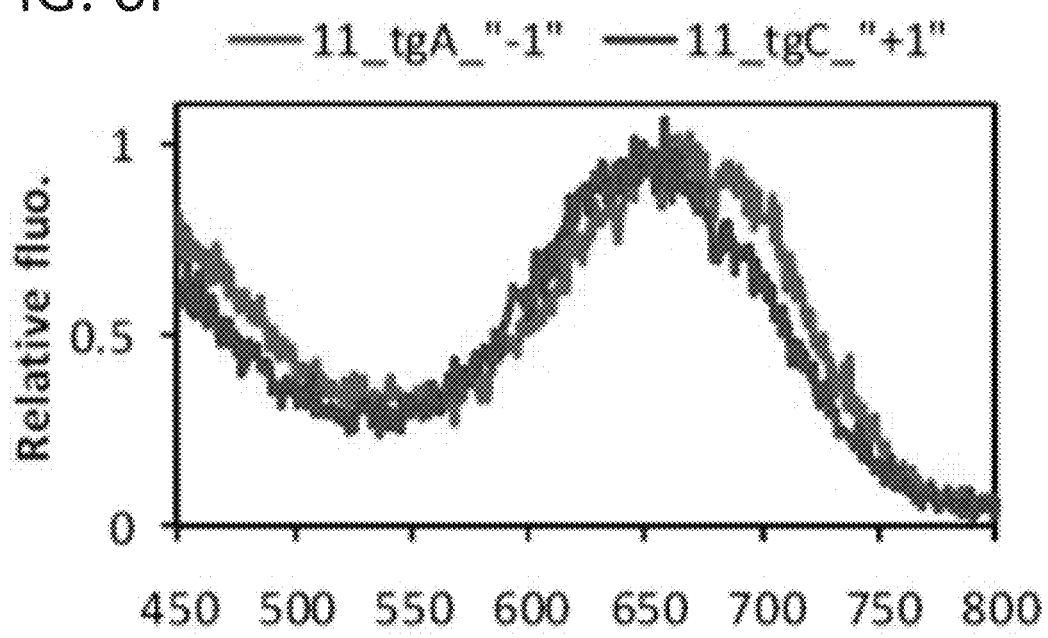
Figure 6F:
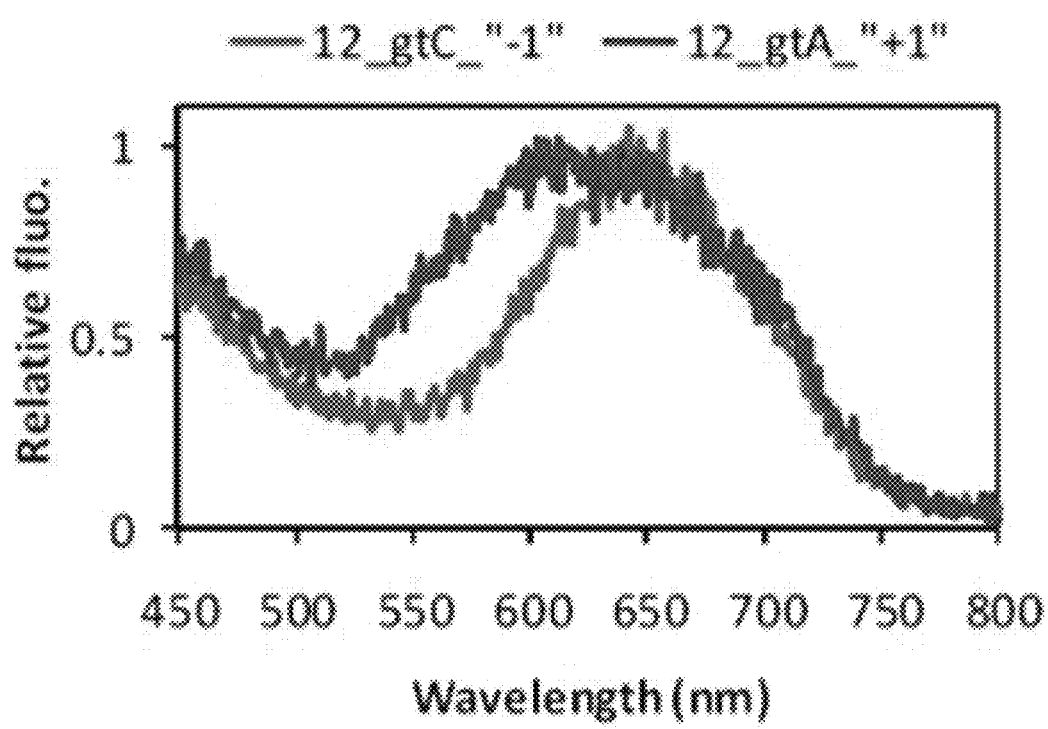
Figure 7E:
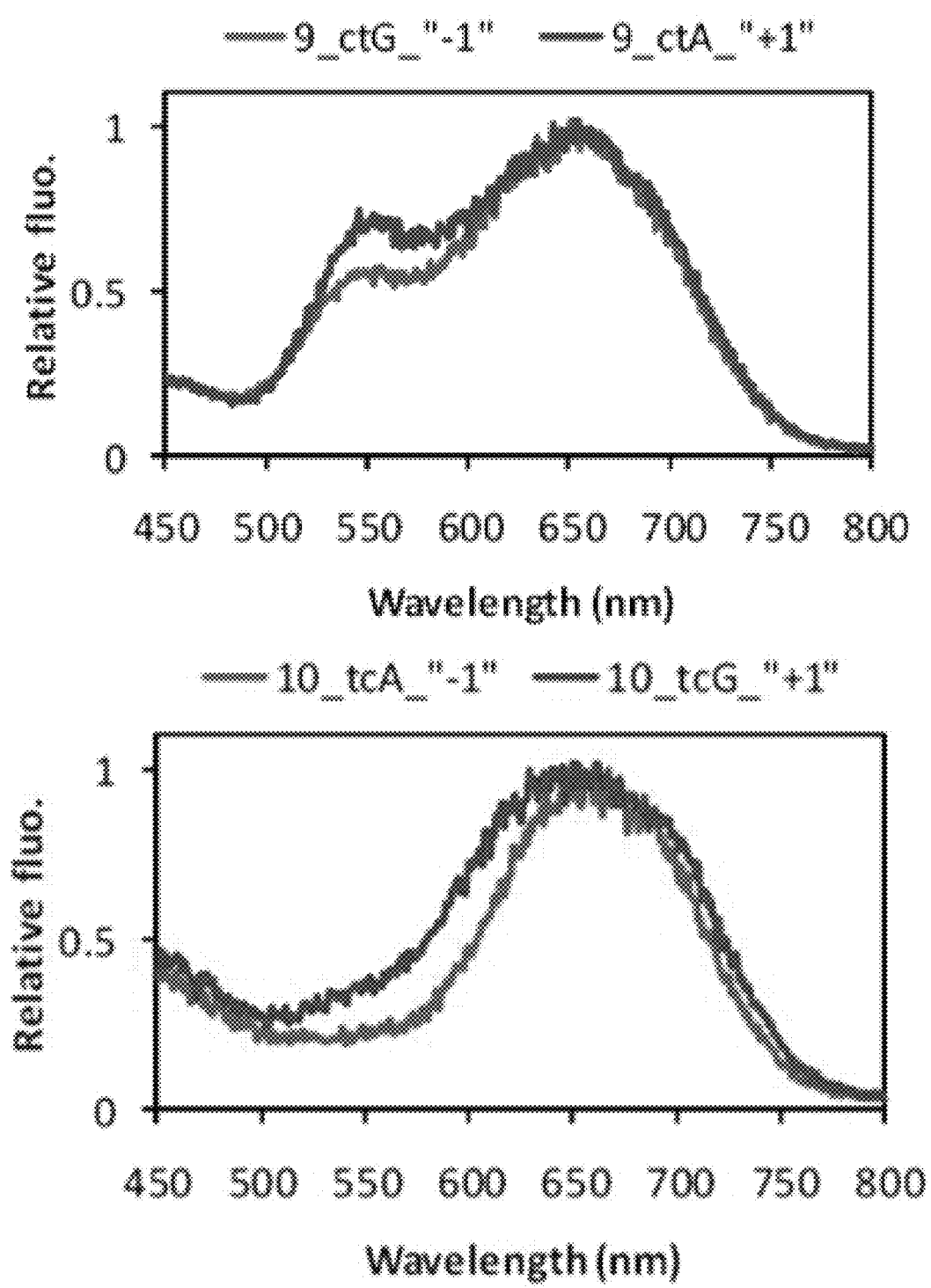
Figure 7F:
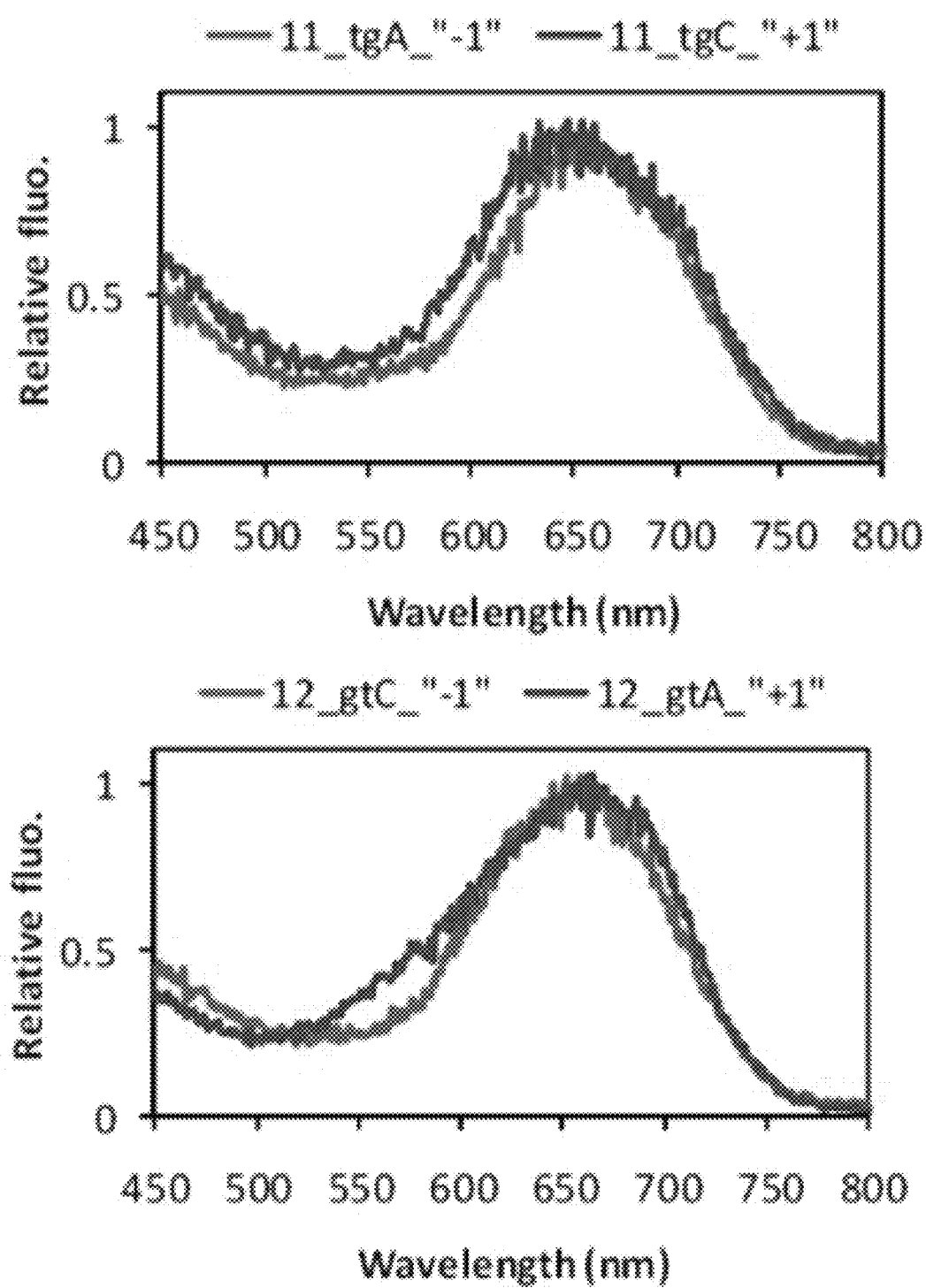
Figure 8B:
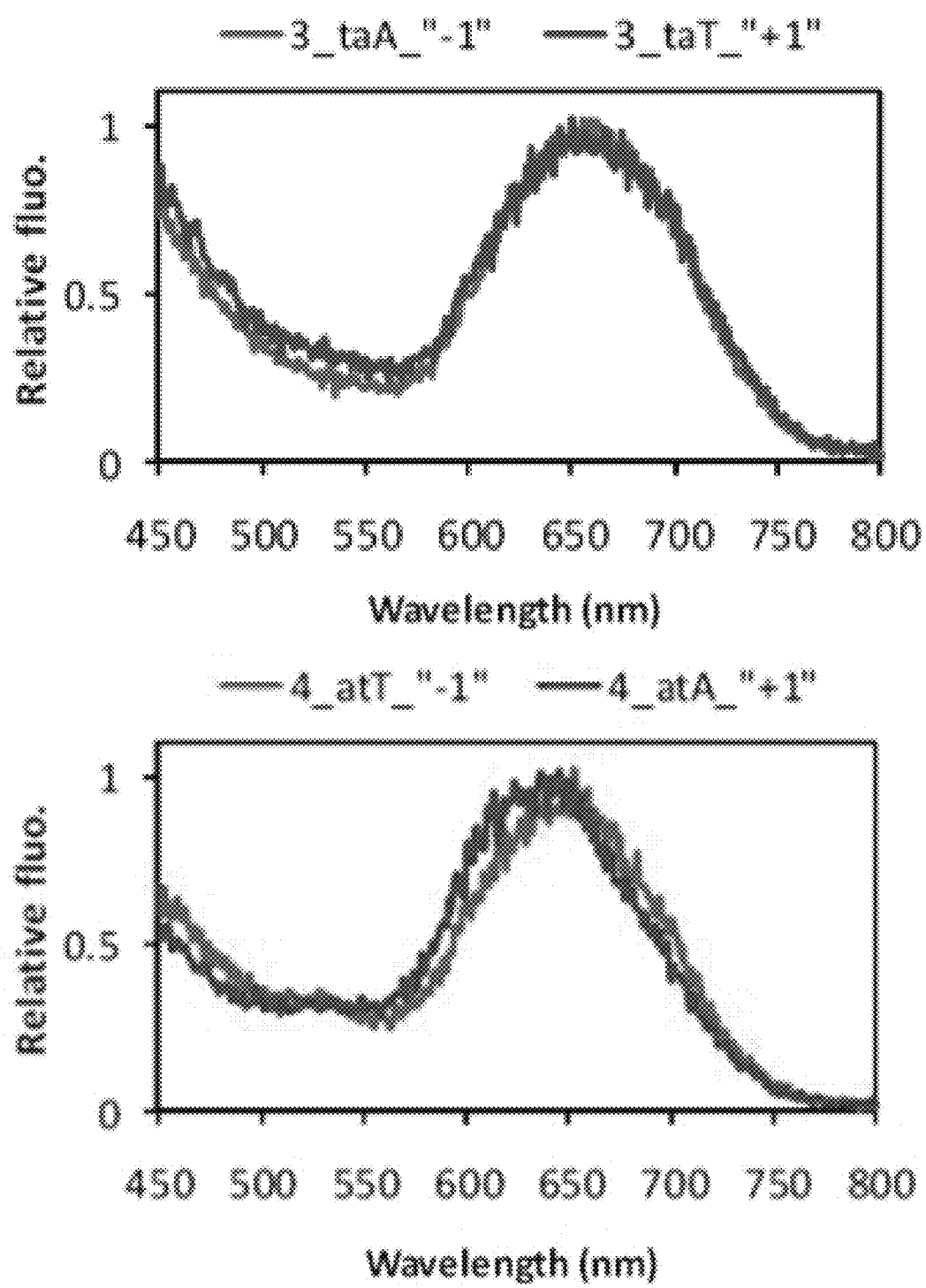

FIGS. 5A and 5B, schematically shows how the cNCB_1 was employed to differentiate a G→T single nucleotide change. Two 3-way-junction (3WJ) structures are shown as Sample A and Sample B, which share the same cNCB_1 but different target nucleotide sequence. Sample A contains the Kras mutant-type target (T nucleotide; GTT), and Sample B contains the Kras wild-type target (G nucleotide; GGT). The light-up color for position +1 sample (Sample B; wild-type target) appeared more orange in color compared to the color for position −1 sample (Sample A; mutant-type target), which appeared more red in color. FIG. 5C shows the side-by-side comparison in the color difference between Samples A and B after 60 minutes and 500 minutes of UV light exposure, and after 60 minutes with short UV exposures of 15 sets of 20-second exposures with 20 seconds of waiting time between each exposure (all exposures were done at 365 nm with a power density ~1 mW/cm$^2$). Samples C and F in FIG. 5C are controls and have a cNCB but no target. FIGS. 5D and 5E show the emission spectra (under 365 nm excitation) of the samples at 60 minutes (top), 500 minutes (middle) and 60 minutes with multiple UV exposures (bottom). Thus, the change in color emitted by the cNCB_1 due to the presence of a single-nucleotide change in the reference sequence (wild-type in this case) to which the probe binds to, indicates that the probes of this disclosure are capable of discriminating a single-nucleotide change.

The cNCB_2 was also used to discriminate the same G→T single nucleotide change in the Kras mutant-type target (Sample D; position 0) and wild-type target (Sample E; position +2) by the same color-switching sensing as the cNCB_1. The cNCB_2 uses a different G-rich probe than the cNCB_1, which relies on positions 0 and +2 for its color-switching. See FIG. 5A is a schematic showing the 3WJ structures for Sample D and Sample E for the cNCB_2 with the Kras mutant (Sample D) and wild-type (Sample E) targets; FIG. 5C for the side by side comparison in the color difference between Samples D ("0") and E ("+2") after 60 minutes and 500 minutes of UV light exposure, and after 60 minutes with short UV exposures and FIG. 5C for the emission spectra (under 365 nm excitation) of the samples at 60 minutes (left column), 500 minutes (middle column) and 60 minutes with multiple UV exposures (right column). As shown in FIG. 5B, the light-up color for position 0 sample (Sample D; wild-type target) appeared more red in color compared to the color for position +2 sample (Sample E; mutant-type target). Interestingly, the distinct color variation of the cNCB_2 between the wild-type and mutant target required approximately 500 minutes of exposure time (the 60 minute exposure was difficult to distinguish). However, the multiple short UV exposures accelerated the color differentiation of the cNCB_2 (compare to constant 60 minute exposure; see FIG. 5C left picture to FIG. 5C right picture).

Further, it was shown that cNCBs also function to discriminate single-nucleotide substitutions in longer target sequences (e.g., 120 nts. in length; SEQ ID NOs: 89 and 90).

To further illustrate the dynamic range of the probes of this disclosure, the cNCB_1 probe was tested with all four single-nucleotide variants (G, T, C and A) in the same position of the target sequence, which are represented by Kras targets SEQ ID NOs: 19-22, respectively (see Table 3 above). Existing methods for SNP detection are only capable of differentiating one matched target from three mismatched targets (i.e., only two different results for 4 different nucleotide variants). In the case of the probes of the instant disclosure, three distinguishable and reproducible emission spectra were generated for the four variants (red, orange and green/blue). Table 4 below summarizes the emission spectra for the four different single-nucleotide variants with the cNCB_1 probe.

TABLE 4

| Nucleotide Variant Kras SNP Target | Color Emission by cNCB_1 Probe (365 nm Excitation) |
|---|---|
| GTT (SEQ ID NO: 20) | Red |
| GGT (wild-type sequence) (SEQ ID NO: 19) | Orange |
| GAT (SEQ ID NO: 22) | Red/Orange |
| GCT (SEQ ID NO: 21) | Red/Orange |
| Control | No color |

The results above show that cNCB_1 and cNCB_2 specifically differentiated a G→T single-nucleotide substitution in codon 12 of the Kras oncogene. Additional cNCBs were synthesized to detect any type of single-nucleotide substitution scenario (i.e., G↔C, A↔T, T↔G, T↔C, G↔A, and A↔C). Table 3 shows the various Kras specific NC-sequences and G-rich sequences were used in various combinations to create a series of cNCBs that differentiated the six possible single-nucleotide substitutions. Each of the twelve sample sets were made with a unique cNCB. Each substitution scenario was tested with two cNCBs. For example, the Kras NC probe c (SEQ ID NO: 25) and Kras G-rich probe g (SEQ ID NO: 27) made a sample set and were used to differentiate a G↔C substitution scenario. FIGS. 6A-6F summarize the emission spectra for the 12 sample sets of cNCB Kras specific probes with all 6 single-nucleotide substitutions scenarios, under 365 nm excitation. As shown in FIGS. 6A-6F, all six single-nucleotide substitution scenarios were differentiated with at least one cNCB.

Example 4

Detection of Single-Nucleotide Substitutions in a Braf Nucleotide Sequence with cNCBs This example shows that cNCBs detect single-nucleotide substitutions in a disease related SNP Braf nucleotide sequence target. This example validates the application of these probes as a tool for detecting SNPs related to disease states and conditions in subjects.

Table 5 below provides the nucleic acid sequences of the target sequences and the associated NC-nucleation ("NC-probe") and enhancer ("G-rich probe") sequences. The NC-nucleation and enhancer sequences are shown in bold type font. The SNP sites and the nucleotides designed to generate frame-shift base pairing are italicized.

TABLE 5

| SEQ ID NO: | Name of probe | Sequence (5'-3') | Length (nts.) |
|---|---|---|---|
| 31 | Braf_G_target | TAA AAA TAG GTG ATT TTG GTC TAG CTA CAG G GA AAT CTC GAT GGA GTG GGT CCC ATC AGT | 60 |
| 32 | Braf_T_target | TAA AAA TAG GTG ATT TTG GTC TAG CTA CAG T GA AAT CTC GAT GGA GTG GGT CCC ATC AGT | 60 |
| 33 | Braf_C_target | TAA AAA TAG GTG ATT TTG GTC TAG CTA CAG C GA AAT CTC GAT GGA GTG GGT CCC ATC AGT | 60 |
| 34 | Braf_A_target | TAA AAA TAG GTG ATT TTG GTC TAG CTA CAG A GA AAT CTC GAT GGA GTG GGT CCC ATC AGT | 60 |
| 35 | Braf_NC probe_g | CCC TTAAT CCCC *G* CTG TAG CTA GAC CAA AAT CAC CTA | 37 |
| 36 | Braf_NC probe_t | CCC TTAAT CCCC *T* CTG TAG CTA GAC CAA AAT CAC CTA | 37 |
| 37 | Braf_NC probe_c | CCC TTAAT CCCC *C* CTG TAG CTA GAC CAA AAT CAC CTA | 37 |
| 38 | Braf_NC probe_a | CCC TTAAT CCCC *A* CTG TAG CTA GAC CAA AAT CAC CTA | 37 |
| 39 | Braf_G-rich probe_g | GGG ACC CAC TCC ATC GAG ATT TC *G* GGGTGGGGTGGGGTGGGG | 42 |
| 40 | Braf_G-rich probe_t | GGG ACC CAC TCC ATC GAG ATT TC *T* GGGTGGGGTGGGGTGGGG | 42 |
| 41 | Braf_G-rich probe_c | GGG ACC CAC TCC ATC GAG ATT TC *C* GGGTGGGGTGGGGTGGGG | 42 |
| 42 | Braf_G-rich probe_a | GGG ACC CAC TCC ATC GAG ATT TC *A* GGGTGGGGTGGGGTGGGG | 42 |

The method described in Example 3 to detect the six single-nucleotide substitution scenario (i.e., G↔C, A↔T, T↔G, T↔C, G↔A, and A↔C) in a Kras sequence was applied to a Braf sequence to detect a known Braf SNP (Rs113488022). Table 5 shows the various Braf specific NC-sequences and G-rich sequences were used in various combinations to create a series of cNCBs that differentiated the six possible single-nucleotide substitutions. Each of the twelve sample sets were made with a unique cNCB. Each substitution scenario was tested with two cNCBs. FIGS. 7A-7F summarize the emission spectra for the 12 sample sets of cNCB Braf specific probes with all 6 single-nucleotide substitutions scenarios, under 365 nm excitation. As shown in FIGS. 7A-7F, all size single-nucleotide substitution scenarios were differentiated with at least one cNCB.

Example 5

Detection of Disease Related Single-Nucleotide Substitutions for Sickle-Cell Anemia with cNCBs This example shows that cNCBs detect single-nucleotide substitutions in a Sickle-Cell Anemia disease related nucleotide sequence. This example validates the application of these probes as a tool for detecting SNPs related to disease states and conditions in subjects.

Table 6 below provides the nucleic acid sequences of the target sequences and the associated NC-nucleation ("NC-probe") and enhancer ("G-rich probe") sequences. The NC-nucleation and enhancer sequences are shown in bold type font. The SNP sites and the nucleotides designed to generate frame-shift base pairing are italicized.

Table 6 shows the sequences of the specific NC-sequences and G-rich sequences were used in various combinations to create a series of cNCBs that differentiated the six possible single-nucleotide substitutions in a Sickle-Cell Anemia disease related nucleotide sequence. Each of the twelve sample sets were made with a unique cNCB. Each substitution scenario was tested with two cNCBs. FIGS. 8A-8F summarize the emission spectra for the 12 sample sets of cNCB specific probes with all 6 single-nucleotide substitutions scenarios, under 365 nm excitation. As shown in FIGS. 6A-6F, all size single-nucleotide substitution scenarios were differentiated with at least one cNCB.

Example 6

Detection of Disease Single-Nucleotide Substitutions for Tay-Sachs Disease with cNCBs This example shows that cNCBs detect single-nucleotide substitutions in a Tay-Sachs disease related nucleotide sequence. This example validates the application of these probes as a tool for detecting SNPs related to disease states and conditions in subjects.

Table 7 below provides the nucleic acid sequences of the target sequence (wild-type or "WT" sequence) used as a reference for comparison to the test sequence (Tay-Sachs (TS) disease carrier sequence containing SNP ID

TABLE 6

| SEQ ID NO: | Name of probe | Sequence (5'-3') | Length (nts.) |
|---|---|---|---|
| 43 | SCA_G_target | AAA CAG ACA CCA TGG TGC ACC TGA CTC CTG *G* GG AGA AGT CTG CCG TTA CTG CCC TGT GGG | 60 |
| 44 | SCA_T_target | AAA CAG ACA CCA TGG TGC ACC TGA CTC CTG *T* GG AGA AGT CTG CCG TTA CTG CCC TGT GGG | 60 |
| 45 | SCA_C_target | AAA CAG ACA CCA TGG TGC ACC TGA CTC CTG *C* GG AGA AGT CTG CCG TTA CTG CCC TGT GGG | 60 |
| 46 | SCA_A_target | AAA CAG ACA CCA TGG TGC ACC TGA CTC CTG *A* GG AGA AGT CTG CCG TTA CTG CCC TGT GGG | 60 |
| 47 | SCA_NC probe_g | CCC TTAAT CCCC *G* CAG GAG TCA GGT GCA CCA TGG TGT | 37 |
| 48 | SCA_NC probe_t | CCC TTAAT CCCC *T* CAG GAG TCA GGT GCA CCA TGG TGT | 37 |
| 49 | SCA_NC probe_c | CCC TTAAT CCCC *C* CAG GAG TCA GGT GCA CCA TGG TGT | 37 |
| 50 | SCA_NC probe_a | CCC TTAAT CCCC *A* CAG GAG TCA GGT GCA CCA TGG TGT | 37 |
| 51 | SCA-G-rich probe_g | GGG CAG TAA CGG CAG ACT TCT CC *G* GGGTGGGGTGGGGTGGGG | 42 |
| 52 | SCA-G-rich probe_t | GGG CAG TAA CGG CAG ACT TCT CC *T* GGGTGGGGTGGGGTGGGG | 42 |
| 53 | SCA_G-rich probe_c | GGG CAG TAA CGG CAG ACT TCT CC *C* GGGTGGGGTGGGGTGGGG | 42 |
| 54 | SCA-G-rich probe_a | GGG CAG TAA CGG CAG ACT TCT CC *A* GGGTGGGGTGGGGTGGGG | 42 |

The method described in Example 3 to detect the six single-nucleotide substitution scenario (i.e., G↔C, A↔T, T↔G, T↔C, G↔A, and A↔C) in a Kras sequence was applied to a Sickle-Cell Anemia disease related nucleotide sequence to detect a known sickle cell anemia SNP (Rs344).

Rs28940871) and the associated NC-nucleation ("NC-probe") and enhancer ("G-rich probe") sequences. The NC-nucleation and enhancer sequences are shown in bold type font. The SNP sites and the nucleotides designed to generate frame-shift base pairing are italicized.

TABLE 7

| SEQ ID NO: | Name of probe | Sequence (5'-3') |
|---|---|---|
| 63 | WT Sequence C_target | GCATTTGAAG GTACCCCTGA GCAGAAGGCT C TGGTGATTGG TGGAGAGGCT TGTATGTGG |
| 64 | Tay-Sachs Disease Carrier Sequence G_target (SNP ID: Rs28940871) | GCATTTGAAG GTACCCCTGA GCAGAAGGCT G TGGTGATTGG TGGAGAGGCT TGTATGTGG |
| 65 | TS NC probe_c | CCC TTAAT CCCC C AGC CTT CTG CTC AGG GGT ACC TTC |
| 66 | TS G-rich probe_g | ACA AGC CTC TCC ACC AAT CAC CA G GGGTGGGGTGGGGTGGGG |

In this example, the TS cNCB was generated by mixing "TS NC probe_c" (SEQ ID NO: 54) with "TS G-rich probe_g" (SEQ ID NO: 66). Table 8 below summarizes the emission spectra for the single-nucleotide variants with the TS cNCB.

TABLE 8

| Name of Tay-Sachs Nucleotide Sequence | Color Emission by TS cNCB (365 nm Excitation) |
|---|---|
| WT TS Target (C_target) SEQ ID NO: 63 | Orange |
| TS Disease Carrier Test Sequence (G_target) SEQ ID NO: 64 | Red |
| Control | No color |

These results show that the TS cNCB specifically differentiated a C→G single-nucleotide substitution in disease related SNP associated with Tay-Sachs disease.

Example 7

Detection of Disease Related Single-Nucleotide Substitutions for Li-Fraumeni Syndrome with cNCBs This example shows that cNCBs detect single-nucleotide substitutions in a Li-Fraumeni Syndrome related nucleotide sequence. This example validates the application of these probes as a tool for detecting SNPs related to disease states and conditions in subjects.

Table 9 below provides the nucleic acid sequences of the target sequence (wild-type or "WT" sequence) used as a reference for comparison to the test sequence (Li-Fraumeni Syndrome (LFS) disease carrier sequence containing SNP ID Rs28934578) and the associated NC-nucleation ("NC-probe") and enhancer ("G-rich probe") sequences. The NC-nucleation and enhancer sequences are shown in bold type font. The SNP sites and the nucleotides designed to generate frame-shift base pairing are italicized.

TABLE 9

| SEQ ID NO: | Name of probe | Sequence (5'-3') |
|---|---|---|
| 67 | WT Sequence G_target | AGTCACAGCA CATGACGGAG GTTGTGAGGC G CTGCCCCCAC CATGAGCGCT GCTCAGATA |
| 68 | a Li-Fraumeni Syndrome Carrier Sequence A_target (SNP ID: Rs28934578) | AGTCACAGCA CATGACGGAG GTTGTGAGGC A CTGCCCCCAC CATGAGCGCT GCTCAGATA |
| 69 | LFS NC probe_c | CCC TTAAT CCCC C GCC TCA CAA CCT CCG TCA TGT GCT |
| 70 | LFS G-rich probe_t | AGC AGC GCT CAT GGT GGG GGC AG T GGGTGGGGTGGGGTGGGG |

In this example, the LFS cNCB was generated by mixing "LFS NC probe_c" (SEQ ID NO: 69) with "LFS G-rich probe_t" (SEQ ID NO: 70). Table 10 below summarizes the emission spectra for the single-nucleotide variants with the LFS cNCB.

TABLE 10

| Name of Li-Fraumeni Syndrome Nucleotide Sequence | Color Emission by LFS cNCB (365 nm Excitation) |
| --- | --- |
| WT LFS Target (G_target) SEQ ID NO: 67 | Red |
| LFS Disease Carrier Test Sequence (A_target) SEQ ID NO: 68 | Orange |
| Control | No color |

These results show that the LFS cNCB specifically differentiated a G→A single-nucleotide substitution in disease related SNP associated with Li-Fraumeni Syndrome.

Example 8

Detection of Disease Related Single-Nucleotide Substitutions for Werner's Syndrome with cNCBs This example shows that cNCBs detect single-nucleotide substitutions in a Werner's Syndrome related nucleotide sequence. This example validates the application of these probes as a tool for detecting SNPs related to disease states and conditions in subjects.

Table 11 below provides the nucleic acid sequences of the target sequence (wild-type or "WT" sequence) used as a reference for comparison to the test sequence (Werner's Syndrome (WS) disease carrier sequence containing SNP ID Rs17847577) and the associated NC-nucleation ("NC-probe") and enhancer ("G-rich probe") sequences. The NC-nucleation and enhancer sequences are shown in bold type font. The SNP sites and the nucleotides designed to generate frame-shift base pairing are italicized.

In this example, the WS cNCB was generated by mixing "WS NC probe_a" (SEQ ID NO: 73) with "LFS G-rich probe_g" (SEQ ID NO: 74). Table 12 below summarizes the emission spectra for the single-nucleotide variants with the WS cNCB.

TABLE 12

| Name of Werner's Syndrome Nucleotide Sequence | Color Emission by WS cNCB (365 nm Excitation) |
| --- | --- |
| WT WS Target (C_target) SEQ ID NO: 71 | Orange |
| WS Disease Carrier Test Sequence (T_target) SEQ ID NO: 72 | Red |
| Control | No color |

These results show that the WS cNCB specifically differentiated a C→T single-nucleotide substitution in disease related SNP associated with Werner's Syndrome.

Example 9

Detection of Disease Related Single-Nucleotide Substitutions for Type-2 Diabetes with cNCBs This example shows that cNCBs detect single-nucleotide substitutions in a Type-2 Diabetes related nucleotide sequence. This example validates the application of these probes as a tool for detecting SNPs related to disease states and conditions in subjects.

Table 13 below provides the nucleic acid sequences of the target sequence (wild-type or "WT" sequence) used as a reference for comparison to the test sequence (Type-2 Diabetes (T2D) disease carrier sequence containing SNP ID Rs9939609) and the associated NC-nucleation ("NC-probe") and enhancer ("G-rich probe") sequences. The NC-nucleation and enhancer sequences are shown in bold type font. The SNP sites and the nucleotides designed to generate frame-shift base pairing are italicized.

TABLE 11

| SEQ ID NO: | Name of probe | Sequence (5'-3') |
| --- | --- | --- |
| 71 | WT Sequence C_target | GGAGAAGATG TACTTGGAAA TAAAGTGGAA C GAAAAGAAGA TGGATTTGAA GATGGAGTA |
| 72 | Werner's Syndrome Carrier Sequence T_target (SNP ID: Rs28934578) | GGAGAAGATG TACTTGGAAA TAAAGTGGAA *T* GAAAAGAAGA TGGATTTGAA GATGGAGTA |
| 73 | WS NC probe_a | CCC TTAAT CCCC *A* TTC CAC TTT ATT TCC AAG TAC ATC |
| 74 | WS G-rich probe_g | ATC TTC AAA TCC ATC TTC TTT TC *G* GGGTGGGGTGGGGTGGGG |

TABLE 13

| SEQ ID NO: | Name of probe | Sequence (5'-3') |
|---|---|---|
| 75 | WT Sequence T_target | TTCTAGGTTC CTTGCGACTG CTGTGAATTT T GTGATGCACT TGGATAGTCT CTGTTACTC |
| 76 | Type-2 Diabetes Sequence A_target (SNP ID: Rs9939609) | TTCTAGGTTC CTTGCGACTG CTGTGAATTT A GTGATGCACT TGGATAGTCT CTGTTACTC |
| 77 | T2D NC probe_a | CCC TTAAT CCCC A AAA TTC ACA GCA GTC GCA AGG AAC |
| 78 | T2D G-rich probe_t | CAG AGA CTA TCC AAG TGC ATC AC T GGGTGGGGTGGGGTGGGG |

In this example, the T2D cNCB was generated by mixing "T2D NC probe_a" (SEQ ID NO: 77) with "T2D G-rich probe_t" (SEQ ID NO: 78). Table 14 below summarizes the emission spectra for the single-nucleotide variants with the T2D cNCB.

TABLE 14

| Name of Type-2 Diabetes Nucleotide Sequence | Color Emission by T2D cNCB (365 nm Excitation) |
|---|---|
| WT T2D Target (T_target) SEQ ID NO: 75 | Red |
| Type-2 Diabetes Carrier Test Sequence (A_target) SEQ ID NO: 76 | Orange |
| Control | No color |

These results show that the T2D cNCB specifically differentiated a T→A single-nucleotide substitution in disease related SNP associated with Type-2 Diabetes.

Example 10

Detection of Disease Related SNPs Associated with Type-2 Diabetes, Breast Cancer and Aggressive Prostate Cancer with cNCBs This example shows that cNCBs detect single-nucleotide substitutions linked to type-2 diabetes (T2D), breast cancer (BC) and aggressive prostate cancer (APC) associated gene targets. This example validates the application of these probes as a tool for detecting SNPs related to disease states and conditions in subjects.

Table 15 below provides the nucleic acid sequences of the target sequence (wild-type or "WT" sequence) used as a reference for comparison to the test sequence (type-2 diabetes, breast cancer and aggressive prostate cancer associated sequence containing SNP ID Rs9939609) and the associated NC-nucleation ("NC-probe") and enhancer ("G-rich probe") sequences. The NC-nucleation and enhancer sequences are shown in bold type font. The SNP sites and the nucleotides designed to generate frame-shift base pairing are italicized.

TABLE 15

| SEQ ID NO: | Name of probe | Sequence (5'-3') |
|---|---|---|
| 79 | WT Sequence G_target | TGAGCTGCCC AGGAATATCC AGGCAAGAAT *G* ACCATATTCT GATAATTACT CAGGCCTCT |
| 80 | T2D/BC/APC Sequence T_target (SNP ID: Rs9939609) | TGAGCTGCCC AGGAATATCC AGGCAAGAAT *T* ACCATATTCT GATAATTACT CAGGCCTCT |
| 81 | T2D/BC/APC NC probe_a | CCC TTAAT CCCC *A* ATT CTT GCC TGG ATA TTC CTG GGC |
| 82 | T2D/BC/APC G-rich probe_c | CTG AGT AAT TAT CAG AAT ATG GT *C* GGGTGGGGTGGGGTGGGG |

In this example, the T2D/BC/APC cNCB was generated by mixing "T2D/BC/APC NC probe_a" (SEQ ID NO: 81) with "T2D/BC/APC G-rich probe_c" (SEQ ID NO: 82). Table 16 below summarizes the emission spectra for the single-nucleotide variants with the T2D/BC/APC cNCB.

TABLE 16

| Name of T2D/BC/APC Nucleotide Sequence | Color Emission by T2D/BC/APC cNCB (365 nm Excitation) |
|---|---|
| WT T2D/BC/APC Target (G_target) SEQ ID NO: 79 | Orange |
| T2D/BC/APC Carrier Test Sequence (T_target) SEQ ID NO: 80 | Red |
| Control | No color |

These results show that the T2D/BC/APC cNCB specifically differentiated a G→T single-nucleotide substitution in the disease related SNP associated with type-2 diabetes (T2D), breast cancer (BC) and aggressive prostate cancer (APC).

Example 11

Detection of Kras Point Mutations in Clinical Samples with cNCBs

This example shows that cNCBs detect single-nucleotide substitutions in Kras mutant sequences taken from patients with serous borderline tumors (SBTs).

Mutations in the Kras gene have been found in a variety of human neoplasms, including colorectal carcinoma and ovarian serous borderline tumors (SBTs). Kras mutations in SBTs often occur at codon 12, which result in amino acid alterations and constitutive activation of this oncogene.

Clinical specimens were prepared at the Department of Pathology at the Johns Hopkins Hospital using a standard DNA extraction kit, the QIAamp DNA Micro Kit from QIAGEN. The mutation status of Kras in two ovarian serous borderline tumors (SBTs) was validated by Sanger sequencing analysis using an ABI sequencer. Sample A contained wild type GGT site, and the GGT→GAT missense mutation at codon 12, and therefore, represented a heterozygous sample. Sample B and contained only the wild-type Kras gene (GGT sequence; a homozygous sample). Polymerase chain reaction was performed with Taq polymerase and PCR buffers from NEW ENGLAND BioLabs. The PCR products were purified using StrataClean resin from AGILENT TECHNOLOGIES and then dialyzed in 400 mM pH 6.6 sodium phosphate buffer for one day and then dialyzed in deionized water for 3 days (a 5-liter water bath was refreshed daily). The dialyzed PCR products were dehydrated using a speed-vac centrifuge and re-suspended in 20 mM pH 6.6 sodium phosphate buffer, before mixing them with cNCB_3 probe.

The cNCB_3 probe was composed of the NC-nucleation ("NC-probe") sequence SEQ ID NO: 91, and the enhancer ("G-rich probe") SEQ ID NO: 92.

```
NC-probe:
                                        (SEQ ID NO: 91)
5'-CCCTTAATCCCCGTGTCAGCTCCAACTACCACAAGTTTAT-3'

G-rich probe:
                                        (SEQ ID NO: 92)
5'-TCAAGGCACTCTTGCCTACGCCACACA GGGTGGGGTGGGGT
GGGG-3'
```

FIG. 9 shows that the cNCB_3 probe differentiated the GGT→GAT missense mutation at codon 12 for samples taken from patients with SBTs.

In summary, the cNCBs of this disclosure reproducibly discriminate a single-nucleotide change. Further, these probes are capable of producing three distinguishable and reproducible emission spectra from four possible variants (i.e., A, T, G and C). This is in contrast to existing SNP detection methods that are only capable of producing two emission spectra for four possible variants. Moreover, the cNCBs of this disclosure may quantify the relative amount of target present in a sample by fluorescence intensity. Thus, the cNCBs of this disclosure are capable of a two dimensional analysis in SNP detection: 1) emission color identifies the type of target (i.e., SNP variant) and 2) intensity provides the relative amount of the detected SNP present in a sample.

It will be apparent that the precise details of the disclosed embodiments, may be varied or modified without departing from the spirit of the described embodiments. We claim all such modifications and variations that fall within the scope and spirit of the claims below.

It is claimed:

1. A method of detecting a single nucleotide polymorphism in a KRAS gene, comprising:
   (a) hybridizing a set of probes to a DNA sample from a human subject, the set of probes comprising:
   a first probe comprising a nucleic acid sequence set forth as SEQ ID NO: 91, wherein the nucleic acid sequence of the first probe comprises a nucleation sequence bound to templated metal nanoclusters that are fluorescent, and
   a second probe comprising a nucleic acid sequence set forth as SEQ ID NO: 92, wherein the nucleic acid sequence of the second probe comprises an enhancer sequence that enhances the fluorescence of the templated metal nanoclusters;
   and wherein:
   the first and second probes hybridized to the DNA sample form a three-way junction wherein the templated metal nanoclusters of the first probe are proximal to the enhancer sequence of the second probe;
   the polymorphism is positioned at a branch point of the three-way junction;
   the presence of the polymorphism causes a shift in alignment of the templated metal nanoclusters relative to the enhancer sequence compared to a wild-type control, resulting in a detectable change in a fluorescence emission wavelength of the metal nanoclusters; and
   wherein the probes do not hybridize to non-target DNA;
   (b) measuring the fluorescence emission wavelength of the probes hybridized to the DNA sample in response to ultraviolet light, visible light, and/or near infrared excitation light, and
   (c) detecting the presence of the single nucleotide polymorphism in the KRAS gene by detecting the detectable change in fluorescence emission wavelength of the metal nanoclusters compared to the wild-type control.

2. The method of claim 1, wherein the excitation light comprises a wavelength of from 200 nm to 2000 nm.

3. The method of claim 1, wherein the association of the enhancer portion and the metal nanoclusters enhances fluorescence emission of the templated metal nanoclusters by at least 2-fold.

4. The method of claim 1, wherein the difference in the wavelength of the fluorescence emission of the test mixture compared to that of the corresponding control mixture is a visible color difference.

5. The method of claim 1, wherein the difference in the wavelength of the fluorescence emission of the test mixture compared to that of the corresponding control mixture is at least 1 nm.

6. The method of claim 1, wherein
   (a) the first probe is no more than 75 nucleotides in length;
   (b) the second probe is no more than 75 nucleotides in length; or
   (c) both (a) and (b).

7. The method of claim 1, wherein the metal of the templated metal nanoclusters is silver, gold or copper.

8. The method of claim 1, wherein
   (a) the first probe consists of the nucleic acid sequence set forth as SEQ ID NO: 91;
   (b) the second probe consists of the nucleic acid sequence set forth as SEQ ID NO: 92; or
   (c) the first and second probes consist of the nucleotide sequences set forth as SEQ ID NOs: 91 and 92, respectively.

* * * * *